United States Patent
Ludwig et al.

(10) Patent No.: US 9,873,864 B2
(45) Date of Patent: Jan. 23, 2018

(54) CELLOBIOSE DEHYDROGENASE

(71) Applicant: DIRECTSENS GMBH, Klosterneuburg (AT)

(72) Inventors: Roland Ludwig, Vienna (AT); Dietmar Haltrich, Vienna (AT); Wolfgang Harreither, Vienna (AT); Lo Gorton, Malmo (SE)

(73) Assignee: DIRECTSENS GMBH, Klosterneuburg (DE)

( * ) Notice: Subject to any disclaimer, the term of this patent is extended or adjusted under 35 U.S.C. 154(b) by 0 days.

(21) Appl. No.: 15/593,507

(22) Filed: May 12, 2017

(65) Prior Publication Data

US 2017/0247666 A1   Aug. 31, 2017

Related U.S. Application Data

(62) Division of application No. 14/730,935, filed on Jun. 4, 2015, now Pat. No. 9,663,767, which is a division of application No. 13/203,711, filed as application No. PCT/EP2010/052488 on Feb. 26, 2010, now Pat. No. 9,051,543.

(30) Foreign Application Priority Data

Feb. 27, 2009 (EP) .................................... 09153889

(51) Int. Cl.
| | |
|---|---|
| C12N 9/04 | (2006.01) |
| G01N 27/327 | (2006.01) |
| G01N 33/66 | (2006.01) |
| C12Q 1/00 | (2006.01) |
| C12Q 1/32 | (2006.01) |

(52) U.S. Cl.
CPC ........... *C12N 9/0006* (2013.01); *C12Q 1/005* (2013.01); *C12Q 1/006* (2013.01); *C12Q 1/32* (2013.01); *C12Y 101/99018* (2013.01); *G01N 27/3271* (2013.01); *G01N 33/66* (2013.01)

(58) Field of Classification Search
CPC combination set(s) only.
See application file for complete search history.

(56) References Cited

U.S. PATENT DOCUMENTS 6,033,891 A    3/2000   Golightly et al. ............ 435/190

OTHER PUBLICATIONS

Database EMBL, [Online] "Myceliophthora thermophila ATCC 42464 cellobiose dehydrogenase (cdh) mRNA, DE complete cds.," EMBL accession No. AF074951, Jul. 15, 1998.
Database Geneseq [Online] "Humicola insolens cellobiose dehydrogenase SEQ ID No. 2." EBI accession No. GSP:AAY82220, Jun. 12, 2000.
Database Geneseq [Online], "Humicola insolens cellobiose dehydrogenase encoding cDNA SEQ ID No. 1." from EBI accession No. GSN:AAZ95701, Mar. 7, 2000.
Database UniProt [Online], "SubName: Full=Cellobiose dehydrogenase;" EBI accession No. UNIPROT:A9XK88, Feb. 26, 2008.
Extended European Search Report issued in European Patent Application No. 09153889, dated May 19, 2009.
Harreither et al., "Investigation of graphite electrodes modified with cellobiose dehydrogenase from the ascomycete myriococcum thermophilum," Electroanalysis, 19:172-180, 2007.
Hennriksson et al., "Substrate specificity of cellobiose dehydrogenase from Phanerochaete chrysosporium," Biochimica Biophysica Acta, 1383:48-54, 1998.
International Search Report and Written Opinion issued in PCT/EP2010/052488, dated May 7, 2010.
Lindgren et al., "Development of a cellobiose dehydrogenase modified electrode for amperometric detection of diphenols ," Analyst, 124:527-532, 1999.
Lindgren et at., "Direct electron transfer of cellobiose dehydrogenase from various biological origins at gold and graphite electrodes," J. Electro. Chem., 496:76-81, 2001.
Ludwig et al., "Characterisation of cellobiose dehydrogenases from the white-rot fungi *Trametes pubescens* and *Trametes villosa*," Appl. Microbiol. Biotechnol., 64:213-222, 2004.
Schou et al., "Characterization of a cellobiose dehydrogenase from Humicola insolens ," Biochem. Journal, 330:565-571, 1998.
Stoica et al., "Biosensor based on cellobiose dehydrogenase for detection of catecholamines," Anal Chem., 76:4690-4696, 2004.
Stoica et al., "Electrochemical investigation of cellobiose dehydrogenase from new fungal sources on Au electrodes," Biosens. Bioelectron., 20:2010-2018, 2005.
Tasca et al. (Highly efficient and versatile anodes for biofuel cells based on cellulose dehydrogenase from Myriococcum thermophilum, J. Phys. Chem. C 2008, 112, 13668-13673, available on the web on Aug. 12, 2008).
Wolfgang Investigation of Graphite Electrodes Modified with Cellobiose Dehydrogenase from the Ascomycete Myriococcum thermophilum Electroanalysis 19, 2007, No. 2-3, 172-180.
Zamocky et al., "Cellobiose dehydrogenase—a flavocytochrome from wood-degrading, phytopathogenic and saprotropic fungi.," Curr Protein Pept Sci., 7(3): 255-280, 2006.
Zamocky et al., "Cloning, sequence analysis and heterologous expression in Pichia pastoris of a gene encoding a thermostable cellobiose dehydrogenase from Myriococcum thermophilum," Prot. Expr. Pur. Acad. Press, 59(2): 258-265, 2007.

*Primary Examiner* — Kagnew H Gebreyesus
(74) *Attorney, Agent, or Firm* — Norton Rose Fulbright US LLP

(57) ABSTRACT

The present invention relates to cellobiose dehydrogenases (CDH) having glucose oxidation activity at a pH of 7.4 or above, modifications to modify the pH dependency of the enzymes activity, uses for these CDHs, in particular electrode sensors and electrochemical cells.

9 Claims, 14 Drawing Sheets

Fig. 1

```
↓ start signal peptide
 M   R   T   S   S   R   L   I   G   A   L   A   A   A    14
ATG AGA ACT TCT TCT AGA CTT ATC GGT GCC TTG GCC GCA GCT   42
                                ↓ start haem domain
 L   L   P   S   A   L   A   Q   N   N   V   P   N   T    28
TTG CTT CCT TCT GCC CTT GCT CAG AAT AAC GTT CCA AAC ACC   84

F   T   D   P   D   S   G   I   T   F   N   T   W   G    42
TTT ACT GAC CCT GAC TCC GGT ATC ACT TTC AAC ACT TGG GGA  126

L   D   E   D   S   P   Q   T   Q   G   G   F   T   F    56
CTT GAC GAG GAT TCT CCA CAG ACT CAG GGT GGA TTC ACT TTC  168

G   V   A   L   P   S   D   A   L   T   T   D   A   S    70
GGT GTT GCT TTG CCA TCC GAC GCT TTG ACT ACT GAC GCA TCT  210

E   F   I   G   Y   L   K   C   A   R   N   D   E   S    84
GAG TTC ATC GGT TAC TTG AAG TGT GCT AGA AAT GAC GAG TCC  252
                     *   *   *   *   *   *   *   *   *
 G   W   C   G   I   S   L   G   G   P   M   T   N   S    98
GGA TGG TGT GGT ATT TCC CTT GGT GGT CCT ATG ACT AAC TCC  294
 *   *
 L   L   I   T   A   W   P   H   E   D   T   V   Y   T   112
TTG TTG ATT ACT GCT TGG CCT CAC GAG GAC ACT GTT TAC ACT  336
         *   *   *   *   *   *   *   *   *   *
 S   L   R   F   A   T   G   Y   A   M   P   D   V   Y   126
TCC TTG AGA TTT GCT ACC GGA TAC GCC ATG CCT GAC GTT TAC  378

E   G   D   A   E   I   T   Q   V   S   S   S   V   N   140
GAG GGT GAT GCT GAA ATC ACC CAA GTC TCT TCC TCT GTC AAT  420

S   T   H   F   S   L   I   F   R   C   K   N   C   L   154
TCC ACT CAT TTC TCT TTG ATC TTT AGA TGT AAG AAC TGT TTG  462

Q   W   S   H   G   G   S   S   G   G   A   S   T   S   168
CAA TGG TCC CAC GGA GGT TCT TCT GGT GGT GCT TCT ACC TCC  504
             *   *   *   *   +   *   *   +   +   +   +
 G   G   V   L   V   L   G   W   V   Q   A   F   D   D   182
GGT GGT GTT CTT GTT CTT GGT TGG GTC CAA GCT TTT GAC GAT  546
 *   *   *   *   *   *   *   *   *   *   *   *   +   +
 P   G   N   P   T   C   P   E   Q   I   T   L   Q   Q   196
CCA GGT AAC CCA ACC TGT CCA GAA CAG ATT ACT TTG CAG CAA  588
 *   +   *   *   +   *   *
 H   D   N   G   M   G   I   W   G   A   Q   L   N   T   210
CAC GAC AAT GGA ATG GGT ATT TGG GGT GCA CAA TTG AAT ACC  630

D   A   A   S   P   S   Y   T   D   W   A   A   Q   A   224
GAT GCT GCA TCT CCA TCC TAT ACC GAC TGG GCT GCA CAA GCT  672
             ↓ start linker domain
 T   K   T   V   T   G   D   C   E   G   P   T   E   T   238
ACC AAG ACC GTT ACC GGT GAT TGT GAG GGT CCT ACT GAG ACT  714
```

Fig. 1 Continuation

```
                                                          ↓ start flavin
      S   V   V   G   V   P   V   P   T   G   V   S   F   D    252
     TCT GTG GTC GGT GTT CCA GTT CCA ACT GGA GTT TCT TTC GAT   756
     domain
      Y   I   V   V   G   G   G   A   G   G   I   P   A   A    266
     TAC ATT GTT GTC GGA GGT GGT GCC GGA GGT ATC CCA GCA GCT   798

D   K   L   S   E   A   G   K   S   V   L   L   I   E    280
     GAC AAG CTT TCT GAG GCT GGT AAG TCC GTT TTG CTT ATT GAG   840

K   G   F   A   S   T   A   N   T   G   G   T   L   G    294
     AAG GGT TTC GCT TCT ACC GCT AAT ACC GGA GGT ACT TTG GGT   882

P   E   W   L   E   G   H   D   L   T   R   F   D   V    308
     CCA GAG TGG TTG GAG GGT CAC GAT CTT ACT CGT TTC GAC GTT   924
          *   *   *   *   *   *   *   +   *   *   *   *
      P   G   L   C   N   Q   I   W   V   D   S   K   G   I    322
     CCA GGT CTT TGC AAC CAA ATT TGG GTG GAC TCT AAG GGA ATC   966
      *   *   +   +   *   +   *   *   *   *   *
      A   C   E   D   T   D   Q   M   A   G   C   V   L   G    336
     GCT TGC GAG GAT ACT GAC CAA ATG GCA GGA TGT GTT CTT GGT  1008

G   G   T   A   V   N   A   G   L   W   F   K   P   Y    350
     GGA GGT ACC GCA GTC AAT GCT GGT CTT TGG TTC AAG CCA TAT  1050

S   L   D   W   D   Y   L   F   P   D   G   W   K   Y    364
     TCT TTG GAT TGG GAT TAC TTG TTT CCT GAC GGT TGG AAG TAC  1092

N   D   V   Q   P   A   I   N   R   A   L   S   R   I    378
     AAC GAC GTC CAA CCT GCC ATC AAC AGA GCT TTG TCT CGT ATT  1134

P   G   T   D   A   P   S   T   D   G   K   R   Y   Y    392
     CCT GGT ACT GAC GCT CCT TCT ACT GAC GGA AAG AGA TAC TAC  1176

Q   E   G   F   E   V   L   S   K   G   L   A   A   G    406
     CAG GAA GGT TTT GAG GTT CTT TCT AAA GGT TTG GCC GCT GGT  1218

G   W   T   S   V   T   A   N   N   A   P   D   K   K    420
     GGA TGG ACC TCT GTG ACT GCA AAC AAT GCT CCA GAC AAG AAG  1260

N   R   T   F   A   H   A   P   F   M   F   A   G   G    434
     AAC CGT ACC TTC GCT CAC GCA CCT TTC ATG TTC GCA GGT GGA  1302

E   R   N   G   P   L   G   T   Y   F   Q   T   A   K    448
     GAG AGA AAC GGT CCA TTG GGT ACC TAC TTT CAA ACT GCC AAA  1344

K   R   N   N   F   D   V   W   L   N   T   S   V   K    462
     AAG CGT AAC AAC TTC GAC GTC TGG CTT AAC ACT TCT GTT AAG  1386

R   V   I   R   E   G   G   H   I   T   G   V   E   V    476
     AGA GTT ATC AGA GAA GGA GGT CAC ATT ACT GGA GTT GAA GTG  1428
```

Fig. 1 Continuation

```
      E     P     F     R     D     G     G     Y     E     G     I     V     P     V     490
     GAG   CCT   TTC   AGA   GAT   GGA   GGT   TAC   GAG   GGT   ATC   GTG   CCT   GTG   1470
      T     K     V     T     G     R     V     I     L     S     A     G     T     F     504
     ACT   AAG   GTT   ACT   GGA   CGT   GTT   ATC   TTG   TCT   GCT   GGT   ACT   TTC   1512

G     S     A     K     I     L     L     R     S     G     I     G     P     E     518
     GGT   TCC   GCC   AAG   ATT   CTT   TTG   CGT   TCC   GGT   ATT   GGA   CCA   GAG   1554

D     Q     L     E     V     V     A     A     S     E     K     D     G     P     532
     GAC   CAA   TTG   GAG   GTC   GTT   GCC   GCT   TCT   GAG   AAG   GAT   GGA   CCT   1596

T     M     I     G     N     S     S     W     I     N     L     P     V     G     546
     ACC   ATG   ATC   GGT   AAC   TCC   TCT   TGG   ATT   AAC   TTG   CCT   GTG   GGA   1638

Y     N     L     D     D     H     L     N     T     D     T     V     I     S     560
     TAC   AAC   TTG   GAC   GAT   CAC   TTG   AAC   ACC   GAC   ACC   GTG   ATC   TCT   1680
                         *     *     *     +     *     *     +     *     *     +
      H     P     D     V     V     F     Y     D     F     Y     E     A     W     D     574
     CAC   CCT   GAT   GTG   GTC   TTC   TAT   GAC   TTT   TAC   GAG   GCT   TGG   GAT   1722
      +     *     *
      D     P     I     E     S     D     K     N     S     Y     L     E     S     R     588
     GAC   CCA   ATT   GAA   TCT   GAC   AAG   AAC   TCT   TAC   TTG   GAA   TCT   AGA   1764

T     G     I     L     A     Q     A     A     P     N     I     G     P     M     602
     ACC   GGA   ATC   TTG   GCT   CAA   GCA   GCT   CCA   AAC   ATT   GGT   CCA   ATG   1806

F     W     E     E     I     V     G     A     D     G     I     V     R     Q     616
     TTC   TGG   GAA   GAG   ATT   GTG   GGA   GCT   GAC   GGT   ATT   GTC   AGA   CAA   1848
                                           *     +     *
      L     Q     W     T     A     R     V     E     G     S     L     G     A     P     630
     TTG   CAG   TGG   ACC   GCC   AGA   GTT   GAG   GGT   TCT   TTG   GGT   GCA   CCT   1890

N     G     H     T     M     T     M     S     Q     Y     L     G     R     G     644
     AAC   GGA   CAT   ACC   ATG   ACC   ATG   TCT   CAA   TAC   CTT   GGT   CGT   GGT   1932
                                                       *     +     *     *     *     +
      A     T     S     R     G     R     M     T     I     T     P     S     L     T     658
     GCC   ACT   TCT   AGA   GGT   AGA   ATG   ACC   ATC   ACT   CCA   TCT   TTG   ACC   1974
      *     *     *     *     +     *
      T     I     V     S     D     V     P     Y     L     K     D     P     N     D     672
     ACT   ATT   GTT   TCC   GAC   GTC   CCT   TAC   CTT   AAA   GAC   CCA   AAC   GAC   2016

K     E     A     V     I     Q     G     I     I     N     L     Q     N     A     686
     AAA   GAA   GCC   GTG   ATT   CAA   GGT   ATT   ATC   AAC   TTG   CAG   AAT   GCT   2058
                                                       *     *     *     *     *
      L     Q     N     V     A     N     L     T     W     L     F     P     N     S     700
     TTG   CAG   AAC   GTT   GCC   AAT   TTG   ACC   TGG   TTG   TTC   CCA   AAC   TCT   2100
      *     +     *     *     *     *     *     *     +     *     *     +     *     *
      T     I     T     P     R     E     Y     V     E     S     M     V     V     S     714
     ACC   ATT   ACC   CCA   CGT   GAG   TAT   GTC   GAA   TCT   ATG   GTC   GTG   TCT   2142
      *     *     +     *     *     *     *     *     *
      P     S     N     R     R     S     N     H     W     M     G     T     N     K     728
     CCT   TCT   AAC   AGA   CGT   TCT   AAC   CAC   TGG   ATG   GGT   ACT   AAC   AAA   2184
```

Fig. 1 Continuation

```
      L   G   T   D   D   G   R   K   G   G   S   A   V   V   742
     TTG GGT ACT GAT GAC GGT AGA AAA GGT GGA TCC GCA GTG GTT  2226

D   L   D   T   R   V   Y   G   T   D   N   L   F   V   756
     GAC TTG GAC ACT CGT GTC TAT GGT ACC GAT AAC TTG TTC GTT  2268

I   D   A   S   I   F   P   G   V   P   T   T   N   P   770
     ATC GAT GCT TCC ATC TTC CCT GGT GTT CCT ACC ACT AAC CCA  2310

T   S   Y   I   V   V   A   A   E   H   A   S   S   R   784
     ACT TCT TAC ATT GTC GTT GCC GCA GAG CAC GCT TCC TCT CGT  2352

I   L   A   L   P   D   L   E   P   V   P   K   Y   G   798
     ATT CTT GCA TTG CCA GAC CTT GAG CCA GTC CCT AAA TAC GGA  2394

Q   C   G   G   R   E   W   T   G   S   F   V   C   A   812
     CAG TGT GGT GGA AGA GAG TGG ACT GGA TCT TTC GTT TGC GCA  2436

D   G   S   T   C   E   Y   Q   N   E   W   Y   S   Q   826
     GAT GGT TCT ACC TGT GAA TAC CAA AAT GAG TGG TAC TCT CAA  2478

C   L   *   830
     TGT TTG TAA  2490
```

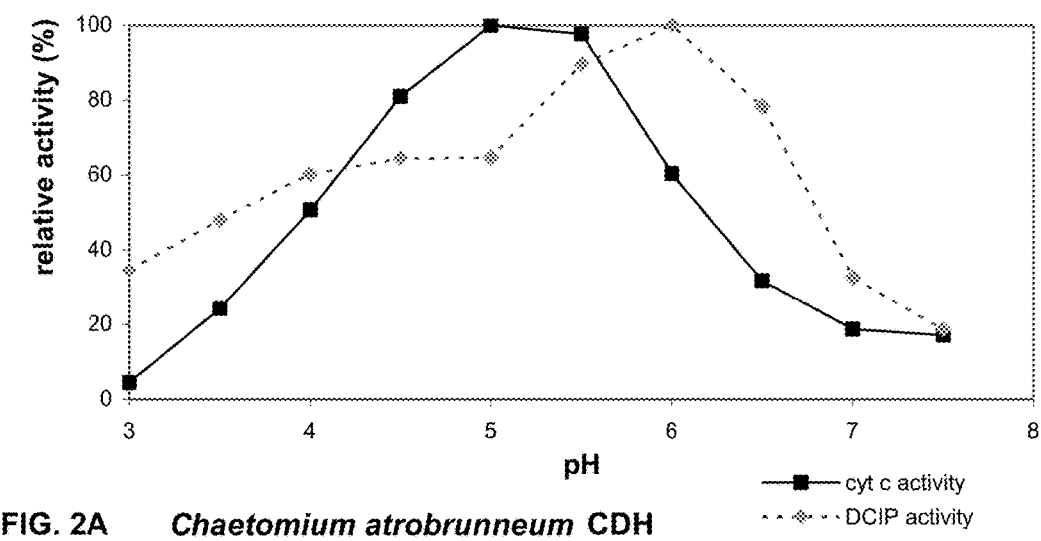
FIG. 2A    *Chaetomium atrobrunneum* CDH
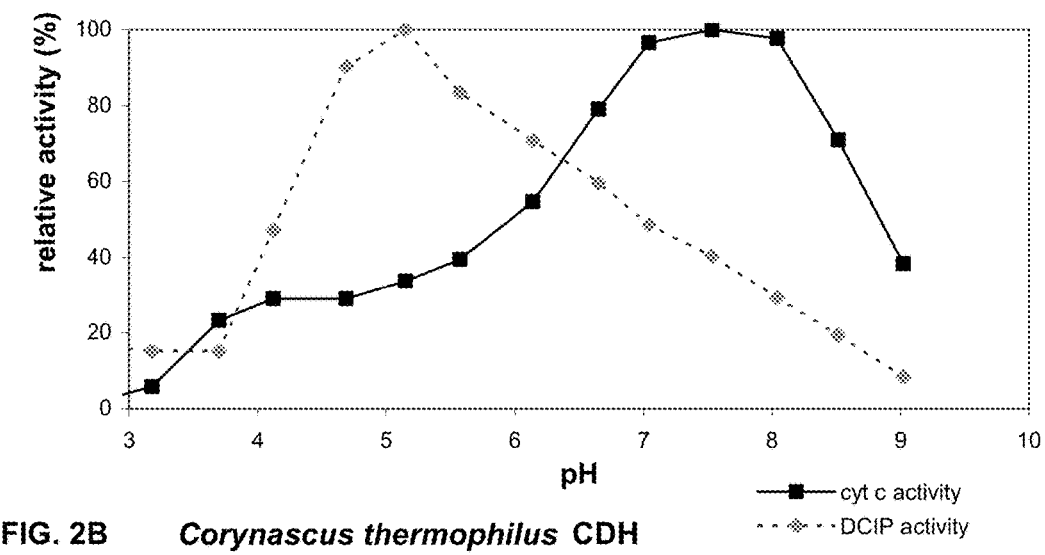
FIG. 2B    *Corynascus thermophilus* CDH

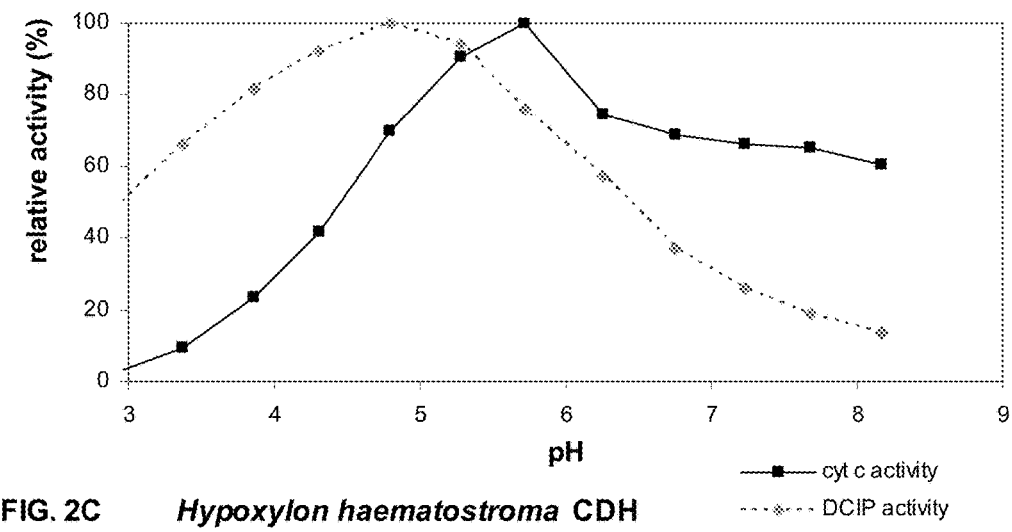
FIG. 2C  *Hypoxylon haematostroma* CDH
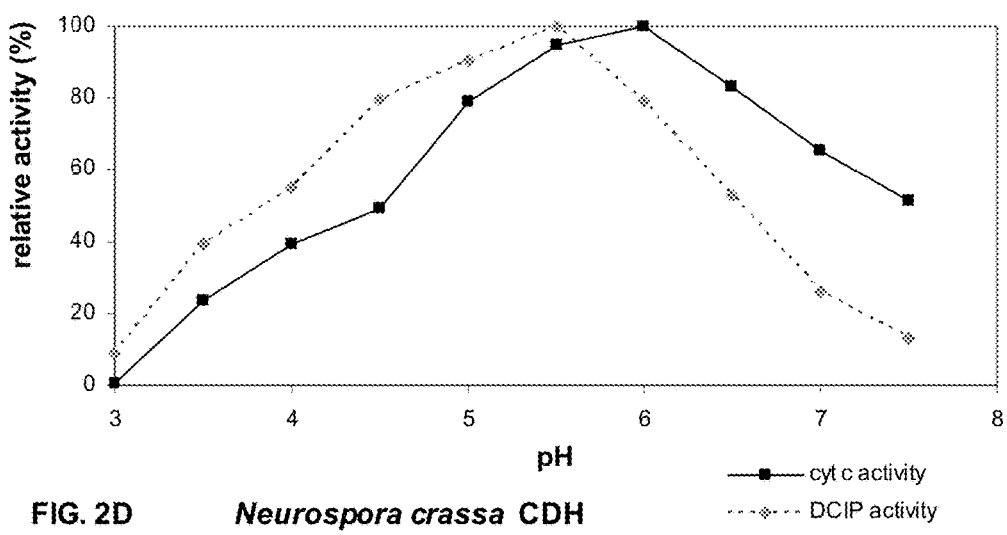
FIG. 2D  *Neurospora crassa* CDH

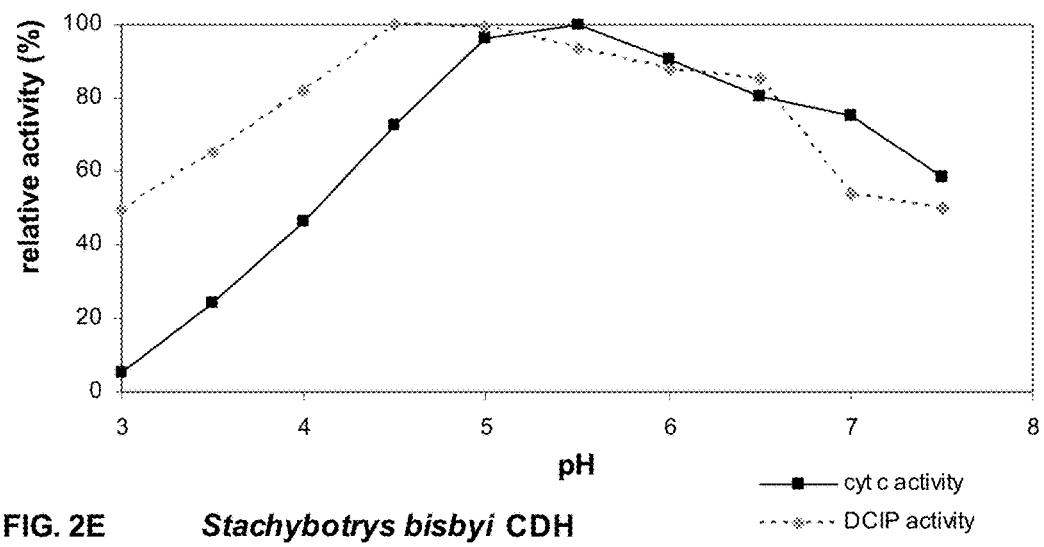
FIG. 2E  *Stachybotrys bisbyi* CDH
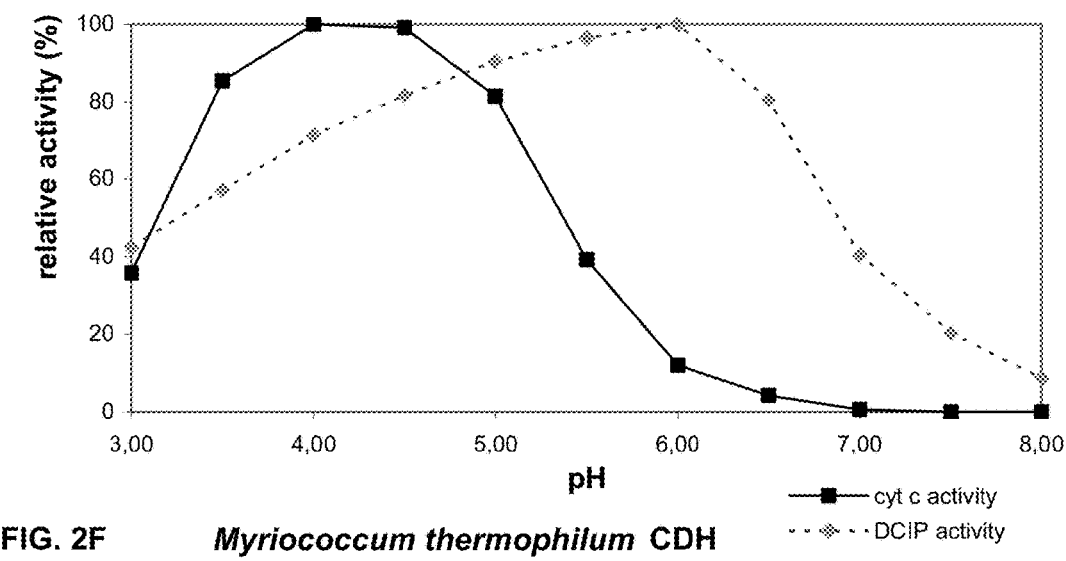
FIG. 2F  *Myriococcum thermophilum* CDH

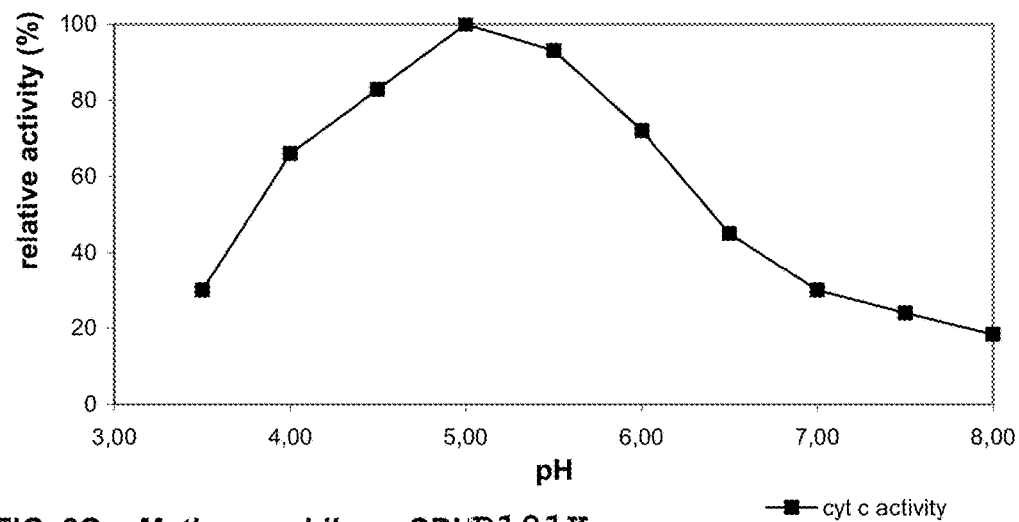
FIG. 2G  *M. thermophilum* CDHD181K
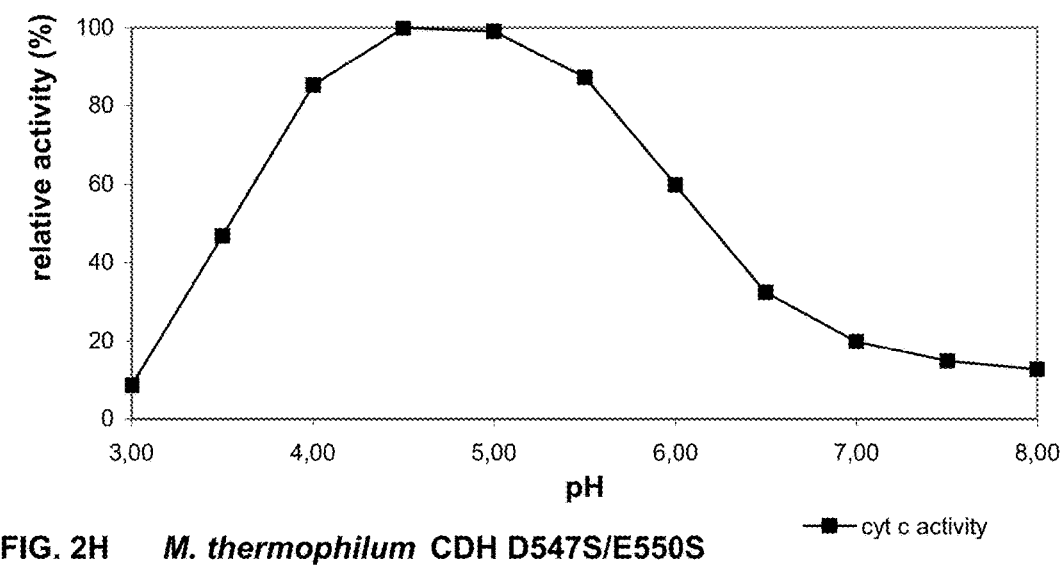
FIG. 2H  *M. thermophilum* CDH D547S/E550S

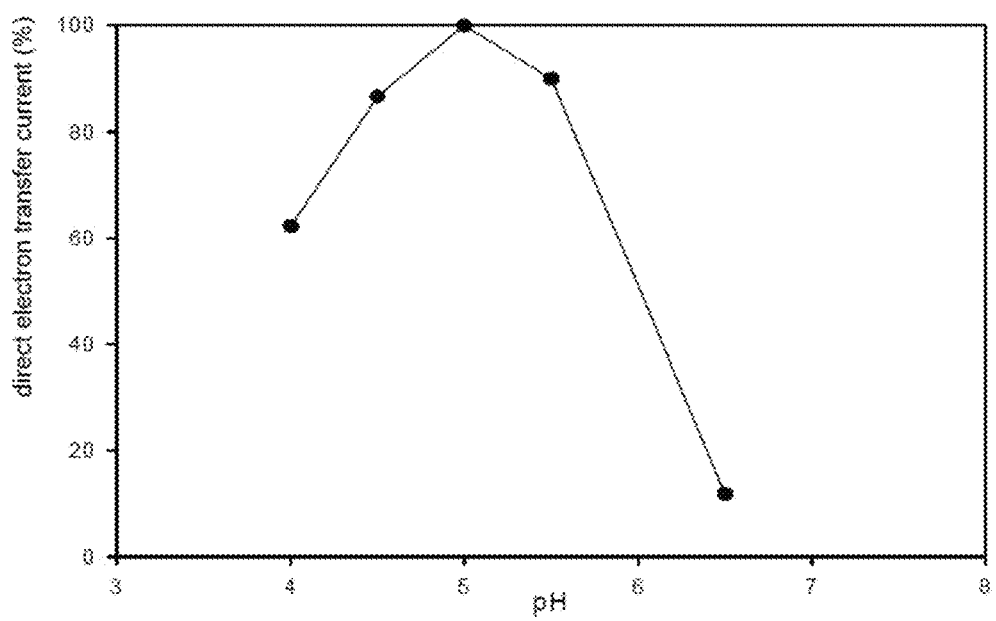
FIG. 21 Relative direct electron transfer current of *Myriococcum thermophilum* CDH with 5 mM glucose.

Fig. 3

```
              *        20         *        40         *        60         *
C.attro : MRPSSRFVGALAAAASFLPSALAQNNAAVTFTDPDTGIVFNSWGLANGAPQTQGGFTFGVALPSDALTTD :  70
C.therm : MKLLSRVGATALAATLSLKQCAAQM-TEGTYTHEATGITFKTWTPSDG-----STFTFGLALPGDALTND :  64
H.haema : MGRLGSLAKLLLAVGLNVQQCFGQNGPPTPYTDSETGITFATWSGGNG-LAPWGGLITFGVALPENALTTD :  69
M.therm : MRTSSRLIGALAAAL--LPSALAQNNVPNTFTDPDSGITFNTWGLDEDSPQTQGGFTFGVALPSDALTTD :  68
N.crass : MRTTSAFLSGLAAVASLLSPAFAQT-APKTFTHPDTGIVFNTWSASD--SQTKGGFTVGMALPSNALTTD :  67
S.bisby : --MLFKLSNWLLALALFVGNVVAQLEGPTPYTDPDTGIVFQSWVNPAG------TLKFGYTYPANAATVA :  62

*        80         *       100         *       120         *       140
C.attro : ATEFIGYLECASADN---QGWCGVSMG--GPMTNSLLITAWPHEDNVYTSLRFATGYAMPDVYSGDATIT : 135
C.therm : ATEYIGLLRCQITDP-SSPGYCGISHGQSGQMTQALLLVAWASEDVVYTSFRYATGYTLPELYTGDAKLT : 133
H.haema : ATELIGYLKCCGSNGT-TTDAWCGLSFG--GPMTNSLLLMAWPHEDEILTSFRFASGYTRPDLYTGDAKLT : 136
M.therm : ASEFIGYLKCARNDE--SGWCGISLG--GPMTNSLLITAWPHEDTVYTSLRFATGYAMPDVYEGDAEIT : 133
N.crass : ATEFIGYLECSSAKNGANSGWCGVSLR--GAMTNNLLITAWPSDGEVYTNLMFATGYAMPKNYAGDAKIT : 135
S.bisby : ATEFIGFLECQ------GAGWCSVSLG--GSMLNKPLVVAYPSGDEVLASLKWATGYANPEPYGGNHKLS : 124

*       160         *       180         *       200         *
C.attro : QISSSINATHFKLIFRCQNCLQWTHDGASGGASTSAGVLVLGWVQAFPSPGNPTCPDQITLEQHNNGMGI : 205
C.therm : QIASSVSGDSFEVLFRCENCFSWDQNGATGSVSTSNGALVLGYAASKSGLIGATCPDTAEFGFHNNGFGQ : 203
H.haema : QISSTIDKDHFTLIFRCQNCLAWNQDGASGASGGASTSAGSLILGWASALRAPTNAGCPAEINFNFHNNGQMI : 206
M.therm : QVSSSVNSTHFSLIFRCKNCLQWSHGGSSGGASTSGGVLVLGWVQAFDDPGNPTCPEQITLQQHDNGMGI : 203
N.crass : QIASSVNATHFTLVFRCQNCLSWDQDGVTGGISTSNKGAQLGWVQAFPSPGNPTCPTQITLSQHDNGMGQ : 205
S.bisby : QISSSVTSAGFRVVYRCEGCLAWNYQGIEGGSPTNGASMPIGWAYSASSVLNGDCVDNTVLIQHDT-FGN : 193

*       220         *       240         *       260         *       280
C.attro : WGAVMDSNVANPSYTEWAAQATKTVEAECDG--PSETDIVGVPVPTGT------TFDYIVVGGAGGI : 265
C.therm : WGAVLEG-ATSDSYEEWAQLATITPPTTCDG--NGPGDKVCVPAPEDT------YDYIVVGAGAGGI : 261
H.haema : WGATLDESAANPSYSEWAAKATATVTGDCGGATPTTTTTTTSVPTATGIPVPT-GTYDYIVVGAGAGGI : 275
M.therm : WGAQLNTDAASPSYTDWAAQATKTVTGDCEG--PTETSVVGVPVPTGV------SFDYIVVGGGAGGI : 263
N.crass : WGAAFDSNIANPSYTAWAAKATKTVTGTCSG--PVTTSIAATPVPTGV------SFDYIVVGGGAGGI : 265
S.bisby : YGFVPDESSLRTEYNDWTELPTRVVRGDCGGSTTTSSVPSSTAPPQGTGIPVPTGASYDYIVVGSGAGGI : 263
```

Fig. 3 Continuation

```
                       *         300         *         320         *         340         *
C.attro  : PTADKLSEAGKSVLLIEKGIASTAEHGGTLGPEWLEGNDLTRFDVPGLCNQIWDSKGIACEDTDQMAGC : 335
C.therm  : TVADKLSEAGHKVLLIEKGPPSTGLWNGTMKPEWLEGTDLTRFDVPGLCNQIWDSAGIACTDTDQMAGC : 331
H.haema  : PLADKLSEAGKSVLLIEKGPPSSGRWGGTLKPEWLKDTNLTRFDVPGLCNQIWNSAGVACTDTDQMAGC : 345
M.therm  : PAADKLSEAGKSVLLIEKGFASTANTGGTLGPEWLEGHDLTRFDVPGLCNQIWDSKGIACEDTDQMAGC : 333
N.crass  : PVADKLSESGKSVLLIEKGFASTGEHGGTLKPEWLNNTSLTRFDVPGLCNQIWKDSDGIACSDTDQMAGC : 335
S.bisby  : PIADKLTEAGKKVLLIEKGPPSSGRYDGKLKPTWLEGTNLTRFDVPGLCNQIWDSAGIACRDTDQMAGC : 333

360         *         380         *         400         *         420         *
C.attro  : VLGGGTAVNAGLWFKPYSLDWDYLFPSGWKYRDIQAAIGRVFSRIPGTDAPSTDGKRYYQQGFDVLAGGL : 405
C.therm  : VLGGGTAVNAGLWWKPHPADWDDNFPHGWKSSDLADATERVFSRIPGTWHPSQDGKLYRQEGFEVISQGL : 401
H.haema  : VLGGGTAVNAGLWWKPYNLDWDYNFPRGWKSRDMAAATRRVFSRIPGTDNPSMDGKRYLQQGFEILAGGL : 415
M.therm  : VLGGGTAVNAGLWFKPYSLDWDYLFPDGWKYNDVQPAINRALSRIPGTDAPSTDGKRYYQEGFEVLSKGL : 403
N.crass  : VLGGGTAINAGLWYKPYTKDWDYLFPSGWKGSDIAGATSRALSRIPGTTTFPSQDGKRYLQQGFEVLANGL : 405
S.bisby  : VLGGGTAVNAGLWWKPNPIDWDYNFPSGWKSSEMIGATNRVFSRIGGTTVPSQDGKTYYQQGFNVLSSGL : 403

*         440         *         460         *         480         *
C.attro  : SAGGWNKVTANSSPDKKNRTFSNAPFMFSGGERGGPLATYLTSAKKRSNFNLWLNTSVKRVIREGGHVTG : 475
C.therm  : ANAGWREVDANQEPSEKNRTYSHSVFMFSGGERGGPLATYLASAAQRSNFNLWVNTSVRRAIRTGPRVSG : 471
H.haema  : KAAGWTEVTANDAPNKKNHTYSHSPFMFSGGERGGPMGTYLVSASRRKNFHLWTGTAVKRVVRTGGHITG : 485
M.therm  : AAGGWTSVTANNAPDKKNRTFAHAPFMFAGGERNGPLGTYFQTAKKRNNFDVWLNTSVKRVIREGGHITG : 473
N.crass  : KASGWKEVDSLKDSEQKNRTFSHTSYMYINGERGGPLATYLVSAKKRSNFKLWLNTAVKRVIREGGHITG : 475
S.bisby  : KAAGWTSVSLNNAPAQRNRTYGAGPFMFSGGERGGPLATYLATAKKRGNFDLWTNTQVKRVIRQGGHVTG : 473

*         500         *         520         *         540         *         560         *
C.attro  : VEVEPFRTGGYQGIVNNVTAVSGRVVLSAGTFGSAKILLRGGIGPADQLEVKASKIDGPTMISNASWIPL : 545
C.therm  : VELECLADGGFNGTVNLKEGGG-VIFSAGAFGSAKLLLRSGIGPEDQLEIVASS-KDGETFISKNDWIKL : 539
H.haema  : LEVEPFVNGGYTGVNVTSITGRVILTGRVILSAGAFGSAKILLRSGIGPEDQLEIVKSS-TDGPTMISDSSWITL : 554
M.therm  : VEVEPFRDGGYEGIVPVTKVTGRVILSAGTFGSAKILLRSGIGPEDQLEVVAASEKDGPTMIGNSSWINL : 543
N.crass  : VEVEAFRNGGYSGIIPVTNTTGRVVLSAGTFGSAKILLRSGIGPKDQLEVVKAS-ADGPTMVSNSSWIDL : 544
S.bisby  : VEVENYNGDGYKGTVKVTPVSGRVVLSAGTFGSAKLLLRSGIGPKDQLAIVKNS-TDGPTMASERDWINL : 542
```

Fig. 3 Continuation

```
                          580             *             600             *             620
C.attro  : PVGYNLDDHLNTDTVITHPDVAFYDFYEAWNTPIEADKNSYLSSRTGILAQAAPNIGPMMWEEIKGADGI : 615
C.therm  : PVGHNLIDHLNTDLIITHPDVVFYDFYDFYDFYEAWDNPITEDKEAYLNSRSGILAQAAPNIGPLMWEEVTPSDGI : 609
H.haema  : PVGYNLEDHTNTDTVTHPDVVFYDFYDFYEAG-HPNVTDKDLYLNSRAGILAQAAPNIGPMFWEEIKGRDGV : 623
M.therm  : PVGYNLDDHLNTDTVISHPDVVFYDFYDFYEAWDPIESDKNSYLESRTGILAQAAPNIGPMFWEEIVGADGI : 613
N.crass  : PVGHNLVDHTNTDTVIQHNNVTFYDFYKAWDNPNTTDMNLYLNGRSGIFAQAAPNIGPLFWEEITGADGI : 614
S.bisby  : PVGYNLEDHTNTDIVISHPDVVHYDFYEAWTASIESDKTAYLGKRSGILAQAAPNIGPLFFDEVRGADNI : 612

640             *             660             *             680             *             700
C.attro  : VRQLQWTARVEG-SFDTPNGQAMTISQYLGRGATSRGRMTITPSLTTVVSDVPYLKDPNDKEAVIQGIVN : 684
C.therm  : TRQFQWTCRVEGDSSKTNSTHAMTLSQYLGRGVVSRGRMGITSGLTTTVAEHPYLHNDGDLEAVIQGIQN : 679
H.haema  : VRQLQWTARVEG-SAGTPNGYAMTMSQYLGRGAKSRGRMTITKALTTVVSTVPYLQDKNDVEAVIQGIKN : 692
M.therm  : VRQLQWTARVEG-SLGAPNGHTMTMSQYLGRGATSRGRMTITPSLTTIVSDVPYLKDPNDKEAVIQGIIN : 682
N.crass  : VRQLHWTARVEG-SFETPDGYAMTMSQYLGRGATSRGRMTLSPTLNTVVSDLPYLKDPNDKAAVVQGIVN : 683
S.bisby  : VRSIQYTARVEG-NSVVPNGKAMVISQYLGRGAVSRGRMTISQGLNTIVSTAPYLSNVNDLEAVIKSLEN : 681

*             720             *             740             *             760             *
C.attro  : LQNALKN-VAGLTWTYPNSSITPREYVDNMVVSPSNRRANHWMGTAKIGTDDGRLAGGSAVVDLNTKVYG : 753
C.therm  : VVDALSQ-VPDLEWVLPPPNTTVEEYVNSLIVSPANRRANHWMGTAKMGLDDGR-SGGGSAVVDLNTKVYG : 747
H.haema  : LQAALSN-VKNLTWAYPPSNTTVEDFVNNMLVSYTNRRSNHWIGTNKLGTDDGRSRGGSAVVDLNTKVYG : 761
M.therm  : LQNALQN-VANLTWLFPNSTITPREYVESMVVSPSNRRSNHWMGTNKLGTDDGR-KGGSAVVDLDTRVYG : 750
N.crass  : LQKALAN-VKGLTWAYPSANQTAADFVDKQPVTYQSRRSNHWMGTNKMGTDDGR-SGGTAVVDTNTRVYG : 751
S.bisby  : IANSLTSKVKNLKIEWPASGTSIRDHVTNMPLDPATRRANHWIGTNKIGTKNGRLTGGDSVVDLNTKVYG : 751

780             *             800             *             820             *             840
C.attro  : TDNLFVVDASIFPGTPTTNPSAYIVTAAEHASQRILGLAAPKPVGKWGQCGGRQWTGSFQCVSGTKCEVV : 823
C.therm  : TDNLFVVDASIFPGMSTGNPSAMIVIVAEQAAQRILSLRY------------------------------ : 787
H.haema  : TDNLFVVDAGIFPGHITTNPTSYIVIAAERASERILDLPPARAQPRFAQCGGRTWTGSFQCAAPYTCQYR : 831
M.therm  : TDNLFVIDASIFPGVPTTNPTSYIVVAAEHASSRILALPDLEPVPKYGQCGGREWTGSFVCADGSTCEYQ : 820
N.crass  : TDNLYVVDASIFPGVPTTNPTAYIVVAAEHAAAKILAQPANEAVPKWGWCGGPTYTGSQTCQAPYKCEKQ : 821
S.bisby  : TDNLFVVDASIFPGMVTTNPSAYIVIAAEHAASKILSLPTAKAAAKYEQCCGGLEYNGNFQCASGLTCTWL : 821
```

Fig. 3 Continuation

```
C.attro : NEWYSQCL : 831
C.therm : ---------- : -
H.haema : NERYSQCR : 839
M.therm : NEWYSQCL : 828
N.crass : NDWYWQCV : 829
S.bisby : NDYYWQCT : 829
```

CELLOBIOSE DEHYDROGENASE

CROSS REFERENCE TO RELATED APPLICATIONS

This application is a divisional of U.S. Ser. No. 14/730,935, filed Jun. 4, 2015, which is a divisional of U.S. patent application Ser. No. 13/203,711, filed Aug. 26, 2011, which is a national phase application under 35 U.S.C. §371 of International Application No. PCT/EP2010/052488, filed Feb. 26, 2010, which claims priority to European Application No. 09153889.2, filed Feb. 27, 2009. The entire text of each of the above-referenced disclosures is specifically incorporated herein by reference without disclaimer.

BACKGROUND

The present invention relates to cellobiose dehydrogenase (CDH) enzymes, modifications thereof and electrochemical uses.

Cellobiose dehydrogenase (EC 1.1.99.18, CDH) was first discovered 1974 in the extracellular enzyme system of *Phanerochaete chrysosporium* and later on in several other basidiomycete fungi. A special characteristic of this enzyme is its composition: the combination of a catalytically active flavin domain, hosting a non-covalently bound FAD, and a haem domain, with a haem b as a cofactor. Both domains are connected by a flexible linker. By its catalytic activity the natural substrate cellobiose is oxidised in a reaction which reduces the FAD of the flavin domain. Subsequently, FAD can be reoxidised by the action of the haem domain. The spectral characteristics of a typical CDH clearly show the presence of both cofactors. Another characteristic described is the strong glucose discrimination of all well characterised enzymes. Until the discovery of the ascomycete fungus *Myriococcum thermophilum* (Stoica et al., 2005, Biosensors and Bioelectronics 20: 2010-2018; Harreither et al., 2007, Electroanalysis 19: 172-180), CDH was believed to strongly inhibit the conversion of glucose (Henriksson et al., 1998, Biochimica Biophysica Acta 1383: 48-54). Similarly, for a long time only CDHs exhibiting an acidic activity optimum were known, especially when the haem domain is involved in catalysis as it depends on intramolecular electron transfer (IET), which is necessary to transfer electrons via the haem to the electron acceptor. This is the case with cytochrome c in enzymatic assays, as well as on electrode surfaces where the haem domain enables direct electron transfer (DET) to the electrode.

Electrochemical applications described in the literature are the detection of cellobiose, cello-oligosaccharides, lactose and maltose soluble cellodextrins, ortho- and paradiphenolic compounds (Lindgren et al., 1999, Analyst 124: 527-532) and catecholamines (Stoica et al., 2004, Analytical Chemistry, 76: 4690-4696) mostly by mediated electron transfer (MET). So far the application in glucose biosensors based on the direct electron transfer (DET) properties of CDH was prevented by i) a very low or no glucose turnover, ii) the acidic pH optimum of most known CDHs and iii) a bad performance of some CDHs on electrodes.

Although, one CDH with well functioning IET at neutral or alkaline pH values is known (from the fungus *Humicola insolens*), it was shown not to convert glucose (Schou et al., 1998, Biochemical Journal 330: 565-571). One CDH currently known to convert glucose with significant turnover numbers was found in cultures of *Myriococcum thermophilum* (Harreither et al., 2007, Electroanalysis 19: 172-180). However, this enzyme has an acidic pH optimum for the IET and shows no activity under physiological pH conditions (pH 7.4). Another obstruction is the sometimes bad electronic communication of a CDH with an electrode surface, like the *Humicola insolens* and *Sclerotium rolfsii* CDHs (Lindgren et al., 2001, Journal of Electroanalytical Chemistry 496: 76-81), which results in very low current densities and therefore low signals even with the natural substrate cellobiose.

Harreither et al. (Electroanalysis, 19 (2-3) (2007): 172-180) disclose CDH direct electron transfer activity assays measured on an electrode. Activity at different pH values was determined with lactose or cellobiose as substrates. Although, glucose is accepted as a substrate at the pH optimum no information of the CDH activity on glucose at pH 7.4 is given. As is shown in the comparative examples herein, the activity of wild type CDH of *M. thermophilum* steeply decreases at neutral pH values above pH 5.5 and has no activity on glucose at pH 7.4.

Zamocky et al. (Prot. Expr. Pur. Acad. Press; 59 (2) (2007): 258-265) discloses the wild type *M. thermophilum* CDH and its DCIP activity when using citrate as substrate. The DCIP activity does not relate to the IEP activity of the catalysis of carbohydrate oxidation reactions on an electrode.

Database UniProt, Acc. No. A9XK88 discloses the wild type CDH sequence of *M. thermophilum*.

U.S. Pat. No. 6,033,891 A discloses a CDH of *Humicola insolens* which does not have a glucose oxidating activity.

Database EMBL, Acc. No. AF074951, AAY82220 and AAZ95701 provide sequences of the CDH from *Thielavia heterothallica*. This enzyme does not have an activity on glucose at pH 7.4.

Zamocky et al. (Current protein and peptide science, 7 (3) (2006); 255-280) provide a review of CDHs of basidiomycetes and ascomycetes.

SUMMARY

Thus CDH activity on glucose under neutral conditions, which is necessary for applications in e.g. physiological fluids is not satisfying, in particular not for the electrochemical measurement of glucose or the generation of electricity in biofuel cells. It is therefore a goal of the present invention to provide an alternative enzyme suitable to convert glucose at physiological pH ranges, in particular on DET-based electrodes.

Therefore, in a first embodiment the present invention provides a CDH having glucose oxidation activity at a pH of 7.4 or above, selected from a CDH isolated from *Chaetomium atrobrunneum, Corynascus thermophilus, Hypoxylon haematostroma, Neurospora crassa* or *Stachybotris bisbyi* or being a modified CDH of *Myriococcum thermophilum*. According to the invention it has been surprisingly found that certain CDHs have a suitable glucose oxidising activity under physiological pH conditions. Furthermore, the invention provides the modification of acidic CDHs to increase their activity at pH 7.4 and above.

The term "cellobiose dehydrogenase" is defined herein as an enzyme consisting of a flavin domain and a haem domain connected by a peptide linker, which oxidises carbohydrates like its natural substrates cellobiose and cello-oligosaccharides and others like lactose, maltose and in particular glucose for preferred inventive uses. The reoxidation of the flavin domain cofactor can be achieved by direct oxidation by two-electron acceptors including quinones like 2,6-dichloroindophenol, o- or p-benzoquinone or derivatives thereof, methylene blue, methylene green, Meldola's blue or one-electron acceptors like potassium ferricyanide, ferricenium hexafluorophosphate, FeCl₃ or by intramolecular electron transfer (IET) to the haem domain cofactor and further to a terminal electron acceptor like cytochrome c (cyt c) or an electrode surface.

The flavin domain of the CDH, which is responsible for the glucose oxidation activity and the haem domain, responsible for the regeneration of the flavin domain, may have two different pH optima, such as in the case of the natural CDH of *Myriococcum thermophilum*. In principle, the haem domain can be bypassed by providing the flavin domain with oxidants such as 2,6-dichloroindophenol which can directly reoxidise the flavin domain without the haem domain. According to the present invention, however, it should be understand that the CDH has a glucose oxidation activity at a pH of 7.4 by the action of both the flavin and the haem domain (IET) as can e.g. be measured by the cyt c assay or by measurement after immobilisation on an electrode surface (DET—direct electron transfer—to the electrode). The haem domain acts as intermediate electron transmitter between cyt c and the flavin domain or between the electrode surface and the flavin domain, respectively.

The natural, wild-type CDH of *M. thermophilum* does not have the inventive glucose oxidation activity at a pH of 7.4 by action of both the flavin and the haem domain. The present invention has now for the first time provided a modification of the CDH of *M. thermophilum* which has the desired glucose oxidation activity. This modification according to the present invention should now be understood in that the inventive *M. thermophilum* CDH deviates from the wild-type *M. thermophilum* CDH by the substantially increased glucose oxidation activity at a pH of 7.4. This modification can be facilitated by increasing the interaction between the flavin and the haem domains, e.g. by modifying specific key amino acids responsible for that interaction as is further described herein. Preferably increasing the interaction includes increasing contacts or interaction energy between the domains. A prediction of such modifications can be easily made by computational methods using e.g. force field based energy calculations. Furthermore, the interaction can be determined by measuring protein activity as described herein. Furthermore, it is possible to increase the pH dependency of the haem domain to a more basic pH. The pH optimum of the flavin domain of the natural CDH of *M. thermophilum* could in principle have the required pH properties to oxidise glucose, as is e.g. shown in FIG. 2f (by measurement of the 2,6-dichloroindophenol (DCIP)assay).

Also provided are enzyme preparations comprising novel CDHs. The term "enzyme" or "enzyme preparation" as used herein refers to a cellobiose dehydrogenase from a specified organism which is at least about 20% pure, preferably at least about 40% pure, even more preferably at least about 60% pure, even more preferably at least 80% pure and most preferably at least 90% pure as determined by polyacrylamide gel electrophoresis (PAGE).

BRIEF DESCRIPTION OF THE FIGURES

FIG. 1 gives the codon-optimised nucleotide sequence (SEQ ID NO: 33) and the corresponding amino acid sequence (SEQ ID NO: 1) of *Myriococcum thermophilum* CDH used for site-directed mutagenesis. Non-limiting preferred mutations sites are indicated by "*" and particular non-limiting preferred sites are marked by "+".

FIGS. 2A-2I show the pH profiles of screened ascomycete CDHs *Chaetomium* CDH. FIG. 2A shows *Corynascus thermophilus* CDH; FIG. 2B shows *Hypoxylon* haematostroma CDH; FIG. 2C shows *Neurospora crassa* CDH; FIG. 2D shows *Stachybotrys bisbyi* CDH; FIG. 2E shows *Myriococcum thermophilum* CDH; FIG. 2F shows and the genetically engineered enzyme variants *Myriococcum thermophilum* CDH variant D181K; FIG. 2G shows *Myriococcum thermophilum* CDH variant D547S/E550S; FIG. 2H shows using lactose and a soluble electron acceptor, 2,6-dichloroindophenol, (DCIP, dotted, grey lines) or cyt c (solid, black lines) as substrates and 50 mM citrate-phosphate buffer (pH 3.0-8.0); and FIG. 2I shows the relative direct electron transfer current of wild type *Myriococcum thermophilum* CDH with 5 mM glucose.

FIG. 3 is a sequence alignment of amino acid sequences of CDHs from *Chaetomium atrobrunneum* (SEQ ID NO: 5), *Corynascus thermophilum* (SEQ ID NO: 7), *Hypoxylon haematostroma* (SEQ ID NO: 3), *Myriococcum thermophilum* (SEQ ID NO: 1), *Neurospora crassa* (SEQ ID NO: 11) and *Stachybotrys bisbyi* (SEQ ID NO: 9).

DETAILED DESCRIPTION OF ILLUSTRATIVE EMBODIMENTS

Figure 4:
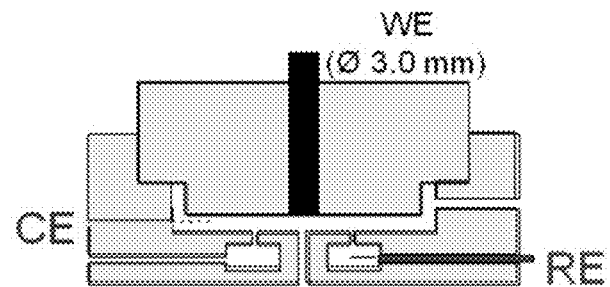
FIG. 4 shows a setup of the wall jet electrode and auxiliary instruments. The sensor assembly (A) was continuously flushed with buffer and samples were applied through an ultrafast injection valve. The obtained current at a potential of 300 mV was recorded. The flow-jet system (A) consisted of a carbon working electrode (WE), a platin counter electrode (CE) and a silver reference electrode (RE) connected to a potentiostat.

The present invention relates to cellobiose dehydrogenases isolated from novel producers or genetically engineered from existing protein scaffolds, which are able to oxidise glucose more efficiently than the currently known cellobiose dehydrogenases. The kinetic constants of the enzymes responsible for this effect are a preferably lower $K_M$ value and a higher $k_{cat}$ value for glucose than the currently characterised enzymes (e.g., *Phanerochaete chrysosporium* CDH: $K_M$=1600 mM, $k_{cat}$=2.64 s$^{-1}$, Henriksson et al., 1998, Biochimica and Biophysica Acta 1383: 48-54; *Humicola insolens* CDH: no glucose conversion detected, Schou et al., 1998, Biochemical Journal 330: 565-571; *Trametes villosa* CDH: $K_M$=1300 mM, $k_{cat}$=1.92 s$^{-1}$, Ludwig et al., 2004, Applied Microbiology and Biotechnology 64: 213-222). In addition, the $k_m$ and $k_{cat}$ values for glucose oxidation of the inventive enzymes shall be at a pH of 7.4.

In a further aspect the present invention provides a cellobiose dehydrogenase of SEQ ID NO: 5 (*Chaetomium atrobrunneum*), SEQ ID NO: 7 (*Corynascus thermophilum*), SEQ ID NO: 3 (*Hypoxylon haematostroma*), SEQ ID NO: 11 (*Neurospora crassa*) and SEQ ID NO: 9 (*Stachybotrys bisbyi*). Furthermore homologous enzymes are provided having glucose oxidation activity at a pH of 7.4 or above comprising an amino acid sequence being at least 50%, preferably at least 55%, at least 60%, at least 65%, at least 70%, at least 75%, at least 80%, at least 85%, at least 90%, at least 95%, at least 98%, in particular preferred at least 99%, identical to any one of SEQ ID NO: 3, SEQ ID NO: 5 or SEQ ID NO: 7, SEQ ID NO: 9 or SEQ ID NO: 11.

In preferred embodiments the CDH of *Chaetomium atrobrunneum* comprises an amino acid sequence of SEQ ID NO: 5. The CDH is readily available from *C. atrobrunneum* using the isolation methods described herein. In a further related aspect the present invention also provides a CDH comprising an amino acid sequence of SEQ ID NO: 5, or an amino acid sequence being at least 83%, preferably at least 85%, at least 88%, at least 90%, at least 92%, at least 93%, at least 94%, at least 95%, at least 96%, at least 97%, at least 98%, in particular preferred at least 99%, identical to SEQ ID NO: 5.

In preferred embodiments the CDH of *Corynascus thermophilum* comprises an amino acid sequence of SEQ ID NO: 7. The CDH is readily available from *C. thermophilum* using the isolation methods described herein. In a further related aspect the present invention also provides a CDH comprising an amino acid sequence of SEQ ID NO: 7, or an amino acid sequence being at least 76%, preferably at least 78%, at least 80%, at least 83%, at least 85%, at least 88%, at least 90%, at least 92%, at least 94%, at least 95%, at least 98%, in particular preferred at least 99%, identical to SEQ ID NO: 7.

In preferred embodiments the CDH of *Hypoxylon haematostroma* comprises an amino acid sequence of SEQ ID NO: 3. The CDH is readily available from *H. haematostroma* using the isolation methods described herein. In a further related aspect the present invention also provides a CDH comprising an amino acid sequence of SEQ ID NO: 3, or an amino acid sequence being at least 68%, preferably at least 70%, at least 72%, at least 74%, at least 76%, at least 78%, at least 80%, at least 80%, at least 83%, at least 85%, at least 88%, at least 90%, at least 95%, at least 98%, in particular preferred at least 99%, identical to SEQ ID NO: 3.

In preferred embodiments the CDH of *Neurospora crassa* comprises an amino acid sequence of SEQ ID NO: 11. The CDH is readily available from *N. crassa* using the isolation methods described herein. In a further related aspect the present invention also provides a CDH comprising an amino acid sequence of SEQ ID NO: 11, or an amino acid sequence being at least 72%, preferably at least 74%, at least 76%, at least 78%, at least 80%, at least 82%, at least 84%, at least 86%, at least 88%, at least 90%, at least 92%, at least 95%, at least 98%, in particular preferred at least 99%, identical to SEQ ID NO: 11.

In preferred embodiments the CDH of *Stachybotrys bisbyi* comprises an amino acid sequence of SEQ ID NO: 9. The CDH is readily available from *S. bisbyi* using the isolation methods described herein. In a further related aspect the present invention also provides a CDH comprising an amino acid sequence of SEQ ID NO: 9, or an amino acid sequence being at least 59%, preferably at least 60%, at least 62%, at least 65%, at least 70%, at least 72%, preferably at least 74%, at least 76%, at least 78%, at least 80%, at least 82%, at least 84%, at least 86%, at least 88%, at least 90%, at least 95%, at least 98%, in particular preferred at least 99%, identical to SEQ ID NO: 9.

Preferably, a homologous or modified CDH of has 1, 2, 3, 4, 5, 6, 7, 8, 9, 10, at least 11, at last 13, at least 15, at least 17, at least 20, at least 25, at least 30, at least 40, at least 50, at least 60, at least 80, at least 100 and/or up to 100, up to 80, up to 60, up to 50, up to 40, up to 30, up to 30, up to 20, up to 15 amino acid substitutions, deletions, insertions or modifications, and any ranges between these values, as compared to any one of the CDHs of SEQ ID NOs 3, 5, 7, 9 or 11.

The present invention provides novel sequences of CDHs from *Chaetomium atrobrunneum* (SEQ ID NO: 5), *Corynascus thermophilum* (SEQ ID NO: 7), *Hypoxylon haematostroma* (SEQ ID NO: 3), *Neurospora crassa* (SEQ ID NO: 11) and *Stachybotrys bisbyi* (SEQ ID NO: 9). The CDHs of these sequences, as well as homologues with at least 50% sequence identity thereto are novel CDHs which also fulfil the inventive properties of having a glucose oxidation activity at a pH of 7.4. The modification of homologous enzymes thereto with at least 50% sequence identity are preferably of amino acids which do not lower the pH requirement on the glucose oxidation activity. Any such modification can easily be tested by a glucose oxidation test on e.g. an electrode surface or by a cyt c assay, using cyt c to reoxidise the haem and subsequently the flavin domain of the CDH. Homologues can be readily identified by sequence comparisons such as by sequence alignment using publicly available tools, such as BLASTP.

The inventive CDH may be a modified CDH of *Myriococcum thermophilum*, comprising a flavin and a haem domain, wherein electron transfer from the flavin to the haem domain is increased as compared to wild type CDH of *M. thermophilum*, preferably as measured by the cyt c assay. Thus the invention relates to genetic engineering of a CDH to improve the enzymes activity further in the direction of high IET under neutral or alkaline pH conditions. The methods for the modification may be any known in the art such as amino acid mutations, including amino acid substitutions, deletions or additions but also chemical modification/derivatisation of amino acid side chains, in particular acidic amino acid side chains.

As mentioned above, the invention includes homologous sequences to the inventive CDHs of SEQ ID NOs 1 (*M. thermophilum*—with further modifications to improve the pH dependency as mentioned above), SEQ ID Nos. 3, 5, 7, 9 or 11 with at least 50%, preferably at least 55%, at least 60%, at least 65%, at least 70%, at least 75%, at least 80%, at least 85%, preferably at least 90%, at least 95%, at least 98%, or at least 99%, sequence identity to the above sequences of SEQ ID NOs 1, 3, 5, 7, 9, or 11. Preferably the catalytic site has a minimum of modifications of e.g. 1, 2, 3, 4, 5, 6, 7, 8, 9 or 10 amino acid deletions, substitutions or additions or is even exempted from modifications as compared to the wild type catalytic sites. The catalytic site is from Phe 251 to Ala 287 (Rossman Fold, flavin binding), Val 334 to Leu 345 and Met 724 to Asp 732 of the *M. thermophilum* sequence of SEQ ID NO: 1. Corresponding amino acids also exist for the CDHs of *Chaetomium atrobrunneum* (SEQ ID NO: 5), *Corynascus thermophilum* (SEQ ID NO: 7), *Hypoxylon haematostroma* (SEQ ID NO: 3), *Neurospora crassa* (SEQ ID NO: 11) and *Stachybotrys bisbyi* (SEQ ID NO: 9).

Preferably any one of the inventive CDHs shows IET (the transfer from electrons from the flavin to the haem domain) under neutral, alkaline or preferentially physiological (pH 7.4) pH conditions. To ensure a sufficiently high electrocatalytic activity of the enzyme under those conditions the IET as measured with the cyt c assay at pH 7.4 should be at least about 10% of the value maximum IET value measured under acidic pH conditions, or more preferably about 20%, or more preferably about 40%, or more preferably about 60%, or even more preferably about 80%, or most preferably should the pH optimum of IET be already neutral or alkaline.

The cellobiose dehydrogenases show preferably a sufficiently high direct electron transfer (DET) rate from the enzyme to the electrode to obtain a sufficiently high response at low substrate concentrations for a low detection limit and a high sensitivity. Only enzymes exhibiting high enough a DET current at the applied overpotential of +300 mV vs. Ag|AgCl (in 0.1 M KCl) to result in a detection limit of glucose (the lower limit of the linear range of the electrode was defined as the detection limit) with a spectrographic graphite electrode setup below 4 mM (the usual blood glucose concentration in a healthy human is 4-7 mM).

Preferably, the inventive CDH has an glucose oxidation activity at a pH of 7.4 or above and comprises an amino acid sequence of amino acids 22 to 828 of SEQ ID NO: 1 or an amino acid sequence being at least 50%, preferably at least 55%, at least 60%, at least 65%, at least 70%, at least 75%, at least 80%, at least 85%, at least 90%, at least 94%, at least 95%, at least 96%, at least 98%, in particular preferred at least 99%, identical to amino acids 22 to 828 of SEQ ID NO: 1, characterised in that the amino acid sequence has at least one additional amino acid substitution, deletion or insertion to the sequence of SEQ ID NO:1 increasing electron transfer from the flavin to the haem domain as compared to wild type CDH of *Myriococcum thermophilum* of SEQ ID NO:1, preferably as measured by the cyt c assay. Given in SEQ ID NO: 1 is the wild type *M. thermophilum* CDH which does not have the required glucose oxidation activity at a pH of 7.4. The sequence of SEQ ID NO: 1 has further a signal peptide up to amino acid 21 which may not be present on the final processed enzyme. It could now be shown that according to the present invention by a single (or more) amino acid substitution, deletion or insertion of the CDH with the final *M. thermophilum* CDH sequence the pH optimum of the glucose oxidation activity can be shifted to a more basic pH, in particular to a physiologically relevant pH of 7.4. Those skilled in the art can readily chose from possible amino acid modifications given the extensive sequence and functional information depicted herein and furthermore, can without undue burden test the modified CDH by a simple cyt c assay as described herein. Preferably, the inventive modified CDH of *M. thermophilum* has 1, 2, 3, 4, 5, 6, 7, 8, 9, 10, at least 11, at last 13, at least 15, at least 17, at least 20, at least 25, at least 30, at least 40, at least 50, at least 60, at least 80, at least 100 and/or up to 100, up to 80, up to 60, up to 50, up to 40, up to 30, up to 30, up to 20, up to 15 amino acid substitutions, deletions, insertions or modifications, and any ranges between these values.

In a further embodiment the electron transfer of the modified CDH is increased by increasing electrostatic interaction between the flavin and the haem domain, preferably at a pH of 7.4. The electrostatic interaction can be increased by optimising charge interactions at pH 7.4 of basic and acidic amino acids of the flavin and haem domain by site-directed mutagenesis, electrostatic repulsion can be reduced or electrostatic attraction increased. From the available sequence and structural information those skilled in the art can readily chose from a vast amount of such possible mutations which increase the interaction at pH 7.4, and preferably results in an increased activity in a cyt c assay.

As has been pointed out, the intramolecular electron transfer (IET) rate between the flavin domain and the haem domain depends heavily on the pH. E.g. in the basidiomycete *Trametes villosa* CDH IET is fast at pH 3.5, slows down significantly at pH 5.0, and is virtually absent above pH 6.0. Contrary, the IET of the ascomycete *H. insolens* CDH is not affected by alkaline conditions, having a pH optimum of around 8.0. From the kinetic data of *Humicola insolens* CDH an alkaline pH optimum for cyt c reduction is obvious and the DET measured for that enzyme was highest at pH>7 and is thus an exception so far for CDHs. Interestingly, although an ascomycete CDH, *Myriococcum thermophilum* CDH has an IET behaviour similar to basidiomycete enzymes. Preferably, the above amino acids are modified in the *M. thermophilum* CDH to increase the activity at a pH of 7.4 as measured in a cyt c assay. Furthermore it has been found that these amino acids are of particular interest for the activity of the enzyme. Amino acids corresponding to these amino acids in CDHs of *Chaetomium atrobrunneum*, *Corynascus thermophilus*, *Hypoxylon haematostroma*, *Neurospora crassa* or *Stachybotris bisbyi* with preferably modifications, according to the homologues to the sequences of the SEQ IDs NO: 3, 5, 7, 9 and 11 in other amino acids than in those corresponding to the above amino acids of *Myriococcum thermophilum* of SEQ ID NO: 1.

The changes in the above mentioned amino acids of SEQ ID NO: 1 in order to increase the activity at pH 7.4 are preferably to increase electrostactic interaction between the flavin and the haem domain as mentioned above.

In particular preferred embodiments the modification of the CDH is a modification of the haem domain of any one of amino acids 90-100, 115-124, 172-203, preferably of any one of amino acids 176, 179-182, 195, 196, 198, 201 corresponding to the *M. thermophilum* CDH of SEQ ID NO: 1 and/or of the flavin domain of any one of amino acids 311-333, 565-577, 623-625, 653-664, 696-723, preferably of any one of amino acids 318, 325, 326, 328, 568, 571, 574, 575, 624, 654, 663, 702, 709, 712, 717, correspond to the *M. thermophilum* CDH of SEQ ID NO: 1, or any combination thereof.

Possible modifications include (i) the exchange of acidic amino acids by neutral (polar or apolar) residues (e.g. Ser, Thr, Ala) to decrease the number of negative charges and weaken the electrostatic force field at either the haem or the flavin domain at neutral/alkaline pH values. (ii) The exchange of acidic amino acids by alkaline residues (Lys, Arg) to increase the number of positive charges and weaken the electrostatic force field at either the haem or the flavin domain at neutral/alkaline pH values, and (iii) the introduction of alkaline residues (Lys, Arg) instead of neutral residues (Hydrophobic or hydrophilic) to increase the number of positive charges and weaken the negative electrostatic force field at neutral/alkaline pH.

Particularly the modification may include an increase of positive charge in the of amino acids 172-203 corresponding to the *M. thermophilum* CDH of SEQ ID NO: 1, preferably of amino acid 181, in particular preferred a D181K mutation or D181R, and/or preferably of amino acid 198, in particular preferred a D198K or D198N mutation, and/or a decrease of a negative charge of amino acids 565-577 corresponding to the *M. thermophilum* CDH of SEQ ID NO: 1, preferably of amino acid(s) 568 and/or 571 and/or 574, in particular preferred a D568S and/or E571S mutation and/or D574S mutation, or any combination thereof, in particular the triple mutation D568S/E571S/D574S.

In further embodiments the activity of the inventive CDH is a glucose dehydrogenase activity and may be an electrocatalytic oxidation of glucose.

The inventive CDH may be isolated, in particular from *Chaetomium atrobrunneum*, *Corynascus thermophilus*, *Hypoxylon haematostroma*, *Neurospora crassa* or *Stachybotris bisbyi* or any genetically modified cell to recombinantly express the inventive CDH. Isolation may be performed by diafiltration and subsequent ion exchange chromatography by collecting fractions with CDH activity. The CDH can be further purified, e.g. using hydrophobic interaction chromatography.

The inventive CDH may also comprise a linker or be a part of a fusion protein. An inventive CDH polypeptide comprising the inventive sequences may be up to 500 kDa, up to 400 kDa, up to 300 kDa, up to 200 kDa or even up to 150 kDa.

In another aspect the present invention provides a nucleic acid molecule encoding a CDH of the invention. A preferred embodiment of the invention is a nucleic acid molecule encoding a cellobiose dehydrogenase having glucose oxidation activity at a pH of 7.4 or above and comprising a
  nucleotide sequence of SEQ ID NOs 4, 6, 8, 10 or 12, or the open reading frame of SEQ ID NOs 4, 6, 8, 10 or 12 or
  a nucleotide sequence with at least 50%, preferably at least 55%, at least 60%, at least 65%, at least 70%, at least 75%, at least 80%, at least 85%, at least 90%, at least 95%, at least 98%, in particular preferred at least 99%, identity to SEQ ID NO: 2, 33, 4, 6, 8, 10 or 12 or the open reading frame of SEQ ID NOs: 2, 33, 4, 6, 8, 10 or 12, further comprising a nucleotide mutation, substitution, deletion or insertion, preferably a codon mutation, substitution, deletion or insertion,
  a nucleotide sequence that hybridizes with any one of SEQ ID NO: 2, 33, 4, 6, 8, 10 or 12 under stringent condition.

"Stringent conditions" relate to hybridisation reactions under defined hybridisation conditions which is a function of factors as concentration of salt or formamide in the hybridisation buffer, the temperature of the hybridisation and the post-hybridisation wash conditions. Such conditions are for example hybridisation at 68° C. in a standard SSC hybridisation buffer containing 0.1% SDS followed by stringent washing in wash buffer at the same temperature. Stringent washing can be performed for example by two times washing with 2×SSC buffer followed by two wash steps with 0.5×SSC buffer. Stringent hybridisation conditions will preferably involve a temperature of 15° C. to 25° C. below the melting temperature (Tm), whereby the Tm of a hybridisation product of a nucleic acid probe can be calculated using a formula based on the g+c contained in the nucleic acids and that takes chain lengths into account, such as the formula Tm=81.5 to 16.6 (log [na$^+$])+0.41 (% G+C)−600/N), wherein N=chain length (Sambrook et al. (1989), which is incorporated herein by reference). In practice an estimated Tm for an oligonucleotide probe is often confirmed and thus a person skilled in the art can calculate the Tm for any chosen probe whose nucleotide sequence is known.

A nucleic acid sequence of *M. thermophilum* may be defined by the SEQ ID NO: 2 or 33 or the open reading frame of SEQ ID NO: 2 or 33, including homologs with at least 50%, preferably at least 55%, at least 60%, at least 65%, at least 70%, at least 75%, at least 80%, at least 85%, at least 90%, at least 95%, at least 98%, in particular preferred at least 99%, identity to SEQ ID NO: 2 or 33 or the open reading frame of SEQ ID NO: 2 or 33, further comprising a codon mutation, substitution, deletion or insertion to encode a CDH with glucose oxidation activity at a pH of 7.4 or above, preferably of amino acids 22 to 828 of SEQ ID NO: 1 with an additional amino acid substitution, deletion or insertion. Preferably the encoded CDH is of the amino acid sequence with the above mentioned amino acid modification.

The inventive nucleic acid molecules encoding a CDH with glucose oxidating activity at pH 7.4 may be isolated or purified. The inventive nucleic acid molecules, in particular their open reading frame may be comprised in a vector, preferably an expression or cloning vector. An inventive nucleotide molecule might further contain regulatory elements such as promotors and enhancers. Such a nucleic acid molecule comprising the inventive sequences may consist of up to 1,000,000 nucleotides, up to 900,000 nucleotides, up to 800,000 nucleotides, up to 700,000 nucleotides, up to 600,000 nucleotides, up to 500,000 nucleotides, up to 400,000 nucleotides, up to 300,000 nucleotides, up to 200,000 nucleotides, up to 100,000 nucleotides, up to 50,000 nucleotides or up to 25,000 nucleotides.

Particular benefits of the inventive CDHs are i) a high glucose turnover rate, ii) sufficient activity of the flavin domain and IET at pH 7.4 and iii) good DET characteristics. It was further found that these CDHs and other known CDHs are in particular suitable as anodic material in a bioelectrode as e.g. biosensor or biofuel cell.

One approach was to identify CDHs of different fungal strains from the phylum of ascomycota. It was found that some CDHs, e.g. from *Chaetomium atrobrunneum*, *Corynascus thermophilus*, *Hypoxylon haematostroma*, *Neurospora crassa* or *Stachybotris bisbyi* are able to convert glucose with high turnover rates at pH 7.4 and have additionally very good DET properties. Some of the found CDHs are new per se as mentioned above. A further aspect of the present invention is the use of all CDHs described herein on an electrode, in an electrochemical cell, in particular in a biosensor to measure glucose, preferably at a physiological pH such as pH 7.4.

Furthermore it was found that CDH from *M. thermophilum*, which is known to oxidise glucose and have good DET properties but shows no IET at pH values above pH 7.0, can be genetically engineered to increase the pH range of the IET to more alkaline conditions by means of site-directed mutagenesis. These CDHs were particularly suitable for electrochemical devices.

Thus, in a further aspect the present invention provides an electrode comprising an immobilised CDH having glucose oxidation activity at a pH of 7.4 or above and having at least 10%, at least 12%, at least 14%, at least 16%, preferably at least 18%, at least 19%, in particular preferred at least 20%, at least 21%, or even at least 22%, at least 23%, at least 24%, at least 25%, at least 26%, at least 27%, at least 28%, at least 29% or at least 30% glucose, lactose or cellobiose oxidising activity at a pH of 7.4 as compared to their maximal activity at a lower pH as determined by the cyt c assay. Preferably the immobilised CDH also has a glucose oxidation activity at a pH of 7.4 or above and having at least 10%, at least 12%, preferably at least 18%, at least 19%, in particular preferred at least 20%, at least 21%, or even at least 22%, at least 23%, at least 24%, at least 25%, at least 26%, at least 27%, at least 28%, at least 29% or at least 30%, glucose, lactose or cellobiose oxidising activity at a pH of 7.4 as compared to their maximal activity at a lower pH as determined by a 2,6-dichloroindophenol (DCIP) assay. An electrode is generally a conducting surface, e.g. suitable for an electrochemical element.

The activity measurement by either the cyt c or DCIP assay can be readily facilitated in a model system. The CDH can be directly used with the substrate (glucose but also lactose or cellobiose) and a reoxidising agent being either cyt c for reoxidation at the haem domain or DCIP for reoxidation at the flavin domain. The CDH is tested at a pH of 7.4 in any suitable buffer, e.g. a potassium or natrium phosphate buffer. To determine the maximum of the CDH activity, the activity is continuously measured at different pH values, e.g. ranging from pH 3 to pH 7.4 or higher and determining the maximum activity. The pH of 7.4 is then compared with this maximum activity and should have the required activity fraction mentioned above. The activity can e.g. be given as absolute values in U/mg or as relative values. Preferably, the inventive CDH has the required activity portion as compared to the maximum activity in both a cyt c and a DCIP assay. These activity values preferably also apply to the new CDHs described above, as such, independent of their fixation on an electrode. Preferably, the assay to determine the inventive CDH on the electrode is performed by glucose oxidation. Alternatively, also using lactose is possible.

The electrode may be of any material suitable to immobilise the CDH, e.g. carbon such as graphite, glassy carbon, boron doped diamond, gold electrodes modified with promoters e.g., thiols, screen-printed electrodes, screen printed electrodes containing carbon nanotubes (single or multiwalled). It may contain other nanoparticles to increase the specific surface area. Particular uses of the inventive electrodes are in the provision of biosensors and enzymatic biofuel cells, more specifically to glucose biosensors and glucose oxidizing biofuel cell anodes using the direct electron transfer properties (DET) of cellobiose dehydrogenase (CDH) to measure the glucose concentration at neutral, alkaline or, preferentially, physiological pH (in human body fluids, e.g., 7.4 in blood) or use glucose for the generation of an electric current in biofuel cells under the same pH conditions.

In particular preferred embodiments the specific activity for glucose oxidation by using the cyt c assay at pH 7.4 is higher than 0.5 U/mg, preferably at least 0.6 U/mg, at least 0.7 U/mg, at least 0.8 U/mg, at least 0.9 U/mg, at least 1 U/mg, or at least 1.2 U/mg CDH, or a current density higher than 80 nA/cm$^2$ at pH 7.4.

In further preferred embodiments the apparent $K_M$ value of the CDH for glucose in solution (DCIP assays at optimum activity) is lower than 1.7 M, preferably lower than 1.5, lower than 1.2, preferably lower than 1 M or, when measured on electrodes an apparent $K_M$ value below 200 mM, preferably below 150 mM.

In another embodiment the present invention provides an electrode, wherein the CDH is of *Chaetomium atrobrunneum, Corynascus thermophilus, Hypoxylon haematostroma, Neurospora crassa* or *Stachybotris bisbyi* or a modified CDH of *Myriococcum thermophilum* with an increased activity at pH of 7.4 as defined in above, or homologues with certain sequence identities, amino acid modifications, etc. as defined above.

On the electrode, the CDH may be immobilised by adsorption, preferably also physical entrapment, complex formation, preferably via an additional complexing linker, covalent binding, in particular cross linking, or ionic linkage and/or the immobilized cellobiose dehydrogenase can be cross-linked, in particular by bifunctional agents, to increase stability or activity. It has been shown that crosslinking with bifunctional agents, such as agents with two reactive groups making a connection with the CDH, can stabilize the CDH and even increase its activity on graphite electrodes measurable by amperometric methods described herein. This advantage can lead to an increased sensitivity and lowering the detection limit for glucose. Such a crosslinking agent is e.g. glutaraldehyde or any other dialdehydes.

The electrodes might be used in form of a single electrode or electrode stacks. More specifically, the application of these enzymes is in (bio)electrochemical devices such as glucose biosensors or biofuel cells anodes. The electrode may be used as biosensor or as biofuel cell anode.

In another aspect the present invention provides an electrochemical cell comprising an electrode as described above as an anodic element and a cathodic element.

In preferred embodiments of the electrochemical cell the anodic fluid can be glucose containing solution. Preferably the electrode is suitable for measurement in blood, serum and other body fluids.

The electrochemical cell may further comprise a solution of at least pH 6.0, preferably at least pH 6.5 or at least pH 6.7, in particular preferred at least pH 7.0, even more preferred at least pH 7.1, or at least pH 7.2, or at least pH 7.3, especially preferred at least 7.4, as anodic fluid.

According to another aspect a method of detecting or quantifying glucose in a sample is provided comprising
    providing a CDH having glucose oxidation activity at a pH of 7.4 or above,
    contacting a fluid sample having a pH of at least 6.0, preferably at least 6.5, or at least 6.7, more preferred at least 7.0, at least 7.1, at least 7.2, in particular preferred at least 7.3, especially preferred at least 7.4, with the CDH, and
    detecting an oxidation of glucose of the sample by the CDH.

Preferably the oxidation is detected electrochemically, preferably with an immobilised CDH on an electrode, in particular preferred as defined above.

One of the world-wide leading causes of death and disability is diabetes. The diagnosis and management of diabetes mellitus requires continuous monitoring of blood glucose levels. Amperometric enzyme electrodes, based on glucose oxidase, play an increasingly important role and have been a target of substantial research. Most sensors are used for individual, daily diabetes monitoring, but the demand for continuous in vivo monitoring of patients is also significant. Real-time measurements are highly desired in intensive care units, during surgery, or for the management of diabetes, where rapid biochemical changes can be missed by discrete measurements. Such monitoring requires miniaturized, biocompatible, and stable sensors. Although research has reached the level of short-term implantation, an implantable glucose sensor possessing long-term stability has not yet been realised. Besides the obvious biocompatibility challenge, some sensors are prone to errors due to low oxygen tension or electroactive interferences. Third generation biosensors depend on enzymes that are able to permit direct electron transfer (DET) between the electrode material and the redox active centre. Usually this is hindered by the encapsulation of the redox center by the protein structure. However, as has been shown herein, the inventive CDH can exhibit electrical communication with electrode supports.

In certain embodiments the CDH has at least 10%, or at least 12%, preferably at least 14%, or at least 16%, in particular preferred at least 18%, or at least 20%, at least 21%, or even at least 22%, at least 23%, at least 24%, at least 25%, at least 26%, at least 27%, at least 28%, at least 29%, or at least 30%, glucose, lactose or cellobiose oxidising activity at a pH of 7.4 as compared to the maximal activity at a pH below 7.4 as determined by a cyt c assay and/or DCIP assay.

The fluid sample may be any fluid which potentially comprises glucose, including blood, serum and other body fluids.

In particularly preferred embodiments the CDH is of *Chaetomium atrobrunneum, Corynascus thermophilus, Hypoxylon haematostroma, Neurospora crassa* or *Stachybotris bisbyi* or a modified CDH of *Myriococcum thermophilum* with an increased activity at pH of 7.4 as defined above.

The cellobiose dehydrogenase of the present invention may be obtained from microorganisms of any genus. For purposes of the present invention the term "obtained from" as used herein in connection with a given source shall mean that the enzyme is produced by the source or by a cell in which the nucleic acid sequence of the cellobiose dehydrogenase gene from the source has been inserted. The enzyme or its nucleic acid sequence may be obtained from any fungal source and in a preferred embodiment from the genus *Chaetomium, Corynascus, Hypoxylon, Myriococcum, Neurospora* or *Stachybotrys*. In a more preferred embodiment the enzymes or the nucleic acid sequences are obtained from the species *Chaetomium atrobrunneum, Corynascus thermophilus, Hypoxylon haematostroma, Myriococcum thermophilum, Neurospora crassa* or *Stachybotrys bisbyi*.

In the most preferred embodiment the enzymes or the nucleic acid sequences are obtained from the strains *Chaetomium atrobrunneum* CBS 238.71, *Corynascus thermophilus* CBS 405.69, *Hypoxylon haematostroma* CBS 255.63, *Myriococcum thermophilum* CBS 208.89, *Neurospora crassa* DSMZ 2968 or *Stachybotrys bisbyi* DSMZ 63042.

It will be understood that for the aforementioned species, the invention encompasses both the perfect and imperfect states and other taxonomic equivalents, e.g., anamorphs, regardless the species name by which they are known. Those skilled in the art will readily recognise the identity of appropriate equivalents.

It is understood that one of skills in the art may engineer the mentioned or other cellobiose dehydrogenases to obtain the outlined specifications of the enzymes and enzyme variants described herein to obtain modified enzymes using the principles outlined herein like the rational approach via site-directed mutagenesis or directed evolution approaches (e.g., gene shuffling, error-prone PCR) and subsequent screening of the generated diversity. The techniques to introduce a mutation into the nucleic acid sequence to exchange one nucleotide for another nucleotide with the aim to exchange one amino acid for another in the resulting protein may be accomplished by site-directed mutagenesis using any of the methods known in the art.

The present invention is further illustrated by the following figures and examples without being restricted thereto.

EXAMPLES

Example 1: Materials

Chemicals used in buffers and fermentation media were commercial products and at least of analytical grade if not otherwise stated. Peptone from meat and microcrystalline cellulose were from VWR International (Vienna, Austria), alpha-cellulose from Sigma-Aldrich (Vienna, Austria). Substrates for kinetic studies were lactose, glucose, 2,6-dichloroindophenol (DCIP) and cytochrome c from horse heart (cyt c) from Sigma-Aldrich in the highest grade of purity available. Buffers were prepared using water purified and deionised (18 MΩ) with a Milli-Q system (Millipore, Bedford, Mass., USA), fermentation media contained reversed osmosis water (0.1 MΩ).

Example 2: Enzyme Assays

Enzymatic activity of cellobiose dehydrogenase was detected by two assays. The DCIP assay, measuring the activity of the flavin domain was performed by measuring the time-dependent reduction of 300 µM DCIP in 50 mM citrate-phosphate buffer at the indicated pH (3.0-8.0), containing 30 mM lactose at 520 nm and 30° C. The absorption coefficient for DCIP is pH dependent but differs at 520 nm only about 3% within pH 3.0 to 8.0 and was determined to be 6.8 mM$^{-1}$ cm$^{-1}$ (Karapetyan et al., 2005 Journal of Biotechnology 121: 34-48).

Alternatively, enzymatic activity was determined by the reduction of cytochrome c at 30° C. and 550 nm (cyt c, $\varepsilon_{550}$=19.6 mM$^{-1}$ cm$^{-1}$, Canevascini et al., 1991, European Journal of Biochemistry 198: 43-52) in an assay containing 20 µM cyt c and 30 mM lactose, which specifically detects the activity of the whole enzyme (flavin and haem domain). The cyt c assay gives thereby also a measure of the efficiency of the intramolecular electron transfer (IET) between both domains as an indication of the enzyme's response on electrodes in a pH range of 3.0 to 8.0 (50 mM sodium citrate-phosphate buffer). For the detection of activity with glucose the above mentioned assays were used, but lactose was exchanged for 100 mM glucose.

One unit of enzymatic activity was defined as the amount of enzyme that oxidises 1 µmol of lactose per min under the assay conditions. Lactose was chosen instead of the natural substrate cellobiose, as it shows no substrate inhibition with CDH. The reaction stoichiometry with carbohydrates is 1 for the two-electron acceptor DCIP, but 2 for the one-electron acceptor cyt c.

Example 3: Enzyme Kinetics

Carbohydrate stock solutions used for measuring activity and kinetic constants with the DCIP and cyt c assays were prepared in the appropriate buffer several hours before the experiment to allow mutarotation to reach equilibrium. pH profiles were determined using 50 mM citrate-phosphate buffer (3.0-8.0). To ensure an assay temperature of 30° C. the cuvettes were incubated in a thermostated chamber for at least 20 min. After the measurement, the pH was again checked in the cuvettes. Kinetic constants were calculated by fitting the observed data to the Henri-Michaelis-Menten equation or to the adapted model for substrate inhibition using nonlinear least-squares regression and the program SigmaPlot (Systat Software, San Jose, CF, USA).

Example 4: Protein Characterisation

The protein concentration was determined by the dye-staining method of Bradford using a pre-fabricated assay from Bio-Rad Laboratories Hercules, Calif., USA) and bovine serum albumin as standard according to the manufacturers recommendations.

For spectral characterisation apparently homogeneous CDH (in the oxidised state) was diluted to an absorption of ~1 at 280 nm and the spectrum from 260 to 700 nm taken with an Hitachi U3000 spectrophotometer (Tokyo, Japan). After reduction with lactose (final concentration 1 mM) the reduced spectrum was taken.

For electrophoretic characterisation SDS-PAGE was carried out on a Hoefer SE 260 Mighty Small II vertical electrophoresis unit. Gels (10.5×10 cm; 10% T, 2.7% C) were cast and run according to the manufacturers' modifications of the Laemmli system. Isoelectric focusing in the range of pH 2.5 to 6.5 was performed on a Multiphor II system using precast, dry gels rehydrated with Ampholytes (GE Healthcare Biosiences, Vienna, Austria). Protein bands on the SDS-PAGE were stained with silver, bands on the IEF gel with Coomassie blue R-250, according to the instructions.

Example 5: Screening for Suitable Cellobiose Dehydrogenases

Fungal strains (*Chaetomium atrobrunneum* CBS 238.71, *Corynascus thermophilus* CBS 405.69, *Hypoxylon haematostroma* CBS 255.63, *Myriococcum thermophilum* CBS 208.89, *Neurospora crassa* DSMZ 2968 and *Stachybotrys*

*bisbyi* DSMZ 63042) were obtained from the Centraalbureau voor Schimmelcultures (CBS, Utrecht, The Netherlands) and Deutsche Sammlung von Mikroorganismen und Zellkulturen (DSMZ, Braunschweig, Germany) in freeze dried or actively growing form on agar slants and were periodically subcultured on potato dextrose agar (PDA) plates. Freshly inoculated agar plates were grown at 25 or 30° C., depending on the published growth temperatures of the cultures until reaching a diameter of 5 cm and then used to inoculate shaking flasks. The medium used for submersed cultures contained (per liter): 20 g of alpha-cellulose, 5 g of peptone from meat and 0.3 ml of a trace element solution. The trace element solution contained (per liter): 1 g of $ZnSO_4 7H_2O$, 0.3 g of $MnCl_2 4H_2O$, 3 g of $H_3BO_3$, 2 g of $CoCl_2 6H_2O$, 0.1 g of $CuSO_4 5H_2O$, 0.2 g of $NiCl_2 6H_2O$, 4 ml of $H_2SO_4$ (Sachslehner et al., 1997, Applied Biochemistry and Biotechnology 6365: 189-201). For the cultivation in shaking flasks, 1 L Erlenmeyer flasks were filled with 0.3 L of medium. After sterilisation the flasks were inoculated with 3 $cm^2$ of finely cut mycelium from PDA plates and incubated in a rotary shaker (110 rpm, eccentricity=1.25 cm) at 25 or 30° C. Samples were taken regularly and the production of CDH was monitored.

Example 6: CDH Production and Purification from Fungal Sources

CDH production was performed in up to 16 parallel shaking flask cultures per strain using identical conditions as in the screening procedure. Cultures were harvested on the day exhibiting maximum cyt c activity. The culture supernatant was separated from residual cellulose and fungal biomass by centrifugation (20 min, 6000×g) and concentrated and diafiltrated using a polyethersulfone hollow fibre cross-flow module with a 10 kDa cut-off (Microza UF module SLP-1053, Pall Corporation) until a conductivity of 2 mS $cm^{-1}$ was reached. The concentrated enzyme preparation was applied to a DEAE Sepharose column (chromatography equipment from GE Healthcare Biosciences) mounted on an ÄKTA Explorer system and equilibrated with 50 mM sodium acetate buffer, pH 5.5. The column was eluted with a linear salt gradient (0 to 0.5 M NaCl in the same buffer) in 10 column volumes (CV). Fractions with a high specific CDH activity were pooled, saturated ammonium sulphate solution was slowly added at 4° C. to 20% final saturation and applied to a PHE-Source column equilibrated with 100 mM sodium acetate buffer, pH 5.5 containing $(NH_4)_2SO_4$ (20% saturation) and 0.2 M NaCl. The column was eluted with a linear gradient (0 to 100% of 20 mM sodium acetate buffer, pH 5.5) in 10 CV. The purest CDH fractions were pooled, desalted with 20 mM sodium acetate buffer, pH 5.5, concentrated and frozen at −70° C. for further use.

Example 7: Obtaining Nucleotide and Protein Sequences of New CDHs

Mycelium for nucleic acid isolations was harvested from cellulose induced growing cultures after 5 days. The mycelium was frozen in liquid nitrogen and homogenized using mortar and pestle. Portions of 100 mg mycelium were used for DNA extraction (Liu et al., 2000, Journal of Clinical Microbiology, 38: 471). Total RNA was isolated using TriFast (Peqlab, Erlangen, Germany). cDNA synthesis was performed with the First Strand cDNA Synthesis Kit (Fermentas, Vilnius, Lithuania) and the anchor primer (5'-GGC-CACGCGTCGACTAGTACTTTTTTTTTTTTTT-3').
Degenerated primer on the basis of known ascomycete CDH sequences were used to amplify fragments of genomic DNA encoding for CDH. For the amplification of the adjacent upstream region the DNA Walking SpeedUp Premix Kit (Seegene, Seoul, Korea) was used. For the amplification of the 3' region cDNA was used as a template. To obtain full-length cDNA clones encoding the CDH proteins a nested PCR with two specific forward primer upstream of the putative start codon and two reverse primer, one specific for a sequence shortly downstream of the stop codon and the universal primer (5'-GTACTAGTCGACGCGTGGCC-3') complementary to the anchor primer, was done. Names in the following primer table are abbreviated as follows: *Chaetomium atrobrunneum*, CA; *Corynascus thermophilus*, CT; *Hypoxylon haematostroma*, HH; *Neurospora crassa*, NC; *Stachybotrys bisbyi*, SB.

| | forward primer | | reverse primer |
|---|---|---|---|
| 5'-HH-1 | atgcctctcttgtttggaccg | Universal | |
| 5'-HH-2 | tcaactctcatacttggcttgg | 3'-HH-1 | TACATCCAGCTTACCGGCACTG |
| 5'-CA-1 | TAGAGTCGAGGCGAACCAG | UNIVERSAL | |
| 5'-CA-2 | TTGCTGCTGTGCTCCTATGC | 3'-CA-1 | ttccttccctccatcaactcc |
| 5'-SB-1 | tcttgctacgcacttcggtattg | Universal | |
| 5'-SB-2 | TGTGTACCCTGTTTACTCACC | 3'-SB-1 | GTACCCATTAAGTACACTGCCAG |
| 5'-CT-1 | TCTTATAAGCCTTTGGCTCC | Universal | |
| 5'-CT-2 | TTGGCTCCGTTGGAACAATG | 3'-CT-1 | TTCCCCCTTCGAATTCGGTC |
| 5'-NC-1 | cgcaccaaccgtgtgaagtg | Universal | |
| 5'-NC-2 | TACAAGATGAGGACCACCTCG | 3'-NC-1 | AGCTACCTATCACCCTCTGTC |

The obtained PCR products were then fully sequenced to obtain the complete nucleic acid sequence of the respective cdh gene.

Example 8: Generation of *Myriococcum thermophilum* CDH Variants by Site-Directed Mutagenesis For enhanced production of recombinant *Myriococcum thermophilum* CDH (Zamocky et al., 2008,) in *Pichia pas-*

*toris* the gene (gene bank accession code EF 492052, GI:164597963) was codon optimised (FIG. 1) for expression in *P. pastoris* and synthesized by GenScript (Piscataway, N.J., USA). The gene shows a maximum similarity with CDH from *Thielavia heterothallica* (74% identity) and only 63% identity with the gene from *Humicola insolens*. On the protein level, the similarity is highest to *Thielavia heterothallica* CDH (93% identity, 97% positives, 0% gaps) and quite low for *Humicola insolens* CDH (61% identity, 71% positives, 2% gaps).

The synthetic *M. thermophilum* CDH gene was mutated by a two-step site-directed mutagenesis protocol using PCR and DpnI digestion. The yeast vector pPICZ A carrying the synthetic CDH gene was used as template for mutagenic PCR. For the replacement of Asp160 with Lys the primers 5'-TCCAAGCTTTTAAAGATCCAGGTAAC-3' (Mt CDH-D181K-fw) and 5'-AAAAGCTTGGACCCAACCAAG-3' (Mt CDH-D181K-rv) were used. For the double mutant D547S/E550S primers 5'-GTCTTCTATTCTTTTTACTCTGCTTGGGATG-3' (Mt CDHD547S/E550S-fw) and 5'-ATAGAAGACCACATCAGGG-3' (Mt CDH-D547S/E550S-rv) were used. The mutation sites are indicated by bold letters in the mutagenic forward primers. PCR was performed under the following conditions: 98° C. for 30 s, then 32 cycles of 98° C. for 10 s; 62° C. for 20 s; 72° C. for 2 min, with a 10 min final extension at 72° C. The 50 µl reaction mix contained Phusion HF Buffer (New England Biolabs, Ipswich, Mass., USA), 0.1 µg of plasmid DNA, 1 unit of Phusion DNA polymerase (New England Biolabs), 10 µM of each dNTP and 5 pmol of each primer.

PCR reactions were separated by agarose gel electrophoresis and bands at 6 kB purified using the Wizard SV Gel and PCRClean-Up System (Promega, Madison, Wis., USA). The purified PCR fragment was digested with DpnI (Fermentas, Vilnius, Lithuania) to remove methylated DNA. 10 µl of this reaction was used to transform chemically competent NEB-5-Alpha *E. coli* cells (New England Biolabs) according to the manufacturer. For each mutation 3 colonies were checked by sequencing for the presence of the correct mutation. The purified plasmid of a positive clone was linearized with SacI and used to transform competent X-33 *P. pastoris* cells. Colonies growing on YPD zeocin agar plates (100 mg/L) were checked by PCR for the integration of the construct. Two positive clones of each mutation were further cultivated under induced condition and analysed for CDH production. The clones with the highest yield were selected for fermentation.

Example 9: Production of Recombinant CDH

An overnight pre-culture of a *Pichia pastoris* transformant (selected from a YPD plate with 100 mg/L Zeocin) was inoculated into 0.3 L of production stage medium in a Infors HT multifermenter (Bottmingen, Switzerland). The production stage medium contained per liter: 26.7 ml of $H_3PO_4$ (85%); 0.93 g of $CaSO_4.2H_2O$; 14.9 g of $MgSO_4.7H_2O$; 18.2 g of $K_2SO_4$; 4.13 g of KOH; 4% (v/v) glycerol; 1.45 ml of $PTM_1$ trace element solution for *P. pastoris* according to the Invitrogen manual 053002 Ver. B (Carlsbad, CF, USA). The $PTM_1$ trace element solution contains per liter: 6 g of $CuSO_45H_2O$, 0.08 g of NaI, 3 g of $MnSO_4H_2O$, 0.2 g of $NaMoO_4.2H_2O$, 0.02 g of $H_3BO_3$, 0.5 g of $CoCl_2$, 20 g of $ZnCl_2$, $FeSO_47H_2O$, 0.2 g of biotin, 5 ml of sulfuric acid. A glycerol feed was performed with an addition of 9 $gL^{-1}$ $h^{-1}$ until the wet cell weight exceeded 150 g per liter. As soon as the residual glycerol was used up (determined by monitoring the increase of the dissolved oxygen tension), a methanol feed (100% methanol containing 12 ml $PTM_1$ trace element solution per liter) with an average addition of 3 $gL^{-1}$ $h^{-1}$ was started and continued for 72 h at 30° C. and 20% oxygen tension. The culture supernatant was separated from residual biomass by centrifugation (20 min, 6000×g) and concentrated and purified by hydrophobic interaction chromatography. To that purpose, saturated ammonium sulphate solution was slowly added to the clear culture supernatant at 4° C. to 20% final saturation. After a second centrifugation step (30 min, 30,000×g) the solution was applied to a PHE-Source column (GE Healthcare Biosciences) equilibrated with 100 mM sodium acetate buffer, pH 5.5 containing $(NH_4)_2SO_4$ (20% saturation) and 0.2 M NaCl. The column was eluted with a linear gradient (0 to 100% of 20 mM sodium acetate buffer, pH 5.5) in 10 CV. The purest CDH fractions were pooled, desalted with 20 mM sodium acetate buffer, pH 5.5, concentrated and stored for further use.

Example 10: Electrochemical Equipment

A three electrode flow through amperometric wall jet cell was used (Appelqvist et al, *Anal. Chim. Acta,* 169 (1985) 237-47.) and contained the working electrode (graphite electrode modified with CDH), a reference electrode (Ag☐AgCl in 0.1 M KCl) and a counter electrode made of a platinum wire, connected to a potentiostat (Zäta Elektronik, Höör, Sweden). The enzyme modified electrode was pressfitted into a Teflon holder and inserted into the wall jet cell and kept at a constant distance (ca. 1 mm) from the inlet nozzle. The response currents were recorded on a strip chart recorder (Kipp & Zonen, Delft, The Netherlands). The electrochemical cell was connected on-line to a single line flow injection (FI) system, in which the carrier flow was maintained at a constant flow rate of 0.5 ml $min^{-1}$ by a peristaltic pump (Gilson, Villier-leBel, France). The injector was an electrically controlled six-port valve (Rheodyne, Cotati, Calif., USA), and the injection loop volume was 50 µl.

For the screen-printed electrodes a special methacrylate wall jet flow for flow injection analysis (FIA) from DropSense (Oviedo, Spain) was used. The electrochemical cell consists of a carbon working electrode (4 mm diameter), a carbon counter electrode and silver reference electrode connected to a potentiostat (Zata Elektronic). The response currents were recorded on a strip chart recorder (Kipp & Zonen). The electrochemical cell was connected on-line to a single flow injection (FI) system, in which the carrier flow was maintained at a constant flow rate of 0.5 ml $min^{-1}$ by a peristaltic pump (Gilson). For injection an electronically controlled six-port valve (Rheodyne) and a injection loop (50 µl) was used.

Example 11: Preparation of Enzyme Modified Graphite Electrodes

CDH was immobilised through simple chemo-physical adsorption onto the surface of solid spectroscopic graphite electrodes (diameter=3.05 mm, Ringsdorff Spektralkohlestäbe, SGL Carbon Sigri Greatlakes Carbon Group Ringsdorff-Werke GmbH, Bonn Germany). The electrode was cut and polished on wet emery paper (Tufbak, Durite, P400) and afterwards carefully rinsed with Milli-Q water and dried. Then 5 µl of enzyme solution was spread onto the entire active surface of the electrode (0.0731 $cm^2$). The electrode was dried at room temperature and then stored overnight at 4° C. Before use, the electrode was thoroughly rinsed with Milli-Q water in order to remove any weakly adsorbed enzyme and plugged into in the wall jet cell already containing buffer. Then, the required potential was applied until a stable background current was obtained before any substrate was injected into the flow system.

Example 12: Preparation of Enzyme-Modified Screen Printed Electrodes

Five µl of enzyme solution was placed on the carbon-based electrode (DropSens, Oviedo, Spain) so that the whole area was entirely coated with solution. The immobilisation was allowed to proceed overnight at 4° C. Before use the electrodes were thoroughly rinsed with water. Cross-linking of the biocomponent was carried out by chemical modification with glutaraldehyde where 1 µl of an aqueous 1% glutaraldehyde solution was applied on the enzyme layer at 37° C. for 10-15 min. After rinsing the electrodes were allowed to dry at room temperature.

The optimum for the applied potential was determined with a 10 mM lactose solution. The potential was varied stepwise from −250 to +600 mV vs. Ag|AgCl in 0.1 M KCl and +300 mV chosen for further experiments.

Example 13: pH Profiles of CDH Immobilised on Electrodes

The activity versus pH-profile for direct electron transfer (DET) of the adsorbed enzyme was determined electrochemically using a flow injection system. The substrate was lactose with a concentration of 5 mM. As enzyme assays should proceed under saturating substrate conditions so that slight variations in the absolute concentration have no influence on the reaction rate an amount at least 10 times the $K_M$-value should be present. The following buffers were used in the experiments: 50 mM sodium citrate buffer (pH 3.0-6.5), 50 mM sodium phosphate buffer (pH 6.0-9.0). The buffers were degassed before use to prevent micro bubbles in the flow system.

Example 14: Heterogeneous Enzyme Kinetics on Electrodes

Figure 5:
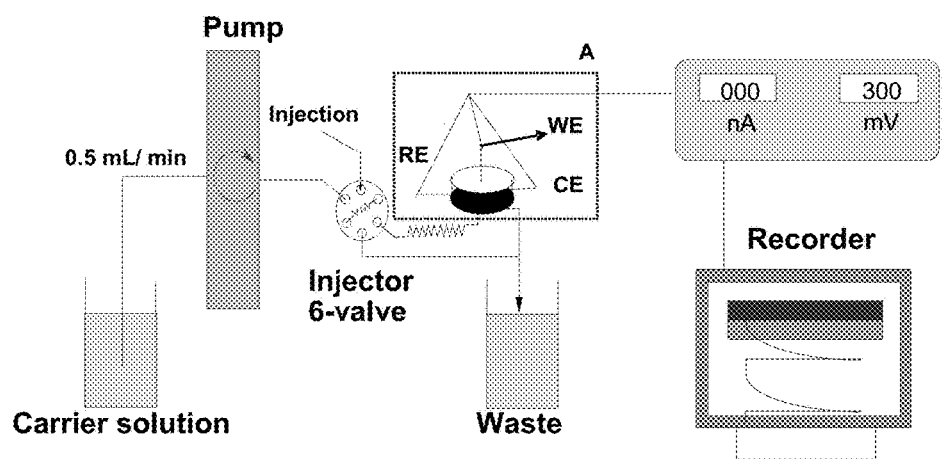
FIG. 5: Measurement setup of the flow-cell system

The kinetic parameters $K_M$ (Michaelis-Menten constant) and $v_{max}$ (maximum volumetric activity), in this case equal to $I_{max}$ (maximum response in current), were determined for a number of substrates in the DET mode (the electron acceptor being the graphite electrode). All kinetic parameters were calculated by nonlinear least-square regression, fitting the observed data to the Henri-Michaelis-Menten equation. These calculations were done after correcting the substrate concentration values using the dispersion factor of the flow system used including the wall jet cell by dividing the steady state current registered for a 50 mM ferrocyanide solution with that of the peak current for the injected sample having an equal concentration of ferrocyanide and using an applied potential of 400 mV (Ruzicka and Hansen, Flow Injection Analysis, 2nd ed., Wiley, New York 1988). In our case, for a 1 mm distance between electrode and inlet nozzle and 0.5 ml min$^{-1}$ flow rate, the dispersion factor D was equal to 1.18 (FIG. 5).

Example 15: CDH of Chaetomium atrobrunneum

A cellobiose dehydrogenase with high glucose turnover rates and activity under physiological pH conditions was obtained from liquid cultures of Chaetomium atrobrunneum. The culture was grown and screened as described. The maximum activity under the chosen conditions was 90 U/L (cyt c assay, pH 6.0, 11$^{th}$ day). For enzyme production and purification the outlined procedures were applied and resulted in an CDH preparation with a specific activity of 11.7 U/mg (DCIP assay, pH 6.0), an apparent molecular weight of 90 kDa as determined by SDS-PAGE and an isoelectric point of 4.6. The calculated molecular weight of the obtained protein sequence is 86.047 kDa and fits well to the native CDH. The calculated isoelectric point is 5.0. The spectrum of Chaetomium atrobrunneum CDH is typical and shows the haem alpha-, beta- and gamma-bands of the reduced enzyme at 563, 533 and 430 nm. In the oxidised enzyme the gamma-band has its absorption maximum at 421 nm with a shoulder at 450 nm, which disappears after reduction with lactose and corresponds to the absorption peak of the FAD cofactor. Kinetic characterisation with the cyt c assay and lactose as electron donor resulted in a neutral pH profile with an activity maximum at pH 5.0 and still 18% relative activity at pH 7.4 (FIG. 2.a). The specific activity at pH 7.4 was 0.88 U/mg using the cyt c assay and glucose as substrate. The pH optimum of the flavin domain was obtained with the DCIP assay and shows a more acidic pH optimum, however, the flavin domain is sufficiently active at pH 7.4 also with this electron acceptor. Kinetic constants for glucose (obtained with the cyt c assay at pH 5.0) are a $K_M$ of 240 mM and $k_{cat}$ of 17.5 s$^{-1}$ for glucose, which shows in comparison to currently known enzymes a far better suitability of this enzyme for the proposed application.

To test the electrochemical behaviour of Chaetomium atrobrunneum CDH on electrodes, the purified enzyme preparation was immobilised by adsorption on a spectroscopic graphite electrode surface. Using a flow cell and subsequent injections of 50 mM glucose, DET currents were determined to determine the pH optimum, the current at the pH optimum and the current at pH 7.4. The optimum pH under the chosen conditions is 5.6 and 48% of the maximum current was obtained at pH 7.4 in 10 mM phosphate buffered saline (PBS) containing 100 mM NaCl. The $K_M$ value of the heterogenised enzyme at optimum pH on the electrode surface was determined to be 80 mM and $I_{max}$=30 nA. The currents obtained in glucose measurements should therefore follow a nearly linear relationship for concentrations approx. five-fold below the $K_M$ value. The DET current density obtained at pH 7.4 was 233 nA/cm$^2$ and the linear range for glucose detection at pH 7.4 with the chosen setup within 3-15 mM.

Example 16: CDH from Corynascus thermophiles

A cellobiose dehydrogenase with high glucose turnover rates and activity under physiological pH conditions was obtained from liquid cultures of Corynascus thermophilus. The maximum activity obtained was 1400 U/L (cyt c assay, pH 6.0, 6$^{th}$ day). For enzyme production and purification the outlined procedures were applied and resulted in a CDH preparation with a specific activity of 17.9 U/mg, an apparent molecular weight of 87 kDa as determined by SDS-PAGE and an isoelectric point of 4.1. The calculated molecular weight of the obtained protein sequence is 81.946 kDa and fits well to the native CDH. The calculated isoelectric point is 4.64. The spectrum of C. thermophilus CDH is typical and shows the haem α-, δ- and γ-bands of the reduced enzyme at 562, 533 and 429 nm. In the oxidised enzyme the γ-band has its absorption maximum at 420 nm with a shoulder at 450 nm, which disappears after reduction with lactose and corresponds to the absorption peak of the FAD cofactor. Kinetic characterisation with the cyt c assay resulted in a pH profile with an activity maximum at pH 7.5 and 98% relative activity at pH 7.4 (FIG. 2.b). The specific activity at pH 7.4 was 3.6 U/mg using the cyt c assay and glucose as substrate. The pH optimum of the flavin domain was obtained with the DCIP assay and shows a more acidic pH optimum, however, the flavin domain is sufficiently active at pH 7.4 also with this electron acceptor. Kinetic constants for glucose (obtained with the cyt c assay at pH 5.0) are a $K_M$ of 950 mM and a $k_{cat}$ of 32 s$^{-1}$ for glucose.

To test the electrochemical behaviour of C. thermophilus CDH on electrodes, the purified enzyme preparation was immobilised by adsorption on a spectroscopic graphite electrode surface. Using a flow cell and subsequent injections of 50 mM glucose, DET currents were determined to determine the pH optimum, the current at the pH optimum and the current at pH 7.4. The optimum pH under the chosen conditions is 8.5 and 96% of the maximum current was obtained at pH 7.4 in 10 mM phosphate buffered saline (PBS) containing 100 mM NaCl. The $K_M$ value of the heterogenised enzyme at optimum pH on the electrode surface was determined to be 188 mM and $I_{max}$=190 nA. The currents obtained in glucose measurements should therefore follow a nearly linear relationship for concentrations approx. five-fold below the $K_M$ value. The DET current density obtained at pH 7.4 was 3500 nA/cm$^2$ and the linear range for glucose detection at pH 7.4 with the chosen setup within 1-15 mM.

Example 17: CDH of Hypoxylon haematostroma

A cellobiose dehydrogenase with high glucose turnover rates and activity under physiological pH conditions was obtained from liquid cultures of Hypoxylon haematostroma. The culture was grown and screened as described. The maximum activity under the chosen conditions was 65 U/L (cyt c assay, pH 6.0, 9$^{th}$ day). For enzyme production and purification the outlined procedures were applied and resulted in an CDH preparation with a specific activity of 15.3 U/mg (DCIP assay, pH 6.0), an apparent molecular weight of 85 Da as determined by SDS-PAGE and an isoelectric point of 4.1. The calculated molecular weight of the obtained protein sequence is 87.514 kDa and fits well to the native CDH. The calculated isoelectric point is 6.37. The spectrum of Hypoxylon haematostroma CDH is typical and shows the haem alpha-, beta- and gamma-bands of the reduced enzyme at 563, 533 and 429 nm. In the oxidised enzyme the gamma-band has its absorption maximum at 421 nm with a shoulder at 450 nm, which disappears after reduction with lactose and corresponds to the absorption peak of the FAD cofactor. Kinetic characterisation with the cyt c assay and lactose as electron donor resulted in a neutral pH profile with an activity maximum at pH 5.5 and still 65% relative activity at pH 7.4 (FIG. 2.c). The specific activity at pH 7.4 was 2.73 U/mg using the cyt c assay and glucose as substrate. The pH optimum of the flavin domain was obtained with the DCIP assay and shows a more acidic pH optimum, however, the flavin domain is sufficiently active at pH 7.4 also with this electron acceptor. Kinetic constants for glucose (obtained with the cyt c assay at pH 5.5) are a $K_M$ of 260 mM and a $k_{cat}$ of 8.8 s$^{-1}$ for glucose, which shows in comparison to currently known enzymes a far better suitability of this enzyme for the proposed application.

To test the electrochemical behaviour of Hypoxylon haematostroma CDH on electrodes, the purified enzyme preparation was immobilised by adsorption on a spectroscopic graphite electrode surface. Using a flow cell and subsequent injections of 50 mM glucose, DET currents were determined to determine the pH optimum, the current at the pH optimum and the current at pH 7.4. The optimum pH under the chosen conditions is 7.5 and the maximum current was obtained at this pH and at pH 7.4 in 10 mM phosphate buffered saline (PBS) containing 100 mM NaCl. The $K_M$ value of the heterogenised enzyme at optimum pH (7.4) on the electrode surface for glucose was determined to be 49 mM and $I_{max}$=55 nA. The currents obtained in glucose measurements should therefore follow a nearly linear relationship for concentrations approx. five-fold below the $K_M$ value. The DET current density obtained at pH 7.4 was 383 nA/cm$^2$ and the linear range for glucose detection at pH 7.4 with the chosen setup within 2-20 mM.

Example 18: CDH of Neurospora crassa

A cellobiose dehydrogenase with high glucose turnover rates and activity under physiological pH conditions was obtained from liquid cultures of Neurospora crassa. The culture was grown and screened as described. The maximum activity under the chosen conditions was 156 U/L (cyt c assay, pH 6.0, 18th day). For enzyme production and purification the outlined procedures were applied and resulted in an CDH preparation with a specific activity of 10.6 U/mg (DCIP assay, pH 6.0), an apparent molecular weight of 90 kDa as determined by SDS-PAGE and an isoelectric point of 4.3. The calculated molecular weight of the obtained protein sequence is 86.283 kDa and fits well to the native CDH. The calculated isoelectric point is 6.68. The spectrum of Neurospora crassa CDH is typical and shows the haem alpha-, beta- and gamma-bands of the reduced enzyme at 563, 533 and 430 nm. In the oxidised enzyme the gamma-band has its absorption maximum at 421 nm with a shoulder at 450 nm, which disappears after reduction with lactose and corresponds to the absorption peak of the FAD cofactor. Kinetic characterisation with the cyt c assay and lactose as electron donor resulted in a neutral pH profile with an activity maximum at pH 6.0 and 52% relative activity at pH 7.4 (FIG. 2.d). The specific activity at pH 7.4 was 1.04 U/mg using the cyt c assay and glucose as substrate. The pH optimum of the flavin domain was obtained with the DCIP assay and shows a more acidic pH optimum, however, the flavin domain is sufficiently active at pH 7.4 also with this electron acceptor. Kinetic constants for glucose (obtained with the cyt c assay at pH 5.5) are a $K_M$ of 1680 mM and a kcat of 15.9 s$^{-1}$ for glucose, which shows in comparison to other known enzymes a far better suitability of this enzyme for the proposed application.

To test the electrochemical behaviour of Neurospora crassa CDH on electrodes, the purified enzyme preparation was immobilised by adsorption on a spectroscopic graphite electrode surface. Using a flow cell and subsequent injections of 50 mM glucose, DET currents were determined to determine the pH optimum, the current at the pH optimum and the current at pH 7.4. The optimum pH under the chosen conditions is 5.0 and 31% of the maximum current was obtained at pH 7.4 in 10 mM phosphate buffered saline (PBS) containing 100 mM NaCl. The $K_M$ value of the heterogenised enzyme at optimum pH on the electrode surface was determined to be 90 mM and $I_{max}$=5 nA. The currents obtained in glucose measurements should therefore follow a nearly linear relationship for concentrations approx. five-fold below the $K_M$ value. The DET current density obtained at pH 7.4 was 82 nA/cm² and the linear range for glucose detection at pH 7.4 with the chosen setup within 2-10 mM.

Example 19: CDH of *Stachybotris bisbyi*

A cellobiose dehydrogenase with high glucose turnover rates and activity under physiological pH conditions was obtained from liquid cultures of *Stachybotris bisbyi*. The culture was grown and screened as described. The maximum activity under the chosen conditions was 154 U/L (cyt c assay, pH 6.0, 24$^{th}$ day). For enzyme production and purification the outlined procedures were applied and resulted in a CDH preparation with a specific activity of 7.9 U/mg (DCIP assay, pH 6.0), an apparent molecular weight of 100 kDa as determined by SDS-PAGE and an isoelectric point of 4.5. The calculated molecular weight of the obtained protein sequence is 86.212 kDa and fits well to the native CDH when considering a glycosylation of 14% of *S. bisbyi* CDH, a value which lies within the observed range (2-15%, Zámocký et al., 2006, Current Protein and Peptide Science, 7: 255-280). The calculated isoelectric point is 6.37. The spectrum of *Stachybotris bisbyi* CDH is typical and shows the haem alpha-, beta- and gamma-bands of the reduced enzyme at 562, 533 and 430 nm. In the oxidised enzyme the gamma-band has its absorption maximum at 420 nm with a shoulder at 450 nm, which disappears after reduction with lactose and corresponds to the absorption peak of the FAD cofactor. Kinetic characterisation with the cyt c assay resulted in a pH profile with an activity maximum at pH 5.5 and 60% relative activity at pH 7.4 (FIG. 2.*e*). The specific activity at pH 7.4 was 0.58 U/mg using the cyt c assay and glucose as substrate. The pH optimum of the flavin domain was obtained with the DCIP assay and shows a similar trend indicating that substrate oxidation by the enzyme is efficient at pH 7.4. Kinetic constants for glucose (obtained with the cyt c assay at pH 5.5) are a $K_M$ of 950 mM and a $k_{cat}$ of 14.1 s$^{-1}$ for glucose, which shows in comparison to currently known enzymes a far better suitability of this enzyme for the proposed application.

To test the electrochemical behaviour of *Stachybotris bisbyi* CDH on electrodes, the purified enzyme preparation was immobilised by adsorption on a spectroscopic graphite electrode surface. Using a flow cell and subsequent injections of 50 mM glucose, DET currents were determined to determine the pH optimum, the current at the pH optimum and the current at pH 7.4. The optimum pH under the chosen conditions is 5.0 and 27% of the maximum current was obtained at pH 7.4 in 10 mM phosphate buffered saline (PBS) containing 100 mM NaCl. The $K_M$ value of the heterogenised enzyme at optimum pH on the electrode surface was determined to be 131 mM and $I_{max}$=65 nA. The currents obtained in glucose measurements should therefore follow a nearly linear relationship for concentrations approx. five-fold below the $K_M$ value. The DET current density obtained at pH 7.4 was 237 nA/cm² and the linear range for glucose detection at pH 7.4 with the chosen setup within 3-15 mM.

Example 20: CDH from *Myriococcum thermophilum*

CDH from *Myriococcum thermophilum* was found to oxidise glucose very efficiently (Harreither et al., 2007, Electroanalysis 19: 172-180), but not under physiological conditions. It was used as a protein scaffold for which DET at neutral pH was developed by means of genetic engineering. The enzyme variants D181K and D547S/E550S were obtained according to the described methods to increase the IET at pH 7.4 and thereby the electrode response in order to optimise the enzyme for applications under neutral or alkaline pH conditions.

For enzyme production and purification of the enzyme from the native producer, the protocol given in (Harreither et al., 2007, Electroanalysis 19: 172-180) was followed and resulted in a CDH preparation with a specific activity of 10.7 U/mg (DCIP assay, pH 6.0), an apparent molecular weight of 94 kDa and an isoelectric point of 3.8. The calculated molecular weight of the protein sequence is 86.701 kDa and fits well to the native CDH. The calculated isoelectric point is 4.62. The spectrum of CDH obtained from *M. thermophilum* is typical and shows the haem alpha-, beta- and gamma-bands of the reduced enzyme at 563, 533 and 429 nm. In the oxidised enzyme the gamma-band has its absorption maximum at 421 nm with a shoulder at 450 nm, which disappears after reduction with lactose and corresponds to the absorption peak of the FAD cofactor. Kinetic characterisation with the cyt c assay and lactose as electron donor resulted in a neutral pH profile with an activity maximum between pH 4.0-4.5 and 0% relative activity at pH 7.4 (FIG. 2.*f*). The specific activity at pH 7.4 was also 0 U/mg using the cyt c assay and glucose as substrate. The pH optimum of the flavin domain was obtained with the DCIP assay and shows a far less acidic pH optimum (6.0), indicating that substrate oxidation at the flavin domain is performed even at neutral and slightly alkaline conditions efficiently, but the IET is rate limiting. The obtained kinetic constants for glucose (DCIP assay, pH 6.0; $K_M$=250 mM, kcat=14.2 s$^{-1}$) show that although glucose conversion is very efficient, *M. thermophilum* CDH is not suitable for the proposed application because no IET was measured above pH 7.0.

The recombinant enzyme variants were produced heterologously in *P. pastoris* according to the explained routines. The molecular weights, isoelectric points or spectral properties did not differ significantly from the native enzyme produced by the fungus.

Kinetic characterisation of D181K with the cyt c assay and lactose as electron donor resulted in a pH with an activity maximum at 5.0 and 24% relative activity at pH 7.4 (FIG. 2.*g*). The specific activity at pH 7.4 was 1.01 U/mg using the cyt c assay and glucose as substrate. To test the electrochemical behaviour of D181K on electrodes, the purified enzyme preparation was immobilised by adsorption on a screen printed electrode. Using a flow cell and subsequent injections of 50 mM glucose, DET currents were determined to determine the pH optimum, the current at the pH optimum and the current at pH 7.4. The optimum pH under the chosen conditions is 5.5 and 52% of the maximum current was obtained at pH 7.4 in 10 mM phosphate buffered saline (PBS) containing 100 mM NaCl. The $K_M$ value of the heterogenised enzyme at optimum pH on the electrode surface was determined to be 133 mM and $I_{max}$=105 nA. The currents obtained in glucose measurements should therefore follow a nearly linear relationship for concentrations approx. five-fold below the $K_M$ value. The DET current density obtained at pH 7.4 was 513 nA/cm² and the linear range for glucose detection at pH 7.4 with the chosen setup within 0.5-20 mM.

Kinetic characterisation of D181R with the cyt c assay and lactose as electron donor resulted in a pH with an activity maximum at 5.0 and 20% relative activity at pH 7.4. The specific activity at pH 7.4 was 0.73 U/mg using the cyt c assay and glucose as substrate. To test the electrochemical behaviour of D181R on electrodes, the purified enzyme preparation was immobilised by adsorption on a screen printed electrode. Using a flow cell and subsequent injections of 50 mM glucose, DET currents were determined for pH 5.0 and 7.4 in 10 mM phosphate buffered saline (PBS) containing 100 mM NaCl. The DET current density obtained at pH 5.0 and 7.4 was 485 nA/cm$^2$ and 168 nA/cm$^2$, respectively. The electrode had 42% of the maximum current at pH 7.4.

Kinetic characterisation of D198K with the cyt c assay and lactose as electron donor resulted in a pH with an activity maximum at 5.0 and 22% relative activity at pH 7.4. The specific activity at pH 7.4 was 0.62 U/mg using the cyt c assay and glucose as substrate. To test the electrochemical behaviour of D198K on electrodes, the purified enzyme preparation was immobilised by adsorption on a screen printed electrode. Using a flow cell and subsequent injections of 50 mM glucose, DET currents were determined for pH 5.0 and 7.4 in 10 mM phosphate buffered saline (PBS) containing 100 mM NaCl. The DET current density obtained at pH 5.0 and 7.4 was 259 nA/cm$^2$ and 108 nA/cm$^2$, respectively. The electrode had 42% of the maximum current at pH 7.4.

Kinetic characterisation of D198N with the cyt c assay and lactose as electron donor resulted in a pH with an activity maximum at 5.0 and 22% relative activity at pH 7.4. The specific activity at pH 7.4 was 0.69 U/mg using the cyt c assay and glucose as substrate. To test the electrochemical behaviour of D198N on electrodes, the purified enzyme preparation was immobilised by adsorption on a screen printed electrode. Using a flow cell and subsequent injections of 50 mM glucose, DET currents were determined for pH 5.0 and 7.4 in 10 mM phosphate buffered saline (PBS) containing 100 mM NaCl. The DET current density obtained at pH 5.0 and 7.4 was 353 nA/cm$^2$ and 140 nA/cm$^2$, respectively. The electrode had 40% of the maximum current at pH 7.4.

Kinetic characterisation of D568S/E571S with the cyt c assay and lactose as electron donor resulted in a pH with an activity maximum between 4.5 and 5.0 and 13% relative activity at pH 7.4 (FIG. 2.$h$). The specific activity at pH 7.4 was 0.70 U/mg using the cyt c assay and glucose as substrate. To test the electrochemical behaviour of D568S/E571S on electrodes, the purified enzyme preparation was immobilised by adsorption on a graphite electrode surface. Using a flow cell and subsequent injections of 50 mM glucose, DET currents were determined to determine the pH optimum, the current at the pH optimum and the current at pH 7.4. The optimum pH under the chosen conditions is 5.5 and 24% of the maximum current was obtained at pH 7.4 in 10 mM phosphate buffered saline (PBS) containing 100 mM NaCl. The $K_M$ value of the heterogenised enzyme at optimum pH on the electrode surface was determined to be 55 mM and $I_{max}$=30 nA. The currents obtained in glucose measurements should therefore follow a nearly linear relationship for concentrations approx. five-fold below the $K_M$ value. The DET current density obtained at pH 7.4 was 241 nA/cm$^2$ and the linear range for glucose detection at pH 7.4 with the chosen setup within 1-20 mM.

Kinetic characterisation of D568S/E571S/D574S with the cyt c assay and lactose as electron donor resulted in a pH with an activity maximum at 5.5 and 43% relative activity at pH 7.4. The specific activity at pH 7.4 was 2.49 U/mg using the cyt c assay and glucose as substrate. To test the electrochemical behaviour of D568S/E571S/D574S on electrodes, the purified enzyme preparation was immobilised by adsorption on a screen printed electrode. Using a flow cell and subsequent injections of 50 mM glucose, DET currents were determined for pH 5.0 and 7.4 in 10 mM phosphate buffered saline (PBS) containing 100 mM NaCl. The DET current density obtained at pH 5.0 and 7.4 was 455 nA/cm$^2$ and 184 nA/cm$^2$, respectively. The electrode had 40% of the maximum current at pH 7.4.

Kinetic characterisation of E571K with the cyt c assay and lactose as electron donor resulted in a pH with an activity maximum at 5.0 and 17% relative activity at pH 7.4. The specific activity at pH 7.4 was 0.50 U/mg using the cyt c assay and glucose as substrate. To test the electrochemical behaviour of E571K on electrodes, the purified enzyme preparation was immobilised by adsorption on a screen printed electrode. Using a flow cell and subsequent injections of 50 mM glucose, DET currents were determined for pH 5.0 and 7.4 in 10 mM phosphate buffered saline (PBS) containing 100 mM NaCl. The DET current density obtained at pH 5.0 and 7.4 was 595 nA/cm$^2$ and 197 nA/cm$^2$, respectively. The electrode had 33% of the maximum current at pH 7.4.

Comparative Example 21: CDH from *Myriococcum thermophilum*—pH Profile of Glucose with Wild-Type Enzyme Using Graphite Electrodes CDH from *Myriococcum thermophilum* was found to oxidise many carbohydrates, glucose being one of them (Harreither et al., 2007, Electroanalysis 19: 172-180). From a pH profile measured with 5 mM cellobiose or lactose (FIG. 3A Harreither et al. 2007) a DET current at pH 7.5 can be seen with approx. 17% and 20%, respectively, of the value of peak maximum at pH 5. One could speculate that glucose could also be detected by this method, therefore a comparative measurement was performed using the same experimental conditions, enzyme and electrode preparation procedures (50 mM sodium citrate buffer, pH 4.0, 4.5, 5.0, 5.5, 6.5, 7.5; potential 400 mV vs. Ag☐AgCl in 0.1 M KCl), exchanging the originally used 5 mM cellobiose or 5 mM lactose for 5 mM glucose. The results are given in FIG. 2.$i$ and show a strong decrease of the detected current already at pH 6.5. At pH 7.5 no signal could be detected and therefore no value calculated as the response was within the electronic noise of the measurement (2 nA). The reason for this behaviour lies in the higher $K_M$ value of *M. thermophilum* CDH for glucose ($K_M$=240 mM) than for cellobiose ($K_M$=0.027 mM) or lactose ($K_M$=0.055 mM, all data from Harreither et al. 2007) which reduces the obtained current at pH 7.5 below the limit of detection.

Example 22: Sequences

>M. thermophilum (SEQ ID NO: 1)

mrtssrligalaaallpsalaqnnvpntftdpdsgitfntwgldedspqtqggftf-
gvalpsdalttdasefigylkarndesgwcgislgg edspqtqggtftgvalpsdalttdasefigylkcarndesgwcgislggpmtnsllitawphedtvytslrfatgyampdvyegdaeitqvsssvnsthfslifrcknclqwshggssggastsggvlvlgwvqafddpgnptcpeqitlqqhdngmgiwgaqlntdaaspsytdwaaqatktvtgdcegptetsvvgvpvptgvsfdyivvgggaggipaadklseagksvlliekgfastantggtlgpewleghdltrfdvpglcnqiwvdskgiacedtdqmagcvlgggtavnaglwfkpysldwdylfpdgwkyndvqpainralsripgtdapstdgkryyqegfevlskglaaggwtsvtannapdkknrtfahapfmfaggerngplgtyfahapfmfaggerngplgtyfqtakkrnnfdvwlntsvkrvireggwhitgvevepfrdggyegivpvtkvtgrvilsagtfgfqtakkrnnfdvwlntsvkrvireggwhitgvevepfrdggyegivpvtkvtgrvilsagtfgsakillrsgigpedqlevvaasekdgptmignsswinlpvgynlddhlntdtvishpdvvfydfyeawddpiesdknsylesrtgilaqaapnigpmfweeivgadgivrqlqwtarvegslgapnghtmtmsqylgrgatsrgrmtitpslttivsdvpylkdpndkeaviqgiinlqnalqnvanltwlfpnstitpreyvesmvvspsnrrsnhwmgtnklgtddgrkggsavvdldtrvygtdnlfvidasifpgvpttnptsyivvaaehassrilalpdlepvpkygqcggrewtgsfvcasgstceyqnewysqcl >H. haematostroma (SEQ ID NO: 3)

mgrlgslaklllavglnvqqcfgqngppptpytdsetfitfatwsggnglapwggltfgvalpenalttdateligylkcgsngtttdawcglsfggpmtnslllmawphedeiltsfrfasgytrpdlytgdakltqisstidkdhftfrfasgytrpdlytgdakltqisstidkdhftlifrcqnclawnqdgasgsastsagslilgwaslraptnagcpaeinfnfhnngqmiwlifrcqnclawnqdgasgsastsagslilgwasalraptnagcpaeinfnfhnngqmiwgatldesaanpsysewaakatatvtgdcggatpttttttttsvptatgipvptgtydyivvgagaggipladklseagksvlliekgppssgrwggtlkpewlkdtnltrfdvpglcnqiwvnsagvactdtdqmagcvlgggtavnaglwwkpynldwdynfprgwksrdmaaatrrvfsripgtdnpsmdgrkylqqgfeilagglkaagwtevtandapnkknhtyshspfmfsggerggpmgtylvsasrrknfhlwtgtavkrvvrtgghitglevepfvnggytgvvnvtsitgrvvlsagafgsakillrsgigpedqleivksstdgptmisdsswitlpvgynledhtntdtvvthpdvvfydfyeaghpnvtdkdlylnsragilaqaapnigpmfweeikgdrgvvrqlqstarvegsagtpngyamtmsqylgrgaksrgrmtitkalttvvstvpylqdkndveaviqgiknlqaalsnvknltwayppsnttvedfvnnmlvsytnrrsnhwigtnklgtddgrsrggsavvdlntkvygtdnlfvvdagifpghittnptsyiviaaeraserildlpparaqprfaqcggrtwtgsfqcaapytcqyrnerysqcr >C. attrobruneum (SEQ ID NO: 5)

mrpssrfvgalaaaasflpsalaqnnaavtftdpdtgivfnswglangapqtqggftfgvalpsdalttdatefigylecasadnqgwcgvsmggpmtnsllitawphednvytslrfatgyampdvysgdatitqisssinathfklifcqnclqwthdgasggastsagvlvlgwvqafpspgnptcpdqitleqhnngmgiwgavmdsnvanpsytewaaqatktveaecdgpsetdivgvpvptgttfdyivvgggaggiptadklseagksvlliekgiastaehggtlgpewlegndltrfdvpglcn- -continued qiwvdskgiacedtdqmagcvlgggtavnaglwfkpysldwdylfpsgwkyrdiqaaigrvfsripgtdapstdgkryyqqgfdvlag psgwkyrdiqaaigrvfsripgtdapstdgkryyqqgfdvlagglsaggwnkvtansspdkknrtfsnapfmfsggergggglsaggwnkvtansspdkknrtfsnapfmfsggerggplatyltsakkrsnfnlwlntsvkrvireqqhvtgvevepfrtplatyltsakkrsnfnlwlntsvkrviregghvtgvevepfrtggyqgivnvtavsgrvvlsagtfgsakillrggigpadqlevvkaskidgptmisnaswiplpvgynlddhlntdtvithpdvafydfyeawntpieadknsylssrtgilaqaapnigpmmweeikgadgivrqlqwtarvegsfdtpngqamtisqylgrgatsrgrmtitpslttvvsdvpylkdpndkeaviqgivnlqnalknvagltwtypnssitpreyvdnmvvspsnrranhwmgtakigtddgrlaggsavvdlntkvygtdnlfvvdasifpgtpttnpsayivtaaehasqrilglaapkpvgkwgqcggrqwtgsfqcvsgtkcevvnewysqcl >C. thermophilum (SEQ ID NO: 7)

nkllsrvgatalaatlslkqcaaqmtegtytheatgitfktwtpsdgstftfglalpgdaltndateyigllrcqitdpsspgycgishgqsgqmtqalllvawasedvvytsfryatgytlpelytgdakltqiassvsgdsfevlfrcencfswdqngatgsvststsngalvlgyaakskgltgatcpdtaefgfhnngfgqwgavlegatsdsyeewaqlatitppttcdgngpgdkvcvpapedtydyivvgagaggitvadklseaghkvlliekgppstglwngtmkpewlegtdltrfdvpglcnqiwvdsagiactdtdqmagcvlgggtavnaglwwkphpadwddnfphgwkssdladatervfsripgtwhpsqdgklyrqegfevisqglanagwrevdanqepseknrtyshsvfmfsggerggplatylasaaqrsnfnlwvntsvrrairtgprvsgvelecladggfngtvnlkegggvifsagafgsakllllrsgigpedqleivasskdgetfiskndwiklpvghnlidhlntdliithpdvvfydfyaawdnpitedkeaylnsrsgilaqaapnigplmweevtpsdgitrqfqwtcrvegdssktnsthamtlsqylgrgvvsrgrmgitsgltttthamtlsqylgrgvvsrgrmgitsgltttvaehpylhndgdleaviqgiqnvvdalsqvpdlewvlpppnttveeyvnslivspanrranhwmgtakmglddgrsggsavvdlnt kvygtdnlfvvdasifpgmstgnpsamivivaeqaaqrilslry >S. bisbyi (SEQ ID NO: 9)

mlfklsnwllalalfvgnvvaqlegptpytdpdtgivfqswvnpagtlkfgytypanaatvaatefigflecqgagwcsvslggsmlnkplvvaypsgdevlaslkwatgyanpepyggnhklsqisssvtsagfrvvyrcegclawnqgieggsptngasmpigwaysassvlngdcvdntvliqhdtfgnygfvpdesslrteyndwtelptrvvrgdcggstttssvpsstappqgtgipvptgasydyivvgsgaggipiadklteagkkvlliekgppssgrydgklkptwlegtnltrfdvpglcnqiwvdsagiacrdtdqmagcvlgggtavnaglwwkpnpidwdynfpsgwkssemigatnrvfsriggttvpsqdgktyyqqgfnvlssglkaagwtsvslnnapaqrnrtygapfmfsggerggplatylatakkrgnfdlwtntqvkrvirqgghvtgvevenyngdgykgtvkvtpvsgrvv-
lsagtfgsaklllrsgigpkdqlaivknstdg ptmaserdwinlpvgyledhtntdivishpdvvhydfyeawtasiesdktaylgkrsgilaqaapnigplfffdevrgadnivrsiqytarvegnsvvpngkamvisqylgrgavsrgrmtisqglntivstapylsnvndleaviksleniansltskvknlkiewpasgtsirdhvtnmpldatrranhwigtnkigtkngrltggdsvvdlntkvygtdnlfvvdasifpgmvttnpsayiviaaehaaskilslptakaaakyeqcgglleyngngqcasgltctwlndyywqct >N. crassa (SEQ ID NO: 11)

MRTTSAFLSGLAAVASLLSPAFAQTAPKTFTHPDTGIVFNTWASASDSQTKGGFTFG-MALPSNALTTDATE

FIGYLECSSAKNGANSGWCGVSLRGAMTNNLLITAWPSDGEVYTNLMFATGYAMPKNYAG-DAKITQIASS

VNATHFTLVFRCQNCLSWDQDGVTGGISTSNKGAQLGWVQAFP-SPGNPTCPTQITLSQHDNGMGQWGAAF

DSNIANPSYTAWAAKATKTVTGTCSGPVTTSIAATPVPTGVSFDYIVVGGGAGGIPVAD-KLSESGKSVLL

IEKGFASTGEHGGTLKPEWLNNTSLTRFDVPGLCNQIWKDSDGIACSDTDQMAGCVLGGG-TAINAGLWYK

PYTKDWDYLFPSGWKGSDIAGATSRALSRIPGTTTPSQDGKRYLQQGFEVLANG-LKASGWKEVDSLKDSE

QKNRTFSHTSYMYINGERGGPLATYLVSAKKRSNFKLWLNTAVKRVIRREGGHITGVE-VEAFRNGGYSGII

PVTNTTGRVVLSAGTFGSAKILLRSGIGPKDLQLEVVKASADGPTMVSNSSWIDLPVGH-NLVDHTNTDTVI

QHNNVTFYDFYKAWDNPNTTDMNLYLNGRSGIRAQAAPNIGPLFWEEITGADGIVRQLHW-TARVEGSFET

PDGYAMTMSQYLGRGATSRGRMTLSPTLNTVVSDLPYLKDPND-KAAVVQGIVNLQKALANVKGLTWAYPS

ANQTAADFVDKQPVTYQSRRSNHWMGTNKMGTDDGRSGGTAVVDTNTRVYGTDN-LYVVDASIFPGVPTTN

PTAYIVVAAEHAAAKILAQPANEAVPKWGWCGGPTYTGSQTCQAPYKCEKQNDWYWQCV

>M. thermophilum (SEQ ID NO: 2)

atgaggacctcctctcgtttaatcggagcccttgcggcggcacttttgccgtctgccctt-gcccagaacaatgtcccgaatacttttaccgaccctgactcgggcatcaccttcaacac-gtggggtctcgacgaggattctccccagactcagggcggtttcaccttcggcgtt-gccctgccctctgatgccctcacaaccgacgcctcggaatttatcggttacttgaaatgcg-caaggaatgatgagagcggttggtgtggcatttcccttggcgggcctatgac-caactcgctcctcatcacagcctggccgcacgaggacacggtctacaccag-tcttcggttcgcgaccggttacgccatgccggatgtctacgaggggacgccgagat-tacccaggtctcttcctctgttaattcgacgcacttcagtctcatcttcaggtgcaa-gaactgcctgcaatggagccacggcggctcctccggcggcgcctctac-ctcgggcggcgtgttggtactcggctgggttcaggcattcgacgatcccggcaatccaac-ctgccccgagcagatcacactccagcagcacgacaacggcatggg-tatctggggtgcccagctcaacacggatgctgccagcccgtcctacac-tgactggggccgcccaggctaccaagaccgtcaccggtgactgcgagggcccaccga-gacttctgtcgtcggcgtccccgttccgacgggtgtctcgttcgattatattgtt- -continued gtcggcggcggcgccgggggcatccccgcagctgacaagctcagcgaggccggcaagagtgtgttgctcatcgagaagggctttgcttcgaccgcaaacaccggaggtactctcggccctgaatggcttgagggccatgatctgacccgcttcgacgtgccgggtctgtgcaaccagatctgggtcgattccaaggggatcgcttgcgaggataccgaccagatggctggctgtgttctcggcggcggcaccgccgtgaatgctggcctgtggttcaagccctactcgctcgactgggactacctcttccccgatggttggaagtacaatgacgtccagcctgccatcaaccgcgccctctcgcgcatcccaggcaccgacgccccttctaccgacggaaagcgctactaccaggagggttttgaggtcctctccaagggcctggccgccggcggctggacctcagtcacggccaagaggtcctctccaagggcctggccgccggcggctggacctcagtcacggccaataatgcgcccgacaagaagaaccgcaccttcgcccatgctcccttcatgtttgccggcggcgagcgcaatggccctctgggtacctactttccagactgccaagaagcgcaacaatttcgatgtctggctcaacacgtcggtcaagcgcgtcatccgtgagggtggccacatcaccggcgtcgaggtcgagccgttccgtgacggtggttacgagggcattgtccccgtcaccaaggttaccggccgcgttatcctgtctgccggcaccttcggcagtgcaaagattctgttaaggagcggtattggcccggaagatcagctagaagttgtcgcggcctccgagaaggacggccctaccatgatcggcaactcgtcctggatcaacctgcctgtcgggtacaacctcgatgaccatctcaacaccgacacagtcatctcccaccccgatgtcgtgttctacgacttttacgaggcgtgggatgatcccatcgagtctgacaagaatagctatctcgaatcgcgtacgggcatcctcgcccaagccgctcccaacattggccctatgttctgggaagagatcgtgggcgcggacggcatcgttcgccagctccagtggactgcccgtgtcgagggtagcctgggcgctcccaacggccacactatgaccatgtcgcagtaccttggccgtggtgccacctcacgcggccgcatgaccatcaccccgtctctgacgactatcgtctcagacgtgccttacctcaaagacccaacgacaaggaggctgtcatccaaggcatcatcaacctgcagaacgcccttcagaacgtcgccaacctgacttggctcttccccaactctaccattacgccgcgcgaatacgttgagagcatggtcgtctccccgagcaaccggcggtccaaccactggatgggcaccaacaagctcggtaccgacgacgggcggaagggtggctccgctgtcgtcgacctcgacaccagggtctacggtactgacaacctcttcgtcatcgacgcctccatcttccccggcgtgcccaccacgaatcctacttcgtacatcgtggtagcggcagagcacgcttcgtcccgcatcctcgccctgcccgacctcgagcccgtccccaagtacggccagtgtggcggtcgcgaatggaccggtagcttcgtctgcgccgatggttccacgtgcgagtaccagaatgagtggtactcgcagtgcttgtga >H. haematostroma (SEQ ID NO: 4)

atgggtcgcctaggctctctcgcgaagttgcttctcgcagtcggcttgaatgttcagcaatgcttcgggcaaaacggaccccccgaccccctacactgatagtgagaccggtatcactttcgccacctggtccggcggaaacggcttagaccctggggcggcttgactttcggtgttgcgttacctgaaaatgccctgaccaccgacgctaccgagctgattggatacctgaaatgcggttccaatggcacaaccacagatgcgtggtgtggtctgtcgtttgggggcccgatgactaacagcctccttctcatggcctggccgcacgaagacgagatcttgacatcattccgttttgccagtggatataccagaccagacctatacaccggcgatgccaaattaacgcagatatcatccaccatcgataaagatcactttactctaattttcaggtgccagaactgtctagcgtggaaccaagac- -continued ggcgcgtctggttccgcttcaactagtgccggctccttgatattaggctgggccagtgcgcttcgggccccgactgcgcttcgggccccgacgaatgcaggctgtccggctgaaatcaacttcaacttccacaacaatggccagatgagaatgcaggctgtccggctgaaatcaacttcaacttccacaacaatggccagatgatatgggcgctacattagacgagagcgccgcaaacccatcatattcggaatgggctgccaaagccaccgctacggttaccggtgactgcggcggtgcaacccctacgaccactactaccaccaccacgtccgtccctaccgccacaggtatcccagtgccaatggcacctacgactatattgtagttggtgcgggtgctggcggaatacctttggccgacaagctgagcgaggctggaaagagtgtgttactgatcgaaaaggggccgccatcatcgggacgatggggtggcaccctcaagccagagtggttgaaggacaccaacttgacacggtttgacgtccctggcctgtgcaatcagatctgggtcaactctgcaggcgtcgcttgtactgacacagaccaaatggccggttgcgttcttggtggtggtacagctgtcaacgctggcctatggtggaagccctacaacctcgactgggattataacttcccacgcggatggaagtccaggatatggccgctgcaaccaggagagtcttctctcgcattcccggtacagataatccctcaatggatggcaagcggtatttacagcaaggcttcgaaatcctcgctggtggcttgaaagccgctggatggaccgaggttaccgcgaatgacgcacccaataagaagaaccacacctactcacactcgccgttcatgttctccggcggcaacggggtggcccaatgggcacctacctggtatcggccagtagacgtaagaatttccatctatggacgggaacagcagtgaagagggttgttcgcacaggcggccatatcaccggtctggaggtcgagcccttcgtaaacggcggttataccggtgttgtcaacgtcacctcgattactggtcgggtcgtcttgtctgctggtgcgttcgggtcggctaagatattactgaggagcggcatcggacctgaggatcagttggagattgtcaagtcatcaaccgatggcccgaccatgatttccgattcttcttggattacgctacccgtcggttataatctagaggatcacacaaacaccgacacggtcgttacgcatcctgacgtcgtattttacgacttctacgaggctggacatcctaatgttaccgacaaggacttgtatctcaactcacgggccggaatccttgctcaagcagcgcctaatatcggcccaatgttctgggaagagattaagggtagggacggcgtcgttagacagctccagtggacagccagagttgaaggaagtgccggtacaccgaatgggtacgccatgacaatgagccaataccttggacgaggcgctaatcgaggggccgaatgactatcacgaaggcgttgacgaccgtcgtttctacagtaccttacctacaggataagaacgacgtggaagcagtcatccagggaatcaagaaccttcaagcagcactttcgaacgtgaagaatctcacatgggcctaccaccatctaatacgacggtggaggactttgttaacaacatgctggtttcatacactaataggcgttccaaccactggattgggaccaacaagctcggaaccgatgatggccgatcgcgcggaggttcagctgtcgtggacctcaacactaaggtatacggcaccgacaacctgttcgtcgttgacgcaggaatattccccggtcatattaccacgaacccgacttcgtatatcgtgatcgccgctgagcgcgcttctgagaggatcctcgaccttccccggctagagcacaaccgcgcttcgcgcagtgcggcgggcgaacgtggacgggtagcttccagtgtgcagcgcctacacttgtcagtacaggaatgagcggtattcccagtgccggtaa >C. attrobruneum (SEQ ID NO: 6)

atgaggccctcctctcggtttgttggtgccctggcggcggcggcgtcgttcctgccgtctgcccttgcccagaacaatgctgcagggtgccctggcggcggcggcgtcgttcctgccgtctgcccttgcccagaacaatgctgcagtcaccttcactgaccccggacaccggcatcgtcttcaactcctggggtcttgccaatggagcac- -continued

```
cacagactcagggaggcttcacctttggtgtcgctctgccctctgatgcgctcacgac-
cgatgctaccgagttcattggttatttggaatgtgcctccgcggacaac-
cagggctggtgcggtgtctcgatgggcggcccatgaccaactcgcttcttatcac-
cgcctggccgcacgaggacaacgtctacacctccctccggtttgcaacaggatac-
gccatgccggatgtctactcgggagacgccaccatcacgcagatctcgtcgagcatcaac-
gcgacccacttcaagctcatcttcaggtgccagaactgcctgcaatggacccacgacggcgcttccggtggcgcctccac-
ggcgcttccggtggcgcctccacgtctgccggtgttctggtcctcggctgggtccaggctttcccttccctggcaacccgac-
gtctgccggtgttctggtcctcggctgggtccaggctttcccttccctggcaacccgac-
gtgcccgaccagatcacgctcgagcagcacaacaacggcatggg-
catctggggtgcggtgatggactccaacgtcgccaacccgtcctacacagagtgggccgcg-
caggccaccaagacggtcgaggccgagtgcgacggcccgagtgagacgga-
tattgtcggcgtgcccgtgccgaccggcaccaccttcgac-
tacatcgtcgtgggcggcggtgccggcggtatccccactgccgacaagctcagcgaggccgg-
caagagtgtgctgctgattgagaagggcatcgcctcgactgctgagcacggcggcactctcg-
gacccgagtggctcgagggcaacgacctgacgcggttcgacgtgcccggtctttgcaac-
cagatctgggttgactccaagggcatcgcctgcgaggacaccgaccagatggccggtt-
gcgtcctcggcggcggcacggccgtcaacgccggcctctggttcaa-
gccctactcgctcgactgggactacctcttcccaagcggctggaagtac-
cgcgacatccaggccgccatcggcagggtgttctcgcgcatcccgggcactgac-
gcgccctcgaccgacggcaagcgctactaccagcagggcttcgac-
gtgctcgcgggcggcctgagtgccggcggctggaacaaggtcacggccaactcgtctccaga-
caagaagaaccgcaccttctcgaacgcgcctttcatgttctcgggcggcgagcgcggcgggcccctggccacttatctcac-
gcgcctttcatgttctcgggcggcgagcgcggcgggcccctggccacttatctcac-
cagcgccaagaagcgcagcaacttcaacctgtggctcaacacgtcggtcaa-
gcgcgtcatccgtgagggcggccacgtcacaggtgtcgaggtcgagcctttccggac-
gggcgggtaccagggtatcgtgaacgttaccgccgtttcgggccgtgtcgtcctgtcggctgg-
tacctttcggcagtgccaagattctgctcagaggcggtattggcccagcg-
gatcagctcgaggttgtcaaggcgtcgaagatcgacgggccgaccatgatcag-
caatgcgtcttggattcctctgcctgttgggtacaacctggatgaccatctcaacac-
tgacactgtcattacccaccccgacgttgccttctacgacttctacgaggcatggaacac-
gcccattgaggcggacaagaacagctacctgagcagccgcactgg-
tatcctcgctcaggccgcgcccaacattggcccaatgatgtgggag-
gaaatcaagggtgccgacggtatcgtccgccagctgcaatggaccgcccgtgtcgaggg-
tagctttgacacgcctaacgggcaggcgatgaccatctcgcagtac-
ctcggccgcggcgacctcgcgcggccgtatgaccatcacccttcgctgacgac-
cgtcgtctcggacgtgccgtacctcaaggacccgaacgataaggaggccgtcatccaggg-
catcgtcaacctgcagaacgccctcaaaaacgtcgccggcctgacctggac-
ctaccccaactcgagcatcacaccgcgcgaatacgtcgataatatggtagtctcccctag-
caaccggcgcgcaaaccactggatgggcacggccaaaatcggcaccgacgac-
ggccgcctggccggcggctccgccgtcgtggacttgaacaccaaggtctacggcac-
cgacaacctctttgtcgtggacgcgtccatcttccccggcacgcccaccac-
```

-continued caatccctcggcgtacatcgtcacggctgcggagcatgcttcgcagaggatcttggggtt-
ggctgcgccgaagccggttgggaaatggggccagtgtggcgggcggcagtg-
gacagggagcttccagtgcgtgagtgggacaaagtgtgaggtggtgaatgagtggtactcgcagtgcttgtag >C. thermophilum (SEQ ID NO: 8)

atgaagcttctcagccgcgttggggccaccgccctagcggcgacgtt-
gtccctgaaacaatgtgcagctcagatgaccgaagggacgtacacccatgaggctaccgg-
tatcacgttcaagacatggactccttccgacggctcgactttcactttcggctt-
ggccctcctggggacgcgctgacaaatgatgccaccgagtacattggtctcctgcgtt-
gccaaatcaccgatccctcttcgcccggctactgtggcatctcccacggccag-
tccggccagatgacgcaggcgctgctgctggtcgcttgggccagcgaggatgtcgtctacac-
gtcgttccgctacgccaccggctacacactccccgagctctacacgggcgacgccaa-
gctgacccagatcgcctcctcggtcagcggggacagcttcgaggtgctgttccgctgcga-
gaactgcttctcctgggaccagaacggcgccacgggcagtgtctcgaccagcaac-
ggcgccctggttctcggctacgctgcctcgaagagtggtttgacgggcgccacgtgcccg-
gacacggccgagtttggcttccacaacaatggtttcggacagtggggtgcag-
tgctcgagggtgcgacctcggactcgtatgaggagtgggctcagctggccactatcac-
gcccccgaccacctgcgatggcaacggccctggcgacaaggtgtgcgttccggctcccgaaga-
cacgtatgattacatcgttgtcggcgccggcgccggcggcatcacggtcgccgacaa-
gctcagcgaggccggccacaaggtcctccttatcgagaagggtcctccgtcgaccggcctgtg-
gaacgggaccatgaagcccgagtggctcgagggtaccgacctcacccgcttcgac-
gtccccggtctgtgcaaccagatctgggtcgactctgccggcattgcctgcaccgataccgac-
cagatggcgggctgcgttctcggcggtggcaccgctgtcaatgctggtctgtggtggaa-
gccccaccccgctgactgggacgacaacttccctcatggctggaagtcgagcgatctcgcg-
gatgcgaccgagcgtgtcttcagccgcattcccggcacgtggcacccgtcgcaggatgg-
caaactgtaccgccaggagggcttcgaggtcatcagccagggcctggccaacgccggctg-
gagggaagtcgacgccaaccaggagcccagcgagaagaaccgcacgtattcccacag-
tgtgttcatgttctcgggcggtgagcgcggcggccccctggcgacgtac-
ctcgcctcggctgcccagcgcagcaacttcaacttgtgggtcaacacttcggtccg-
gagggccatccgcaccggcccagggtcagtggcgtcgaactcgagtgccttgcggacggcggcttcaacggtactgtcaac-
ggcggcttcaacggtactgtcaacctgaaggagggtggtggtgtcatcttttcggctggcgctttcggctcggccaa-
ctgaaggagggtggtgtcatcttttcggctggcgctttcggctcggccaa-
gctgctccttcgcagcggcatcggtcctgaggaccagctcga-
gattgtggcgagctccaaggacggcgagaccttcatttccaagaatgattggatcaa-
gctccccgtcggccataacctgatcgatcatctcaacaccgacctcattattactcacccg-
gatgtcgttttctatgacttctacgcggcttgggacaatcccatcaccgaggacaaggaggcc-
tacctgaactcgcggtccggcattctcgcccaagcggcgcccaacatcggccctctgatgtgg-
gaggaagtcacgccatccgacggcatcacccgccagttccagtggacatgccgtgtt-
gagggcgacagctccaagaccaactcgacccacgccatgaccctcagccag-
tatctcggccgtggcgtcgtctcgcgcggccggatgggcatcacttccgggctgaccacgac-
ggtggccgagcacccgtacctgcacaacgacggcgacctggaggcggtgatccaggg- -continued tatccagaacgtggtggacgcgctcagccaggtgcccgacctcgagtgggtgctcccgccgcccaacacgacggtggaggaatacgtcaacagcctgatcgtgtctccggctaaccgccgggccaaccactggatgggcacggccaagatgggcctcgatgacggccgctcgggcggctccgcggtcgtcgacctcaacacaaaggtgtatggcaccgacaacctgtttgtcgtcgacgcctccatcttccctggcatgtcgacgggcaacccgtcggctatgatcgtcatcgtggccgagcaggcggcccagcgcatcctgtccctgcggtattag >S. bisbyi                                                                    (SEQ ID NO: 10)

atgctgttcaagctctcaaattggttgctagcgcttgcgctcttttgttggcaatgtcgttgctcaactcgaggggcctaccccgtacacggatccagataccggcattgtctttcagtcctgggtcaatccagcagggaccctgaagtttggttacacttaccccgcaaatgctgctacggttgccgccacggaatttatcggtttcctggaatgccaaggggctggatggtgtagcgtctcactcggtggctccatgcttaacaagccgcttgttgttgcctaccctagtggcgatgaagtcctcgcttctttgaagtgggccacaggctacgcgaatccagagccttacggcggcaatcacaagctgtcccagatcagctcgtccgtcacctctgctggcttcagggtcgtctatcgatgtgagggatgtctcgcctggaactaccagggaattgagggagggagccccaccaatggtgcgtccatgcctatcggttgggcttacagcgcaagttctgtactcaacggggattgtgtggataacactgttctcattcaacatgacacctttggcaattatggcttcgtacctgatgaatcatctcttcgcacggagtacaatgactggacggagcttccgaccagggttgtcaggggagactgcggcggttccacaactacctcttcggtgccctcctcaacggcgcctcctcaaggtactggcataccggttcctactggcgcaagctatgactacatagttgttggctcgggtgctggaggtattcccattgcggataagcttaccgaggctggcaaaaaggttttgttgattgagaagggaccaccctcttctggtcgctacgatggaaagctaaagccgacgtggcttgagggaactaatctcacccgattcgatgtgcctggcctctgcaaccaaatatgggtcgactccgctggcattgcatgccgtgataccgatcagatggctggttgtgttcttggcggtggtactgctgtcaatgcaggtctatggtggaagcctaaccctattgattgggactataatttcccttcaggctggaagtcaagcgagatgataggcgcgacaaaccgtgtcttttcacgtattggtggtactactgttccttcgcaggacggaaagacctactatcagcaaggtttcaacgttctttccagcggtctcaaggctgcgggctggacatctgttagcctgaataacgcccctgcgcaaaggaaccgcacctatggtgctggccctttcatgttctctggtggagagcgaggtggacctttggccacctacctggccactgccaagaagagaggaaacttcgacctctggacgaatacccaagttaagcgtgtaattcgacagggaggtcatgttactggagtggaggtcgaaaactataacggtgatgggtacaagggcactgtcaaggtgactcctgtatctgggcgagttgtcctatctgctggtacctttggcagtgctaagcttttgctccgaagcggtatcggtcccaaggatcaactagctattgtcaagaactcgactgatggccctactatggcttccgagagggactggattaatcttcccgttggctacaacttggaggaccatactaacaccgacattgtcatctcccatccagatgtggtccattacgacttctatgaggcttggacagcgtcaatcgagtctgacaagactgcttatttgggcaagcgttctggcatcctcgctcaagccgcccccaacatcgggcctctcttctttgacgaagttcgcggtgctgacaacattgtccgctcaattcagtacactgctcgtgtggagggcaacagtgtggtccctaatggcaaggccatggtgatcagccagtacctt- -continued ggtcgtggcgctgtttccaggggtcgaatgaccatctctcaaggtctcaatacgattgtttccaccgctccatacctctcaaacgtcaatgatctcgaggccgtcattaagagccttgagaacatagcgaacagcttgacgtcaaaggttaaaaacctcaagattgaatggcctgcctctggtacatccattcgcgatcacgtcacgaatatgcctctcgacccggccacccgccgagcgaatcattggattggcactaacaagatcggaaccaagaatggtcgactgacaggtggtgattccgtcgttgatttgaacactaaggtctatggtacagacaatctgtttgtggtcgatgcttctattttccctggcatggttacgaccaaccccctcggcctacattgtaattgccgctgagcatgctgcatcgaagattctgagcctacctactgctaaggctgccgcgaagtacgaacaatgtggtggccttgaatataatggtaactttcagtgtgcgtctggattaacctgcacttggttaaacgactactactggcagtgtacttaa >N. crassa (SEQ ID NO: 12)

atgaggaccacctcggcctttctcagcggcctggcggcggtggcttcattgctgtcgcccgccttcgcccaaaccgctcccaagaccttcactcatcctgataccggcattgtcttcaacacatggagtgcttccgattcccagaccaaaggtggcttcactgttggtatggctctgccgtcaaatgctcttactaccgacgcgactgaattcatcggttatctggaatgctcctccgccaagaatggtgccaatagcggttggtgcggtgtttctctcagaggcgccatgaccaacaatctactcattacggtgcggtgtttctctcagaggcgccatgaccaacaatctactcattaccgcctggccttctgacggagaagtctacaccaatctcatgttcgccacgggttacgccatgcccaagaactacgctggtgacgccaagatcacccagatcgcgtccagcgtgaacgctacccacttcacccttgtctttaggtgccagaactgtttgtcatgggaccaagacggtgtcaccggcggcatttctaccagcaataaggggggcccagctcggttgggtccaggcgttcccctctcccggcaacccgacttgccctaccagatcactctcagtcagcatgacaacggtatgggccagtggggagctgcctttgacagcaacattgccaatccctcttatactgcatgggctgccaaggccaccaagaccgttaccggtacttgcagtggtccagtcacgaccagtattgccgccactcctgttcccactggcgtttcttttgactacattgtcgttggtggtggtgccggtggtattcccgtcgctgacaagctcagcgagtccggtaagagcgtgctgctcatcgagaagggtttcgcttccactggtgagcatggtggtactctgaagcccgagtggctgaataatacatcccttactcgcttcgatgttcccggtcttttgcaaccagatctggaaagactcggatggcattgcctgctccgataccgatcagatggccggctgcgtgctcggcggtggtaccgccatcaacgccggtctctggtacaagcccacaccaaggactgggactacctcttcccctctggctggaagggcagcgatatcgccggtgctaccagcagagccctctcccgcattccgggtaccaccactccttctcaggatggaaagcgctaccttcagcagggtttcgaggttcttgccaacggcctcaaggcgagcggctggaaggaggtcgattccctcaaggacagcgagcagaagaaccgcactttctcccacacctcatacactttctcccacacctcatacatgtacatcaatggcgagcgtggcggtcctctagcgacttacctcgtcagcgccaagaagcgcatgtacatcaatggcgagcgtggcggtcctctagcgacttacctcgtcagcgccaagaagcgcagcaacttcaagctgtggctcaacaccgctgtcaagcgcgtcatccgtgagggcggccacattaccggtgtggaggttgaggccttccgcaacggcggctactccggaatcatccccgtcaccaacaccaccggccgcgtcgttctttccgccggcaccttcggcagcgccaagatccttctccgttccggcattggccccaaggacgatccttctccgttccggcattggccccaaggac- -continued

```
cagctcgaggtggtcaaggcctccgccgacggccctaccatggtcagcaactcgtcctg-
gattgacctccccgtcggccacaacctggttgaccacaccaacaccgacaccgtcatccag-
cacaacaacgtgaccttctacgacttttacaaggcttgggacaaccccaacacgac-
cgacatgaacctgtacctcaatgggcgctccggcatcttcgcccaggccgcgcccaacatt-
ggccccttgttctggaggagatcacgggcgccgacggcatcgtccgtcagctgcactggac-
cgcccgcgtcgagggcagcttcgagaccccgacggctacgccatgaccatgagccagtac-
cttggccgtggcgccacctcgcgcggccgcatgaccctcagccctaccctcaacac-
cgtcgtgtctgacctcccgtacctcaaggaccccaacgacaaggccgctgtcgttcaggg-
tatcgtcaacctccagaaggctctcgccaacgtcaagggtctcac-
ctgggcttaccctagcgccaaccagacggctgctgattttgttgacaagcaacccgtaac-
ctaccaatcccgccgctccaaccactggatgggcaccaacaagatgggcaccgacgacggccg-
cagcggcggcaccgcagtcgtcgacaccaacacgcgcgtctatggcaccgacaacctgtac-
gtggtggacgcctcgattttccccggtgtgccgaccaccaaccctaccgcctacatt-
gtcgtcgccgctgagcatgccgcggccaaaatcctggcgcaacccgccaac-
gaggccgttcccaagtggggctggtgcggcgggccgacgtatactggcagccagac-
gtgccaggcgccatataagtgcgagaagcagaatgattggtattggcagtgtgtgtag
```

---

The invention claimed is:

1. A method of detecting and/or quantifying glucose or lactose in a sample comprising:
providing a cellobiose dehydrogenase from *Neurospora crassa* or a cellobiose dehydrogenase comprising an amino acid sequence that is at least 80% identical to SEQ ID NO: 11;
contacting a fluid sample with the cellobiose dehydrogenase; detecting and quantifying oxidation of glucose or lactose in the sample by the cellobiose dehydrogenase;
detecting and quantifying the glucose or lactose in the sample based on the amount of oxidation.

2. The method of claim 1, wherein the oxidation is detected electrochemically.

3. The method of claim 2, wherein the oxidation is detected with an immobilized cellobiose dehydrogenase on an electrode.

4. The method of claim 1, wherein the cellobiose dehydrogenase has at least 10% glucose, lactose or cellobiose oxidizing activity at a pH of 7.4 as compared to maximal activity at a lower pH as determined by a cyt c assay.

5. The method of claim 4, wherein the cellobiose dehydrogenase has at least 20% glucose, lactose or cellobiose oxidizing activity at a pH of 7.4 as compared to maximal activity at a lower pH as determined by a cyt c assay.

6. The method of claim 5, wherein the cellobiose dehydrogenase has at least 30% glucose, lactose or cellobiose oxidizing activity at a pH of 7.4 as compared to maximal activity at a lower pH as determined by a cyt c assay.

7. The method of claim 1, wherein fluid sample has a pH of at least 6.0.

8. The method of claim 1, wherein the glucose oxidation activity of the cellobiose dehydrogenase at pH 7.4 is at least 0.5 U/mg cellobiose dehydrogenase.

9. The method of claim 1, wherein the Km value of the cellobiose dehydrogenase for an glucose oxidation reaction at pH 7.4 is below 1M.

* * * * *

UNITED STATES PATENT AND TRADEMARK OFFICE
CERTIFICATE OF CORRECTION

PATENT NO. : 9,873,864 B2  
APPLICATION NO. : 15/593507  
DATED : January 23, 2018  
INVENTOR(S) : Roland Ludwig et al.

Page 1 of 1

It is certified that error appears in the above-identified patent and that said Letters Patent is hereby corrected as shown below:

<u>Item (73) Assignee:</u>
Replace "Klosterneuburg (DE)" with -- Klosterneuburg (AT) --.

Signed and Sealed this
Fifteenth Day of May, 2018

Andrei Iancu
*Director of the United States Patent and Trademark Office*

SEQUENCE LISTING

<160> NUMBER OF SEQ ID NOS: 33

<210> SEQ ID NO 1
<211> LENGTH: 828
<212> TYPE: PRT
<213> ORGANISM: Myriococcum thermophilum

<400> SEQUENCE: 1

```
Met Arg Thr Ser Ser Arg Leu Ile Gly Ala Leu Ala Ala Ala Leu Leu
1               5                   10                  15

Pro Ser Ala Leu Ala Gln Asn Asn Val Pro Asn Thr Phe Thr Asp Pro
            20                  25                  30

Asp Ser Gly Ile Thr Phe Asn Thr Trp Gly Leu Asp Glu Asp Ser Pro
        35                  40                  45

Gln Thr Gln Gly Gly Phe Thr Phe Gly Val Ala Leu Pro Ser Asp Ala
    50                  55                  60

Leu Thr Thr Asp Ala Ser Glu Phe Ile Gly Tyr Leu Lys Cys Ala Arg
65                  70                  75                  80

Asn Asp Glu Ser Gly Trp Cys Gly Ile Ser Leu Gly Gly Pro Met Thr
                85                  90                  95

Asn Ser Leu Leu Ile Thr Ala Trp Pro His Glu Asp Thr Val Tyr Thr
            100                 105                 110

Ser Leu Arg Phe Ala Thr Gly Tyr Ala Met Pro Asp Val Tyr Glu Gly
        115                 120                 125

Asp Ala Glu Ile Thr Gln Val Ser Ser Val Asn Ser Thr His Phe
    130                 135                 140

Ser Leu Ile Phe Arg Cys Lys Asn Cys Leu Gln Trp Ser His Gly Gly
145                 150                 155                 160

Ser Ser Gly Gly Ala Ser Thr Ser Gly Gly Val Leu Val Leu Gly Trp
                165                 170                 175

Val Gln Ala Phe Asp Asp Pro Gly Asn Pro Thr Cys Pro Glu Gln Ile
```

```
                  180                 185                 190
Thr Leu Gln Gln His Asp Asn Gly Met Gly Ile Trp Gly Ala Gln Leu
            195                 200                 205
Asn Thr Asp Ala Ala Ser Pro Ser Tyr Thr Asp Trp Ala Ala Gln Ala
        210                 215                 220
Thr Lys Thr Val Thr Gly Asp Cys Glu Gly Pro Thr Glu Thr Ser Val
225                 230                 235                 240
Val Gly Val Pro Val Pro Thr Gly Val Ser Phe Asp Tyr Ile Val Val
                245                 250                 255
Gly Gly Gly Ala Gly Gly Ile Pro Ala Ala Asp Lys Leu Ser Glu Ala
            260                 265                 270
Gly Lys Ser Val Leu Leu Ile Glu Lys Gly Phe Ala Ser Thr Ala Asn
        275                 280                 285
Thr Gly Gly Thr Leu Gly Pro Glu Trp Leu Glu Gly His Asp Leu Thr
            290                 295                 300
Arg Phe Asp Val Pro Gly Leu Cys Asn Gln Ile Trp Val Asp Ser Lys
305                 310                 315                 320
Gly Ile Ala Cys Glu Asp Thr Asp Gln Met Ala Gly Cys Val Leu Gly
                325                 330                 335
Gly Gly Thr Ala Val Asn Ala Gly Leu Trp Phe Lys Pro Tyr Ser Leu
            340                 345                 350
Asp Trp Asp Tyr Leu Phe Pro Asp Gly Trp Lys Tyr Asn Asp Val Gln
        355                 360                 365
Pro Ala Ile Asn Arg Ala Leu Ser Arg Ile Pro Gly Thr Asp Ala Pro
    370                 375                 380
Ser Thr Asp Gly Lys Arg Tyr Tyr Gln Glu Gly Phe Glu Val Leu Ser
385                 390                 395                 400
Lys Gly Leu Ala Ala Gly Gly Trp Thr Ser Val Thr Ala Asn Asn Ala
                405                 410                 415
Pro Asp Lys Lys Asn Arg Thr Phe Ala His Ala Pro Phe Met Phe Ala
            420                 425                 430
Gly Gly Glu Arg Asn Gly Pro Leu Gly Thr Tyr Phe Gln Thr Ala Lys
        435                 440                 445
Lys Arg Asn Asn Phe Asp Val Trp Leu Asn Thr Ser Val Lys Arg Val
    450                 455                 460
Ile Arg Glu Gly Gly His Ile Thr Gly Val Glu Val Glu Pro Phe Arg
465                 470                 475                 480
Asp Gly Gly Tyr Glu Gly Ile Val Pro Val Thr Lys Val Thr Gly Arg
                485                 490                 495
Val Ile Leu Ser Ala Gly Thr Phe Gly Ser Ala Lys Ile Leu Leu Arg
            500                 505                 510
Ser Gly Ile Gly Pro Glu Asp Gln Leu Glu Val Val Ala Ala Ser Glu
        515                 520                 525
Lys Asp Gly Pro Thr Met Ile Gly Asn Ser Ser Trp Ile Asn Leu Pro
    530                 535                 540
Val Gly Tyr Asn Leu Asp Asp His Leu Asn Thr Asp Thr Val Ile Ser
545                 550                 555                 560
His Pro Asp Val Val Phe Tyr Asp Phe Tyr Glu Ala Trp Asp Asp Pro
                565                 570                 575
Ile Glu Ser Asp Lys Asn Ser Tyr Leu Glu Ser Arg Thr Gly Ile Leu
            580                 585                 590
Ala Gln Ala Ala Pro Asn Ile Gly Pro Met Phe Trp Glu Glu Ile Val
        595                 600                 605
```

Gly Ala Asp Gly Ile Val Arg Gln Leu Gln Trp Thr Ala Arg Val Glu
            610                 615                 620

Gly Ser Leu Gly Ala Pro Asn Gly His Thr Met Thr Met Ser Gln Tyr
625                 630                 635                 640

Leu Gly Arg Gly Ala Thr Ser Arg Gly Arg Met Thr Ile Thr Pro Ser
                645                 650                 655

Leu Thr Thr Ile Val Ser Asp Val Pro Tyr Leu Lys Asp Pro Asn Asp
            660                 665                 670

Lys Glu Ala Val Ile Gln Gly Ile Asn Leu Gln Asn Ala Leu Gln
        675                 680                 685

Asn Val Ala Asn Leu Thr Trp Leu Phe Pro Asn Ser Thr Ile Thr Pro
690                 695                 700

Arg Glu Tyr Val Glu Ser Met Val Val Ser Pro Ser Asn Arg Arg Ser
705                 710                 715                 720

Asn His Trp Met Gly Thr Asn Lys Leu Gly Thr Asp Asp Gly Arg Lys
                725                 730                 735

Gly Gly Ser Ala Val Val Asp Leu Asp Thr Arg Val Tyr Gly Thr Asp
                740                 745                 750

Asn Leu Phe Val Ile Asp Ala Ser Ile Phe Pro Gly Val Pro Thr Thr
            755                 760                 765

Asn Pro Thr Ser Tyr Ile Val Val Ala Ala Glu His Ala Ser Ser Arg
770                 775                 780

Ile Leu Ala Leu Pro Asp Leu Glu Pro Val Pro Lys Tyr Gly Gln Cys
785                 790                 795                 800

Gly Gly Arg Glu Trp Thr Gly Ser Phe Val Cys Ala Asp Gly Ser Thr
                805                 810                 815

Cys Glu Tyr Gln Asn Glu Trp Tyr Ser Gln Cys Leu
            820                 825

<210> SEQ ID NO 2
<211> LENGTH: 2487
<212> TYPE: DNA
<213> ORGANISM: Myriococcum thermophilum

<400> SEQUENCE: 2
atgaggacct cctctcgttt aatcggagcc cttgcggcgg cacttttgcc gtctgccctt        60
gcccagaaca atgtcccgaa tacttttacc gaccctgact cgggcatcac cttcaacacg       120
tggggtctcg acgaggattc tccccagact cagggcggtt tcaccttcgg cgttgccctg       180
ccctctgatg ccctcacaac cgacgcctcg gaatttatcg gttacttgaa atgcgcaagg       240
aatgatgaga gcggttggtg tggcattttc cttggcgggc ctatgaccaa ctcgctcctc       300
atcacagcct ggccgcacga ggacacggtc tacaccagtc ttcggttcgc gaccggttac       360
gccatgccgg atgtctacga gggggacgcc gagattaccc aggtctcttc ctctgttaat       420
tcgacgcact tcagtctcat cttcaggtgc aagaactgcc tgcaatggag ccacggcggc       480
tcctccggcg gcgcctctac ctcgggcggc gtgttggtac tcggctgggt tcaggcattc       540
gacgatcccg caatccaac ctgccccgag cagatcacac tccagcagca cgacaacggc       600
atgggtatct ggggtgccca gctcaacacg atgctgcca gccgtccta cactgactgg       660 gccgcccagg ctaccaagac cgtcaccggt gactgcgagg ccccaccga cttctgtc        720 gtcgcgtcc ccgttccgac gggtgtctcg ttcgattata ttgttgtcgg cggcggcgcc       780
gggggcatcc ccgcagctga caagctcagc gaggccggca agagtgtgtt gctcatcgag       840

-continued

```
aagggctttg cttcgaccgc aaacaccgga ggtactctcg gccctgaatg gcttgagggc    900
catgatctga cccgcttcga cgtgccgggt ctgtgcaacc agatctgggt cgattccaag    960
gggatcgctt gcgaggatac cgaccagatg gctggctgtg ttctcggcgg cggcaccgcc   1020
gtgaatgctg gcctgtggtt caagccctac tcgctcgact gggactacct cttccccgat   1080
ggttggaagt acaatgacgt ccagcctgcc atcaaccgcg ccctctcgcg catcccaggc   1140
accgacgccc cttctaccga cggaaagcgc tactaccagg agggttttga ggtcctctcc   1200
aagggcctgg ccgccggcgg ctggacctca gtcacggcca ataatgcgcc cgacaagaag   1260
aaccgcacct cgcccatgc tcccttcatg tttgccggcg gcgagcgcaa tggccctctg   1320
ggtacctact tccagactgc caagaagcgc aacaatttcg atgtctggct caacacgtcg   1380
gtcaagcgcg tcatccgtga gggtggccac atcaccggcg tcgaggtcga gccgttccgt   1440
gacggtggtt acgagggcat tgtccccgtc accaaggtta ccggccgcgt tatcctgtct   1500
gccggcacct tcggcagtgc aaagattctg ttaaggagcg gtattggccc ggaagatcag   1560
ctagaagttg tcgcggcctc cgagaaggac ggccctacca tgatcggcaa ctcgtcctgg   1620
atcaacctgc ctgtcgggta caacctcgat gaccatctca acaccgacac agtcatctcc   1680
caccccgatg tcgtgttcta cgactttttac gaggcgtggg atgatcccat cgagtctgac   1740
aagaatagct atctcgaatc gcgtacgggc atcctcgccc aagccgctcc caacattggc   1800
cctatgttct gggaagagat cgtgggcgcg gacggcatcg ttcgccagct ccagtggact   1860
gcccgtgtcg agggtagcct gggcgctccc aacggccaca ctatgaccat gtcgcagtac   1920
cttggccgtg gtgccacctc acgcggccgc atgaccatca ccccgtctct gacgactatc   1980
gtctcagacg tgccttacct caaagacccc aacgacaagg aggctgtcat ccaaggcatc   2040
atcaacctgc agaacgccct tcagaacgtc gccaacctga cttggctctt ccccaactct   2100
accattacgc cgcgcgaata cgttgagagc atggtcgtct ccccgagcaa ccggcggtcc   2160
aaccactgga tgggcaccaa caagctcggt accgacgacg gcggaagggg tggctccgct   2220
gtcgtcgacc tcgacaccag ggtctacggt actgacaacc tcttcgtcat cgacgcctcc   2280
atcttccccg gcgtgcccac cacgaatcct acttcgtaca tcgtggtagc ggcagagcac   2340
gcttcgtccc gcatcctcgc cctgcccgac ctcgagcccg tccccaagta cggccagtgt   2400
ggcggtcgcg aatggaccgg tagcttcgtc tgcgccgatg gttccacgtg cgagtaccag   2460
aatgagtggt actcgcagtg cttgtga                                       2487
```

<210> SEQ ID NO 3
<211> LENGTH: 839
<212> TYPE: PRT
<213> ORGANISM: H. haematostroma

<400> SEQUENCE: 3

Met Gly Arg Leu Gly Ser Leu Ala Lys Leu Leu Ala Val Gly Leu
1               5                   10                  15

Asn Val Gln Gln Cys Phe Gly Gln Asn Gly Pro Thr Pro Tyr Thr
            20                  25                  30

Asp Ser Glu Thr Gly Ile Thr Phe Ala Thr Trp Ser Gly Gly Asn Gly
        35                  40                  45

Leu Ala Pro Trp Gly Gly Leu Thr Phe Gly Val Ala Leu Pro Glu Asn
    50                  55                  60

Ala Leu Thr Thr Asp Ala Thr Glu Leu Ile Gly Tyr Leu Lys Cys Gly
65                  70                  75                  80

-continued

```
Ser Asn Gly Thr Thr Thr Asp Ala Trp Cys Gly Leu Ser Phe Gly Gly
                85                  90                  95

Pro Met Thr Asn Ser Leu Leu Leu Met Ala Trp Pro His Glu Asp Glu
            100                 105                 110

Ile Leu Thr Ser Phe Arg Phe Ala Ser Gly Tyr Thr Arg Pro Asp Leu
            115                 120                 125

Tyr Thr Gly Asp Ala Lys Leu Thr Gln Ile Ser Ser Thr Ile Asp Lys
            130                 135                 140

Asp His Phe Thr Leu Ile Phe Arg Cys Gln Asn Cys Leu Ala Trp Asn
145                 150                 155                 160

Gln Asp Gly Ala Ser Gly Ser Ala Ser Thr Ser Ala Gly Ser Leu Ile
                165                 170                 175

Leu Gly Trp Ala Ser Ala Leu Arg Ala Pro Thr Asn Ala Gly Cys Pro
            180                 185                 190

Ala Glu Ile Asn Phe Asn Phe His Asn Asn Gly Gln Met Ile Trp Gly
            195                 200                 205

Ala Thr Leu Asp Glu Ser Ala Ala Asn Pro Ser Tyr Ser Glu Trp Ala
            210                 215                 220

Ala Lys Ala Thr Ala Thr Val Thr Gly Asp Cys Gly Gly Ala Thr Pro
225                 230                 235                 240

Thr Thr Thr Thr Thr Thr Thr Ser Val Pro Thr Ala Thr Gly Ile
                245                 250                 255

Pro Val Pro Thr Gly Thr Tyr Asp Tyr Ile Val Val Gly Ala Gly Ala
            260                 265                 270

Gly Gly Ile Pro Leu Ala Asp Lys Leu Ser Glu Ala Gly Lys Ser Val
            275                 280                 285

Leu Leu Ile Glu Lys Gly Pro Pro Ser Ser Gly Arg Trp Gly Gly Thr
            290                 295                 300

Leu Lys Pro Glu Trp Leu Lys Asp Thr Asn Leu Thr Arg Phe Asp Val
305                 310                 315                 320

Pro Gly Leu Cys Asn Gln Ile Trp Val Asn Ser Ala Gly Val Ala Cys
            325                 330                 335

Thr Asp Thr Asp Gln Met Ala Gly Cys Val Leu Gly Gly Thr Ala
            340                 345                 350

Val Asn Ala Gly Leu Trp Trp Lys Pro Tyr Asn Leu Asp Trp Asp Tyr
            355                 360                 365

Asn Phe Pro Arg Gly Trp Lys Ser Arg Asp Met Ala Ala Ala Thr Arg
            370                 375                 380

Arg Val Phe Ser Arg Ile Pro Gly Thr Asp Asn Pro Ser Met Asp Gly
385                 390                 395                 400

Lys Arg Tyr Leu Gln Gln Gly Phe Glu Ile Leu Ala Gly Gly Leu Lys
            405                 410                 415

Ala Ala Gly Trp Thr Glu Val Thr Ala Asn Asp Ala Pro Asn Lys Lys
            420                 425                 430

Asn His Thr Tyr Ser His Ser Pro Phe Met Phe Ser Gly Gly Glu Arg
            435                 440                 445

Gly Gly Pro Met Gly Thr Tyr Leu Val Ser Ala Ser Arg Arg Lys Asn
            450                 455                 460

Phe His Leu Trp Thr Gly Thr Ala Val Lys Arg Val Arg Thr Gly
465                 470                 475                 480

Gly His Ile Thr Gly Leu Glu Val Glu Pro Phe Val Asn Gly Gly Tyr
                485                 490                 495

Thr Gly Val Val Asn Val Thr Ser Ile Thr Gly Arg Val Val Leu Ser
```

```
                500             505             510
Ala Gly Ala Phe Gly Ser Ala Lys Ile Leu Leu Arg Ser Gly Ile Gly
            515                 520                 525

Pro Glu Asp Gln Leu Glu Ile Val Lys Ser Ser Thr Asp Gly Pro Thr
    530                 535                 540

Met Ile Ser Asp Ser Ser Trp Ile Thr Leu Pro Val Gly Tyr Asn Leu
545                 550                 555                 560

Glu Asp His Thr Asn Thr Asp Thr Val Val Thr His Pro Asp Val Val
                565                 570                 575

Phe Tyr Asp Phe Tyr Glu Ala Gly His Pro Asn Val Thr Asp Lys Asp
            580                 585                 590

Leu Tyr Leu Asn Ser Arg Ala Gly Ile Leu Ala Gln Ala Ala Pro Asn
        595                 600                 605

Ile Gly Pro Met Phe Trp Glu Glu Ile Lys Gly Arg Asp Gly Val Val
    610                 615                 620

Arg Gln Leu Gln Trp Thr Ala Arg Val Glu Gly Ser Ala Gly Thr Pro
625                 630                 635                 640

Asn Gly Tyr Ala Met Thr Met Ser Gln Tyr Leu Gly Arg Gly Ala Lys
                645                 650                 655

Ser Arg Gly Arg Met Thr Ile Thr Lys Ala Leu Thr Thr Val Val Ser
            660                 665                 670

Thr Val Pro Tyr Leu Gln Asp Lys Asn Asp Val Glu Ala Val Ile Gln
        675                 680                 685

Gly Ile Lys Asn Leu Gln Ala Ala Leu Ser Asn Val Lys Asn Leu Thr
    690                 695                 700

Trp Ala Tyr Pro Pro Ser Asn Thr Thr Val Glu Asp Phe Val Asn Asn
705                 710                 715                 720

Met Leu Val Ser Tyr Thr Asn Arg Arg Ser Asn His Trp Ile Gly Thr
                725                 730                 735

Asn Lys Leu Gly Thr Asp Asp Gly Arg Ser Arg Gly Gly Ser Ala Val
            740                 745                 750

Val Asp Leu Asn Thr Lys Val Tyr Gly Thr Asp Asn Leu Phe Val Val
        755                 760                 765

Asp Ala Gly Ile Phe Pro Gly His Ile Thr Thr Asn Pro Thr Ser Tyr
    770                 775                 780

Ile Val Ile Ala Ala Glu Arg Ala Ser Glu Arg Ile Leu Asp Leu Pro
785                 790                 795                 800

Pro Ala Arg Ala Gln Pro Arg Phe Ala Gln Cys Gly Gly Arg Thr Trp
                805                 810                 815

Thr Gly Ser Phe Gln Cys Ala Ala Pro Tyr Thr Cys Gln Tyr Arg Asn
            820                 825                 830

Glu Arg Tyr Ser Gln Cys Arg
        835

<210> SEQ ID NO 4
<211> LENGTH: 2520
<212> TYPE: DNA
<213> ORGANISM: H. haematostroma

<400> SEQUENCE: 4
atgggtcgcc taggctctct cgcgaagttg cttctcgcag tcggcttgaa tgttcagcaa      60
tgcttcgggc aaaacggacc cccgaccccc tacactgata gtgagaccgg tatcactttc     120
gccacctggt ccggcggaaa cggcttagca ccctggggcg gcttgacttt cggtgttgcg     180
```

```
ttacctgaaa atgccctgac caccgacgct accgagctga ttggatacct gaaatgcggt    240
tccaatggca caaccacaga tgcgtggtgt ggtctgtcgt ttgggggccc gatgactaac    300
agcctccttc tcatggcctg ccgcacgaa gacgagatct tgacatcatt ccgttttgcc    360
agtggatata ccagaccaga cctatacacc ggcgatgcca aattaacgca gatatcatcc    420
accatcgata aagatcactt tactctaatt ttcaggtgcc agaactgtct agcgtggaac    480
caagacggcg cgtctggttc cgcttcaact agtgccggct ccttgatatt aggctgggcc    540
agtgcgcttc gggccccgac gaatgcaggc tgtccggctg aaatcaactt caacttccac    600
aacaatggcc agatgatatg gggcgctaca ttagacgaga cgccgcaaa cccatcatat    660 tcggaatggg ctgccaaagc caccgctacg gttaccggtg actgcggcgg tgcaaccct    720 acgaccacta ctaccaccac cacgtccgtc cctaccgcca caggtatccc agtgccaact    780
ggcacctacg actatattgt agttggtgcg ggtgctggcg gaataccttt ggccgacaag    840
ctgagcgagg ctggaaagag tgtgttactg atcgaaaagg ggccgccatc atcgggacga    900
tggggtggca ccctcaagcc agagtggttg aaggacacca acttgacacg gtttgacgtc    960
cctggcctgt gcaatcagat ctgggtcaac tctgcaggcg tcgcttgtac tgacacagac    1020
caaatggccg gttgcgttct tggtggtggt acagctgtca acgctggcct atggtggaag    1080
ccctacaacc tcgactggga ttataacttc ccacgcggat ggaagtccag ggatatggcc    1140
gctgcaacca ggagagtctt ctctcgcatt cccggtacga taatccctc aatggatggc    1200 aagcggtatt tacagcaagg cttcgaaatc ctcgctggtg gcttgaaagc cgctggatgg    1260
accgaggtta ccgcgaatga cgcacccaat aagaagaacc acacctactc acactcgccg    1320
ttcatgttct ccggcggcga acggggtggc ccaatgggca cctacctggt atcggccagt    1380
agacgtaaga atttccatct atggacggga acagcagtga agagggttgt tcgcacaggc    1440
ggccatatca ccggtctgga ggtcgagccc ttcgtaaacg gcggttatac cggtgttgtc    1500
aacgtcacct cgattactgg tcgggtcgtc ttgtctgctg gtgcgttcgg gtcggctaag    1560
atattactga ggagcggcat cggacctgag gatcagttgg agattgtcaa gtcatcaacc    1620
gatggcccga ccatgatttc cgattcttct tggattacgc tacccgtcgg ttataatcta    1680
gaggatcaca caaacaccga cacggtcgtt acgcatcctg acgtcgtatt ttacgacttc    1740
tacgaggctg gacatcctaa tgttaccgac aaggacttgt atctcaactc acgggccgga    1800
atccttgctc aagcagcgcc taatatcggc ccaatgttct gggaagagat taagggtagg    1860
gacggcgtcg ttagacagct ccagtggaca gccagagttg aaggaagtgc cggtacaccg    1920
aatgggtacg ccatgacaat gagccaatac cttggacgag gcgctaagtc gaggggccga    1980
atgactatca cgaaggcgtt gacgaccgtc gtttctacag taccttacct acaggataag    2040
aacgacgtgg aagcagtcat ccagggaatc aagaaccttc aagcagcact ttcgaacgtg    2100
aagaatctca catgggccta cccaccatct aatacgacgg tggaggactt tgttaacaac    2160
atgctggttt catacactaa taggcgttcc aaccactgga ttgggaccaa caagctcgga    2220
accgatgatg gccgatcgcg cggaggttca gctgtcgtgg acctcaacac taaggtatac    2280
ggcaccgaca acctgttcgt cgttgacgca ggaatattcc ccggtcatat taccacgaac    2340
ccgacttcgt atatcgtgat cgccgctgag cgcgcttctg agaggatcct cgaccttccc    2400
ccggctagag cacaaccgcg cttgcgcag tgcggcgggc gaacgtggac gggtagcttc    2460
cagtgtgcag cgccgtacac ttgtcagtac aggaatgagc ggtattccca gtgccggtaa    2520
```

<210> SEQ ID NO 5
<211> LENGTH: 831
<212> TYPE: PRT
<213> ORGANISM: C. attrobruneum

<400> SEQUENCE: 5

| Met | Arg | Pro | Ser | Ser | Arg | Phe | Val | Gly | Ala | Leu | Ala | Ala | Ala | Ala | Ser |
|---|---|---|---|---|---|---|---|---|---|---|---|---|---|---|---|
| 1 | | | | 5 | | | | | 10 | | | | | 15 | |

| Phe | Leu | Pro | Ser | Ala | Leu | Ala | Gln | Asn | Asn | Ala | Ala | Val | Thr | Phe | Thr |
| | | | 20 | | | | | 25 | | | | | 30 | | |

| Asp | Pro | Asp | Thr | Gly | Ile | Val | Phe | Asn | Ser | Trp | Gly | Leu | Ala | Asn | Gly |
| | | | 35 | | | | | 40 | | | | | 45 | | |

| Ala | Pro | Gln | Thr | Gln | Gly | Gly | Phe | Thr | Phe | Gly | Val | Ala | Leu | Pro | Ser |
| | 50 | | | | | 55 | | | | | 60 | | | | |

| Asp | Ala | Leu | Thr | Thr | Asp | Ala | Thr | Glu | Phe | Ile | Gly | Tyr | Leu | Glu | Cys |
| 65 | | | | | 70 | | | | | 75 | | | | | 80 |

| Ala | Ser | Ala | Asp | Asn | Gln | Gly | Trp | Cys | Gly | Val | Ser | Met | Gly | Gly | Pro |
| | | | | 85 | | | | | 90 | | | | | 95 | |

| Met | Thr | Asn | Ser | Leu | Leu | Ile | Thr | Ala | Trp | Pro | His | Glu | Asp | Asn | Val |
| | | | 100 | | | | | 105 | | | | | 110 | | |

| Tyr | Thr | Ser | Leu | Arg | Phe | Ala | Thr | Gly | Tyr | Ala | Met | Pro | Asp | Val | Tyr |
| | | | 115 | | | | | 120 | | | | | 125 | | |

| Ser | Gly | Asp | Ala | Thr | Ile | Thr | Gln | Ile | Ser | Ser | Ile | Asn | Ala | Thr |
| | 130 | | | | | 135 | | | | | 140 | | | | |

| His | Phe | Lys | Leu | Ile | Phe | Arg | Cys | Gln | Asn | Cys | Leu | Gln | Trp | Thr | His |
| 145 | | | | | 150 | | | | | 155 | | | | | 160 |

| Asp | Gly | Ala | Ser | Gly | Ala | Ser | Thr | Ser | Ala | Gly | Val | Leu | Val | Leu |
| | | | | | 165 | | | | | 170 | | | | | 175 |

| Gly | Trp | Val | Gln | Ala | Phe | Pro | Ser | Pro | Gly | Asn | Pro | Thr | Cys | Pro | Asp |
| | | | 180 | | | | | 185 | | | | | 190 | | |

| Gln | Ile | Thr | Leu | Glu | Gln | His | Asn | Asn | Gly | Met | Gly | Ile | Trp | Gly | Ala |
| | | | 195 | | | | | 200 | | | | | 205 | | |

| Val | Met | Asp | Ser | Asn | Val | Ala | Asn | Pro | Ser | Tyr | Thr | Glu | Trp | Ala | Ala |
| | 210 | | | | | 215 | | | | | 220 | | | | |

| Gln | Ala | Thr | Lys | Thr | Val | Glu | Ala | Glu | Cys | Asp | Gly | Pro | Ser | Glu | Thr |
| 225 | | | | | 230 | | | | | 235 | | | | | 240 |

| Asp | Ile | Val | Gly | Val | Pro | Val | Pro | Thr | Gly | Thr | Thr | Phe | Asp | Tyr | Ile |
| | | | | 245 | | | | | 250 | | | | | 255 | |

| Val | Val | Gly | Gly | Gly | Ala | Gly | Gly | Ile | Pro | Thr | Ala | Asp | Lys | Leu | Ser |
| | | | 260 | | | | | 265 | | | | | 270 | | |

| Glu | Ala | Gly | Lys | Ser | Val | Leu | Leu | Ile | Glu | Lys | Gly | Ile | Ala | Ser | Thr |
| | | | 275 | | | | | 280 | | | | | 285 | | |

| Ala | Glu | His | Gly | Gly | Thr | Leu | Gly | Pro | Glu | Trp | Leu | Glu | Gly | Asn | Asp |
| | 290 | | | | | 295 | | | | | 300 | | | | |

| Leu | Thr | Arg | Phe | Asp | Val | Pro | Gly | Leu | Cys | Asn | Gln | Ile | Trp | Val | Asp |
| 305 | | | | | 310 | | | | | 315 | | | | | 320 |

| Ser | Lys | Gly | Ile | Ala | Cys | Glu | Asp | Thr | Asp | Gln | Met | Ala | Gly | Cys | Val |
| | | | | 325 | | | | | 330 | | | | | 335 | |

| Leu | Gly | Gly | Gly | Thr | Ala | Val | Asn | Ala | Gly | Leu | Trp | Phe | Lys | Pro | Tyr |
| | | | 340 | | | | | 345 | | | | | 350 | | |

| Ser | Leu | Asp | Trp | Asp | Tyr | Leu | Phe | Pro | Ser | Gly | Trp | Lys | Tyr | Arg | Asp |
| | | | 355 | | | | | 360 | | | | | 365 | | |

| Ile | Gln | Ala | Ala | Ile | Gly | Arg | Val | Phe | Ser | Arg | Ile | Pro | Gly | Thr | Asp |
| | 370 | | | | | 375 | | | | | 380 | | | | |

```
Ala Pro Ser Thr Asp Gly Lys Arg Tyr Tyr Gln Gln Gly Phe Asp Val
385                 390                 395                 400

Leu Ala Gly Gly Leu Ser Ala Gly Gly Trp Asn Lys Val Thr Ala Asn
            405                 410                 415

Ser Ser Pro Asp Lys Lys Asn Arg Thr Phe Ser Asn Ala Pro Phe Met
        420                 425                 430

Phe Ser Gly Gly Glu Arg Gly Gly Pro Leu Ala Thr Tyr Leu Thr Ser
        435                 440                 445

Ala Lys Lys Arg Ser Asn Phe Asn Leu Trp Leu Asn Thr Ser Val Lys
    450                 455                 460

Arg Val Ile Arg Glu Gly Gly His Val Thr Gly Val Glu Val Glu Pro
465                 470                 475                 480

Phe Arg Thr Gly Gly Tyr Gln Gly Ile Val Asn Val Thr Ala Val Ser
            485                 490                 495

Gly Arg Val Val Leu Ser Ala Gly Thr Phe Gly Ser Ala Lys Ile Leu
            500                 505                 510

Leu Arg Gly Gly Ile Gly Pro Ala Asp Gln Leu Glu Val Val Lys Ala
    515                 520                 525

Ser Lys Ile Asp Gly Pro Thr Met Ile Ser Asn Ala Ser Trp Ile Pro
530                 535                 540

Leu Pro Val Gly Tyr Asn Leu Asp Asp His Leu Asn Thr Asp Thr Val
545                 550                 555                 560

Ile Thr His Pro Asp Val Ala Phe Tyr Asp Phe Tyr Glu Ala Trp Asn
            565                 570                 575

Thr Pro Ile Glu Ala Asp Lys Asn Ser Tyr Leu Ser Ser Arg Thr Gly
            580                 585                 590

Ile Leu Ala Gln Ala Ala Pro Asn Ile Gly Pro Met Met Trp Glu Glu
    595                 600                 605

Ile Lys Gly Ala Asp Gly Ile Val Arg Gln Leu Gln Trp Thr Ala Arg
610                 615                 620

Val Glu Gly Ser Phe Asp Thr Pro Asn Gly Gln Ala Met Thr Ile Ser
625                 630                 635                 640

Gln Tyr Leu Gly Arg Gly Ala Thr Ser Arg Gly Arg Met Thr Ile Thr
            645                 650                 655

Pro Ser Leu Thr Thr Val Val Ser Asp Val Pro Tyr Leu Lys Asp Pro
            660                 665                 670

Asn Asp Lys Glu Ala Val Ile Gln Gly Ile Val Asn Leu Gln Asn Ala
    675                 680                 685

Leu Lys Asn Val Ala Gly Leu Thr Trp Thr Tyr Pro Asn Ser Ser Ile
    690                 695                 700

Thr Pro Arg Glu Tyr Val Asp Asn Met Val Val Ser Pro Ser Asn Arg
705                 710                 715                 720

Arg Ala Asn His Trp Met Gly Thr Ala Lys Ile Gly Thr Asp Asp Gly
            725                 730                 735

Arg Leu Ala Gly Gly Ser Ala Val Val Asp Leu Asn Thr Lys Val Tyr
            740                 745                 750

Gly Thr Asp Asn Leu Phe Val Val Asp Ala Ser Ile Phe Pro Gly Thr
            755                 760                 765

Pro Thr Thr Asn Pro Ser Ala Tyr Ile Val Thr Ala Ala Glu His Ala
            770                 775                 780

Ser Gln Arg Ile Leu Gly Leu Ala Ala Pro Lys Pro Val Gly Lys Trp
785                 790                 795                 800

Gly Gln Cys Gly Gly Arg Gln Trp Thr Gly Ser Phe Gln Cys Val Ser
```

| | 805 | | | | 810 | | | | 815 | | |
|---|---|---|---|---|---|---|---|---|---|---|---|
| Gly | Thr | Lys | Cys | Glu | Val | Val | Asn | Glu | Trp | Tyr | Ser | Gln | Cys | Leu |
| | | | | 820 | | | | | 825 | | | | 830 | |

<210> SEQ ID NO 6
<211> LENGTH: 2496
<212> TYPE: DNA
<213> ORGANISM: C. attrobruneum

<400> SEQUENCE: 6

```
atgaggccct cctctcggtt tgttggtgcc ctggcggcgg cggcgtcgtt cctgccgtct      60
gcccttgccc agaacaatgc tgcagtcacc ttcactgacc cggacaccgg catcgtcttc     120
aactcctggg gtcttgccaa tggagcacca cagactcagg gaggcttcac ctttggtgtc     180
gctctgccct tgatgcgct cacgaccgat gctaccgagt tcattggtta tttggaatgt      240
gcctccgcgg acaaccaggg ctggtgcggt gtctcgatgg gcggccccat gaccaactcg     300
cttcttatca ccgcctggcc gcacgaggac aacgtctaca cctcccctcg gtttgcaaca     360
ggatacgcca tgccggatgt ctactcggga gacgccacca tcacgcagat ctcgtcgagc     420
atcaacgcga cccacttcaa gctcatcttc aggtgccaga actgcctgca atggaccccac    480
gacggcgctt ccggtggcgc ctccacgtct gccggtgttc tggtcctcgg ctgggtccag     540
gctttccctt ccctggcaa cccgacgtgc cggaccaga tcacgctcga gcagcacaac       600
aacggcatgg gcatctgggg tgcggtgatg gactccaacg tcgccaaccc gtcctacaca     660
gagtgggccg cgcaggccac caagacggtc gaggccgagt cgacggccc gagtgagacg      720
gatattgtcg gcgtgcccgt gccgaccggc accaccttcg actacatcgt cgtgggcggc     780
ggtgccggcg tatccccac tgccgacaag ctcagcgagg ccggcaagag tgtgctgctg      840
attgagaagg gcatcgcctc gactgctgag cacgcggca ctctcggacc cgagtggctc      900
gagggcaacg acctgacgcg gttcgacgtg cccggtcttt gcaaccagat ctgggttgac     960
tccaagggca tcgcctgcga ggacaccgac cagatggccg gttgcgtcct cggcggcggc    1020
acggccgtca cgccggcct ctggttcaag ccctactcgc tcgactggga ctacctcttc     1080
ccaagcggct ggaagtaccg cgacatccag gccgccatcg cagggtgtt ctcgcgcatc     1140
ccgggcactg acgcgccctc gaccgacggc aagcgctact accagcaggg cttcgacgtg    1200
ctcgcgggcg gcctgagtgc cggcggctgg aacaaggtca cggccaactc gtctccagac    1260
aagaagaacc gcaccttctc gaacgcgcct ttcatgttct cgggcggcga gcgcggcggg    1320
cccctggcca cttatctcac cagcgccaag aagcgcagca acttcaacct gtggctcaac    1380
acgtcggtca gcgcgtcat ccgtgagggc ggccacgtca caggtgtcga ggtcgagcct     1440
ttccggacgg gcgggtacca gggtatcgtg aacgttaccg ccgtttcggg ccgtgtcgtc    1500
ctgtcggctg gtaccttcgg cagtgccaag attctgctca gaggcggtat ggcccagcg    1560
gatcagctcg aggttgtcaa ggcgtcgaag atcgacgggc cgaccatgat cagcaatgcg    1620
tcttggattc ctctgcctgt tgggtacaac ctggatgacc atctcaacac tgacactgtc    1680
attacccacc ccgacgttgc cttctacgac ttctacgagg catggaacac gcccattgag    1740
gcggacaaga acagctacct gagcagccgc actggtatcc tcgctcaggc cgcgcccaac    1800
attggcccaa tgatgtggga ggaaatcaag ggtgccgacg tatcgtccg ccagctgcaa     1860
tggaccgccc gtcgagggg tagctttgac acgcctaacg gcaggcgat gaccatctcg      1920
cagtacctcg gccgcggcgc gacctcgcgc ggccgtatga ccatcacccc ttcgctgacg    1980
```

-continued

```
accgtcgtct cggacgtgcc gtacctcaag acccgaacg ataaggaggc cgtcatccag      2040
ggcatcgtca acctgcagaa cgccctcaaa acgtcgccg gcctgacctg gacctacccc      2100
aactcgagca tcacaccgcg cgaatacgtc gataatatgg tagtctcccc tagcaaccgg      2160
cgcgcaaacc actggatggg cacggccaaa atcggcaccg acgacggccg cctggccggc      2220
ggctccgccg tcgtggactt gaacaccaag gtctacggca ccgacaacct ctttgtcgtg      2280
gacgcgtcca tcttccccgg cacgcccacc accaatccct cggcgtacat cgtcacgggct     2340 gcggagcatg cttcgcagag gatcttgggg ttggctgcgc cgaagccggt tgggaaatgg      2400
ggccagtgtg gcgggcggca gtggacaggg agcttccagt gcgtgagtgg gacaaagtgt     2460
gaggtggtga atgagtggta ctcgcagtgc ttgtag                                2496
```

<210> SEQ ID NO 7
<211> LENGTH: 787
<212> TYPE: PRT
<213> ORGANISM: C. thermophilum

<400> SEQUENCE: 7

```
Met Lys Leu Leu Ser Arg Val Gly Ala Thr Ala Leu Ala Ala Thr Leu
1               5                   10                  15

Ser Leu Lys Gln Cys Ala Ala Gln Met Thr Glu Gly Thr Tyr Thr His
            20                  25                  30

Glu Ala Thr Gly Ile Thr Phe Lys Thr Trp Thr Pro Ser Asp Gly Ser
        35                  40                  45

Thr Phe Thr Phe Gly Leu Ala Leu Pro Gly Asp Ala Leu Thr Asn Asp
    50                  55                  60

Ala Thr Glu Tyr Ile Gly Leu Leu Arg Cys Gln Ile Thr Asp Pro Ser
65                  70                  75                  80

Ser Pro Gly Tyr Cys Gly Ile Ser His Gly Gln Ser Gly Gln Met Thr
                85                  90                  95

Gln Ala Leu Leu Leu Val Ala Trp Ala Ser Glu Asp Val Val Tyr Thr
            100                 105                 110

Ser Phe Arg Tyr Ala Thr Gly Tyr Thr Leu Pro Glu Leu Tyr Thr Gly
        115                 120                 125

Asp Ala Lys Leu Thr Gln Ile Ala Ser Ser Val Ser Gly Asp Ser Phe
    130                 135                 140

Glu Val Leu Phe Arg Cys Glu Asn Cys Phe Ser Trp Asp Gln Asn Gly
145                 150                 155                 160

Ala Thr Gly Ser Val Ser Thr Ser Asn Gly Ala Leu Val Leu Gly Tyr
                165                 170                 175

Ala Ala Ser Lys Ser Gly Leu Thr Gly Ala Thr Cys Pro Asp Thr Ala
            180                 185                 190

Glu Phe Gly Phe His Asn Asn Gly Phe Gly Gln Trp Gly Ala Val Leu
        195                 200                 205

Glu Gly Ala Thr Ser Asp Ser Tyr Glu Glu Trp Ala Gln Leu Ala Thr
    210                 215                 220

Ile Thr Pro Pro Thr Thr Cys Asp Gly Asn Gly Pro Gly Asp Lys Val
225                 230                 235                 240

Cys Val Pro Ala Pro Glu Asp Thr Tyr Asp Tyr Ile Val Val Gly Ala
                245                 250                 255

Gly Ala Gly Gly Ile Thr Val Ala Asp Lys Leu Ser Glu Ala Gly His
            260                 265                 270

Lys Val Leu Leu Ile Glu Lys Gly Pro Pro Ser Thr Gly Leu Trp Asn
        275                 280                 285
```

-continued

```
Gly Thr Met Lys Pro Glu Trp Leu Glu Gly Thr Asp Leu Thr Arg Phe
            290                 295                 300

Asp Val Pro Gly Leu Cys Asn Gln Ile Trp Val Asp Ser Ala Gly Ile
305                 310                 315                 320

Ala Cys Thr Asp Thr Asp Gln Met Ala Gly Cys Val Leu Gly Gly Gly
                325                 330                 335

Thr Ala Val Asn Ala Gly Leu Trp Trp Lys Pro His Pro Ala Asp Trp
                340                 345                 350

Asp Asp Asn Phe Pro His Gly Trp Lys Ser Ser Asp Leu Ala Asp Ala
            355                 360                 365

Thr Glu Arg Val Phe Ser Arg Ile Pro Gly Thr Trp His Pro Ser Gln
    370                 375                 380

Asp Gly Lys Leu Tyr Arg Gln Glu Gly Phe Glu Val Ile Ser Gln Gly
385                 390                 395                 400

Leu Ala Asn Ala Gly Trp Arg Glu Val Asp Ala Asn Gln Glu Pro Ser
                405                 410                 415

Glu Lys Asn Arg Thr Tyr Ser His Ser Val Phe Met Phe Ser Gly Gly
            420                 425                 430

Glu Arg Gly Gly Pro Leu Ala Thr Tyr Leu Ala Ser Ala Ala Gln Arg
    435                 440                 445

Ser Asn Phe Asn Leu Trp Val Asn Thr Ser Val Arg Arg Ala Ile Arg
450                 455                 460

Thr Gly Pro Arg Val Ser Gly Val Glu Leu Glu Cys Leu Ala Asp Gly
465                 470                 475                 480

Gly Phe Asn Gly Thr Val Asn Leu Lys Glu Gly Gly Val Ile Phe
                485                 490                 495

Ser Ala Gly Ala Phe Gly Ser Ala Lys Leu Leu Leu Arg Ser Gly Ile
                500                 505                 510

Gly Pro Glu Asp Gln Leu Glu Ile Val Ala Ser Ser Lys Asp Gly Glu
            515                 520                 525

Thr Phe Ile Ser Lys Asn Asp Trp Ile Lys Leu Pro Val Gly His Asn
    530                 535                 540

Leu Ile Asp His Leu Asn Thr Asp Leu Ile Ile Thr His Pro Asp Val
545                 550                 555                 560

Val Phe Tyr Asp Phe Tyr Ala Ala Trp Asp Asn Pro Ile Thr Glu Asp
                565                 570                 575

Lys Glu Ala Tyr Leu Asn Ser Arg Ser Gly Ile Leu Ala Gln Ala Ala
            580                 585                 590

Pro Asn Ile Gly Pro Leu Met Trp Glu Val Thr Pro Ser Asp Gly
    595                 600                 605

Ile Thr Arg Gln Phe Gln Trp Thr Cys Arg Val Glu Gly Asp Ser Ser
    610                 615                 620

Lys Thr Asn Ser Thr His Ala Met Thr Leu Ser Gln Tyr Leu Gly Arg
625                 630                 635                 640

Gly Val Val Ser Arg Gly Arg Met Gly Ile Thr Ser Gly Leu Thr Thr
                645                 650                 655

Thr Val Ala Glu His Pro Tyr Leu His Asn Asp Gly Asp Leu Glu Ala
                660                 665                 670

Val Ile Gln Gly Ile Gln Asn Val Val Asp Ala Leu Ser Gln Val Pro
            675                 680                 685

Asp Leu Glu Trp Val Leu Pro Pro Asn Thr Thr Val Glu Glu Tyr
    690                 695                 700
```

| | | | | | | | | | | | |
|---|---|---|---|---|---|---|---|---|---|---|---|
|Val|Asn|Ser|Leu|Ile|Val|Ser|Pro|Ala|Asn|Arg|Ala|Asn|His|Trp|
|705| | | |710| | | |715| | | |720|

Met Gly Thr Ala Lys Met Gly Leu Asp Asp Gly Arg Ser Gly Ser
            725                 730                 735

Ala Val Val Asp Leu Asn Thr Lys Val Tyr Gly Thr Asp Asn Leu Phe
        740                 745                 750

Val Val Asp Ala Ser Ile Phe Pro Gly Met Ser Thr Gly Asn Pro Ser
        755                 760                 765

Ala Met Ile Val Ile Val Ala Glu Gln Ala Ala Gln Arg Ile Leu Ser
    770                 775                 780

Leu Arg Tyr
785

<210> SEQ ID NO 8
<211> LENGTH: 2364
<212> TYPE: DNA
<213> ORGANISM: C. thermophilum

<400> SEQUENCE: 8

```
atgaagcttc tcagccgcgt tgggccacc gccctagcgg cgacgttgtc cctgaaacaa      60
tgtgcagctc agatgaccga aggacgtac acccatgagg ctaccggtat cacgttcaag     120
acatggactc cttccgacgg ctcgactttc actttcggct ggccctcccc tggggacgcg     180
ctgacaaatg atgccaccga gtacattggt ctcctgcgtt gccaaatcac cgatccctct     240
tcgcccggct actgtggcat ctcccacggc cagtccggcc agatgacgca ggcgctgctg     300
ctggtcgctt gggccagcga ggatgtcgtc tacacgtcgt tccgctacgc caccggctac     360
acactccccg agctctacac gggcgacgcc aagctgaccc agatcgcctc ctcggtcagc     420
ggggacagct tcgaggtgct gttccgctgc gagaactgct tctcctggga ccagaacggc     480
gccacgggca gtgtctcgac cagcaacggc gccctggttc tcggctacgc tgcctcgaag     540
agtggtttga cggcgccac gtgccccgac acggccgagt ttggcttcca caacaatggt     600
ttcggacagt ggggtgcagt gctcgagggt gcgacctcgg actcgtatga ggagtgggct     660
cagctggcca ctatcacgcc cccgaccacc tgcgatggca acggccctgg cgacaaggtg     720
tgcgttccgg ctcccgaaga cacgtatgat acatcgttg tcggcgccgg cgccggcggc     780
atcacggtcg ccgacaagct cagcgaggcc ggccacaagg tcctcctat cgagaagggt     840
cctccgtcga ccggcctgtg aacgggacc atgaagcccg agtggctcga gggtaccgac     900
ctcacccgct tcgacgtccc cggtctgtgc aaccagatct gggtcgactc tgccggcatt     960
gcctgcaccg ataccgacca gatggcgggc tgcgttctcg gcggtggcac cgctgtcaat    1020
gctggtctgt ggtggaagcc caccccgct gactgggacg acaacttccc tcatggctgg    1080
aagtcgagcg atctcgcgga tgcgaccgag cgtgtcttca gccgcattcc cggcacgtgg    1140
cacccgtcgc aggatggcaa actgtaccgc caggagggct tcgaggtcat cagccagggc    1200
ctggccaacg ccggctggag ggaagtcgac gccaaccagg agcccagcga agaaccgc      1260
acgtattccc acagtgtgtt catgttctcg ggcggtgagc gcggcggccc cctggcgacg    1320
tacctcgcct cggctgccca gcgcagcaac ttcaacttgt gggtcaacac ttcggtccgg    1380
agggccatcc gcaccggccc cagggtcagt ggcgtcgaac tcgagtgcct tgcggacggc    1440
ggcttcaacg gtactgtcaa cctgaaggag ggtggtggtg tcatcttttc ggctggcgct    1500
ttcggctcgg ccaagctgct ccttcgcagc ggcatcggtc ctgaggacca gctcgagatt    1560
gtggcgagct ccaaggacgg cgagaccttc atttccaaga tgattggat caagctcccc    1620
```

```
gtcggccata acctgatcga tcatctcaac accgacctca ttattactca cccggatgtc    1680
gttttctatg acttctacgc ggcttgggac aatcccatca ccgaggacaa ggaggcctac    1740
ctgaactcgc ggtccggcat tctcgcccaa gcggcgccca acatcggccc tctgatgtgg    1800
gaggaagtca cgccatccga cggcatcacc cgccagttcc agtggacatg ccgtgttgag    1860
ggcgacagct ccaagaccaa ctcgacccac gccatgaccc tcagccagta tctcggccgt    1920
ggcgtcgtct cgcgcggccg gatgggcatc acttccgggc tgaccacgac ggtggccgag    1980
cacccgtacc tgcacaacga cggcgacctg gaggcggtga tccagggtat ccagaacgtg    2040
gtggacgcgc tcagccaggt gcccgacctc gagtgggtgc tcccgccgcc caacacgacg    2100
gtggaggaat acgtcaacag cctgatcgtg tctccggcta accgccgggc aaccactgg     2160
atgggcacgg ccaagatggg cctcgatgac ggccgctcgg gcggctccgc ggtcgtcgac    2220
ctcaacacaa aggtgtatgg caccgacaac ctgtttgtcg tcgacgcctc catcttccct    2280
ggcatgtcga cgggcaaccc gtcggctatg atcgtcatcg tggccgagca ggcggcccag    2340
cgcatcctgt ccctgcggta ttag                                           2364
```

```
<210> SEQ ID NO 9
<211> LENGTH: 829
<212> TYPE: PRT
<213> ORGANISM: S. bisbyi

<400> SEQUENCE: 9
```

| | | | | | | | | | | | | | | |
|---|---|---|---|---|---|---|---|---|---|---|---|---|---|---|
| Met | Leu | Phe | Lys | Leu | Ser | Asn | Trp | Leu | Leu | Ala | Leu | Ala | Leu | Phe | Val |
| 1 | | | | 5 | | | | | 10 | | | | | 15 | |
| Gly | Asn | Val | Val | Ala | Gln | Leu | Glu | Gly | Pro | Thr | Pro | Tyr | Thr | Asp | Pro |
| | | | 20 | | | | | 25 | | | | | 30 | | |
| Asp | Thr | Gly | Ile | Val | Phe | Gln | Ser | Trp | Val | Asn | Pro | Ala | Gly | Thr | Leu |
| | | 35 | | | | | 40 | | | | | 45 | | | |
| Lys | Phe | Gly | Tyr | Thr | Tyr | Pro | Ala | Asn | Ala | Ala | Thr | Val | Ala | Ala | Thr |
| 50 | | | | | 55 | | | | | 60 | | | | | |
| Glu | Phe | Ile | Gly | Phe | Leu | Glu | Cys | Gln | Gly | Ala | Gly | Trp | Cys | Ser | Val |
| 65 | | | | 70 | | | | | 75 | | | | | 80 | |
| Ser | Leu | Gly | Gly | Ser | Met | Leu | Asn | Lys | Pro | Leu | Val | Val | Ala | Tyr | Pro |
| | | | | 85 | | | | | 90 | | | | | 95 | |
| Ser | Gly | Asp | Glu | Val | Leu | Ala | Ser | Leu | Lys | Trp | Ala | Thr | Gly | Tyr | Ala |
| | | | 100 | | | | | 105 | | | | | 110 | | |
| Asn | Pro | Glu | Pro | Tyr | Gly | Gly | Asn | His | Lys | Leu | Ser | Gln | Ile | Ser | Ser |
| | | 115 | | | | | 120 | | | | | 125 | | | |
| Ser | Val | Thr | Ser | Ala | Gly | Phe | Arg | Val | Val | Tyr | Arg | Cys | Glu | Gly | Cys |
| | 130 | | | | | 135 | | | | | 140 | | | | |
| Leu | Ala | Trp | Asn | Tyr | Gln | Gly | Ile | Glu | Gly | Gly | Ser | Pro | Thr | Asn | Gly |
| 145 | | | | | 150 | | | | | 155 | | | | | 160 |
| Ala | Ser | Met | Pro | Ile | Gly | Trp | Ala | Tyr | Ser | Ala | Ser | Ser | Val | Leu | Asn |
| | | | | 165 | | | | | 170 | | | | | 175 | |
| Gly | Asp | Cys | Val | Asp | Asn | Thr | Val | Leu | Ile | Gln | His | Asp | Thr | Phe | Gly |
| | | | 180 | | | | | 185 | | | | | 190 | | |
| Asn | Tyr | Gly | Phe | Val | Pro | Asp | Glu | Ser | Ser | Leu | Arg | Thr | Glu | Tyr | Asn |
| | | 195 | | | | | 200 | | | | | 205 | | | |
| Asp | Trp | Thr | Glu | Leu | Pro | Thr | Arg | Val | Val | Arg | Gly | Asp | Cys | Gly | Gly |
| | 210 | | | | | 215 | | | | | 220 | | | | |
| Ser | Thr | Thr | Thr | Ser | Ser | Val | Pro | Ser | Ser | Thr | Ala | Pro | Pro | Gln | Gly |
| 225 | | | | | 230 | | | | | 235 | | | | | 240 |

```
Thr Gly Ile Pro Val Pro Thr Gly Ala Ser Tyr Asp Tyr Ile Val Val
            245                 250                 255

Gly Ser Gly Ala Gly Gly Ile Pro Ile Ala Asp Lys Leu Thr Glu Ala
            260                 265                 270

Gly Lys Lys Val Leu Leu Ile Glu Lys Gly Pro Pro Ser Ser Gly Arg
            275                 280                 285

Tyr Asp Gly Lys Leu Lys Pro Thr Trp Leu Glu Gly Thr Asn Leu Thr
290                 295                 300

Arg Phe Asp Val Pro Gly Leu Cys Asn Gln Ile Trp Val Asp Ser Ala
305                 310                 315                 320

Gly Ile Ala Cys Arg Asp Thr Asp Gln Met Ala Gly Cys Val Leu Gly
                325                 330                 335

Gly Gly Thr Ala Val Asn Ala Gly Leu Trp Trp Lys Pro Asn Pro Ile
            340                 345                 350

Asp Trp Asp Tyr Asn Phe Pro Ser Gly Trp Lys Ser Ser Glu Met Ile
            355                 360                 365

Gly Ala Thr Asn Arg Val Phe Ser Arg Ile Gly Thr Thr Val Pro
            370                 375                 380

Ser Gln Asp Gly Lys Thr Tyr Tyr Gln Gln Gly Phe Asn Val Leu Ser
385                 390                 395                 400

Ser Gly Leu Lys Ala Ala Gly Trp Thr Ser Val Ser Leu Asn Asn Ala
                405                 410                 415

Pro Ala Gln Arg Asn Arg Thr Tyr Gly Ala Gly Pro Phe Met Phe Ser
            420                 425                 430

Gly Gly Glu Arg Gly Gly Pro Leu Ala Thr Tyr Leu Ala Thr Ala Lys
            435                 440                 445

Lys Arg Gly Asn Phe Asp Leu Trp Thr Asn Thr Gln Val Lys Arg Val
450                 455                 460

Ile Arg Gln Gly Gly His Val Thr Gly Val Glu Val Glu Asn Tyr Asn
465                 470                 475                 480

Gly Asp Gly Tyr Lys Gly Thr Val Lys Val Thr Pro Val Ser Gly Arg
                485                 490                 495

Val Val Leu Ser Ala Gly Thr Phe Gly Ser Ala Lys Leu Leu Leu Arg
            500                 505                 510

Ser Gly Ile Gly Pro Lys Asp Gln Leu Ala Ile Val Lys Asn Ser Thr
            515                 520                 525

Asp Gly Pro Thr Met Ala Ser Glu Arg Asp Trp Ile Asn Leu Pro Val
            530                 535                 540

Gly Tyr Asn Leu Glu Asp His Thr Asn Thr Asp Ile Val Ile Ser His
545                 550                 555                 560

Pro Asp Val Val His Tyr Asp Phe Tyr Glu Ala Trp Thr Ala Ser Ile
                565                 570                 575

Glu Ser Asp Lys Thr Ala Tyr Leu Gly Lys Arg Ser Gly Ile Leu Ala
            580                 585                 590

Gln Ala Ala Pro Asn Ile Gly Pro Leu Phe Phe Asp Glu Val Arg Gly
            595                 600                 605

Ala Asp Asn Ile Val Arg Ser Ile Gln Tyr Thr Ala Arg Val Glu Gly
610                 615                 620

Asn Ser Val Val Pro Asn Gly Lys Ala Met Val Ile Ser Gln Tyr Leu
625                 630                 635                 640

Gly Arg Gly Ala Val Ser Arg Gly Arg Met Thr Ile Ser Gln Gly Leu
                645                 650                 655
```

```
Asn Thr Ile Val Ser Thr Ala Pro Tyr Leu Ser Asn Val Asn Asp Leu
            660                 665                 670

Glu Ala Val Ile Lys Ser Leu Glu Asn Ile Ala Asn Ser Leu Thr Ser
        675                 680                 685

Lys Val Lys Asn Leu Lys Ile Glu Trp Pro Ala Ser Gly Thr Ser Ile
    690                 695                 700

Arg Asp His Val Thr Asn Met Pro Leu Asp Pro Ala Thr Arg Arg Ala
705                 710                 715                 720

Asn His Trp Ile Gly Thr Asn Lys Ile Gly Thr Lys Asn Gly Arg Leu
                725                 730                 735

Thr Gly Gly Asp Ser Val Val Asp Leu Asn Thr Lys Val Tyr Gly Thr
            740                 745                 750

Asp Asn Leu Phe Val Val Asp Ala Ser Ile Phe Pro Gly Met Val Thr
        755                 760                 765

Thr Asn Pro Ser Ala Tyr Ile Val Ile Ala Ala Glu His Ala Ala Ser
    770                 775                 780

Lys Ile Leu Ser Leu Pro Thr Ala Lys Ala Ala Lys Tyr Glu Gln
785                 790                 795                 800

Cys Gly Gly Leu Glu Tyr Asn Gly Asn Phe Gln Cys Ala Ser Gly Leu
                805                 810                 815

Thr Cys Thr Trp Leu Asn Asp Tyr Tyr Trp Gln Cys Thr
            820                 825
```

<210> SEQ ID NO 10
<211> LENGTH: 2490
<212> TYPE: DNA
<213> ORGANISM: S. bisbyi

<400> SEQUENCE: 10

```
atgctgttca agctctcaaa ttggttgcta gcgcttgcgc tctttgttgg caatgtcgtt      60
gctcaactcg aggggcctac cccgtacacg gatccagata ccggcattgt ctttcagtcc     120
tgggtcaatc cagcagggac cctgaagttt ggttacactt accccgcaaa tgctgctacg     180
gttgccgcca cggaatttat cggtttcctg gaatgccaag gggctggatg gtgtagcgtc     240
tcactcggtg gctccatgct taacaagccg cttgttgttg cctaccctag tggcgatgaa     300
gtcctcgctt cttgaagtg ggccacaggc tacgcgaatc cagagcctta cggcggcaat     360
cacaagctgt cccagatcag ctcgtccgtc acctctgctg gcttcagggt cgtctatcga     420
tgtgagggat gtctcgcctg gaactaccag ggaattgagg gagggagccc caccaatggt     480
gcgtccatgc ctatcggttg gcttacagc gcaagttctg tactcaacgg ggattgtgtg     540
gataacactg ttctcattca acatgacacc tttggcaatt atggcttcgt acctgatgaa     600
tcatctcttc gcacggagta caatgactgg acggagcttc cgaccagggt tgtcagggga     660
gactgcggcg gttccacaac tacctcttcg gtgccctcct caacggcgcc tcctcaaggt     720
actggcatac cggttcctac tggcgcaagc tatgactaca gttgttgg ctcgggtgct     780 ggaggtattc ccattgcgga taagcttacc gaggctggca aaaggttttt gttgattgag     840
aagggaccac cctcttctgg tcgctacgat ggaaagctaa agccgacgtg gcttgaggga     900
actaatctca cccgattcga tgtgcctggc ctctgcaacc aaatatgggt cgactccgct     960
ggcattgcat gccgtgatac cgatcagatg gctggttgtg ttcttggcgg tggtactgct    1020
gtcaatgcag gtctatggtg gaagcctaac cctattgatt gggactataa tttcccttca    1080
ggctggaagt caagcgagat gataggcgcg acaaaccgtg tcttttcacg tattggtggt    1140
```

| | |
|---|---|
| actactgttc cttcgcagga cggaaagacc tactatcagc aaggtttcaa cgttctttcc | 1200 |
| agcggtctca aggctgcggg ctggacatct gttagcctga ataacgcccc tgcgcaaagg | 1260 |
| aaccgcacct atggtgctgg cccttctcatg ttctctggtg gagagcgagg tggacctttg | 1320 |
| gccacctacc tggccactgc caagaagaga ggaaacttcg acctctggac gaatacccaa | 1380 |
| gttaagcgtg taattcgaca gggaggtcat gttactggag tggaggtcga aaactataac | 1440 |
| ggtgatgggt acaagggcac tgtcaaggtg actcctgtat ctgggcgagt tgtcctatct | 1500 |
| gctggtacct ttggcagtgc taagcttttg ctccgaagcg gtatcggtcc caaggatcaa | 1560 |
| ctagctattg tcaagaactc gactgatggc cctactatgg cttccgagag ggactggatt | 1620 |
| aatcttcccg ttggctacaa cttggaggac catactaaca ccgacattgt catctcccat | 1680 |
| ccagatgtgg tccattacga cttctatgag gcttggacag cgtcaatcga gtctgacaag | 1740 |
| actgcttatt tgggcaagcg ttctggcatc ctcgctcaag ccgcccccaa catcgggcct | 1800 |
| ctcttctttg acgaagttcg cggtgctgac aacattgtcc gctcaattca gtacactgct | 1860 |
| cgtgtggagg gcaacagtgt ggtccctaat ggcaaggcca tggtgatcag ccagtaccrtt | 1920 |
| ggtcgtggcg ctgtttccag gggtcgaatg accatctctc aaggtctcaa tacgattgtt | 1980 |
| tccaccgctc cataccctctc aaacgtcaat gatctcgagg ccgtcattaa gagccttgag | 2040 |
| aacatagcga acagcttgac gtcaaaggtt aaaaacctca agattgaatg cctgcctct | 2100 |
| ggtacatcca ttcgcgatca cgtcacgaat atgcctctcg acccggccac cgccgagcg | 2160 |
| aatcattgga ttggcactaa caagatcgga accaagaatg gtcgactgac aggtggtgat | 2220 |
| tccgtcgttg atttgaacac taaggtctat ggtacagaca tctgtttgt ggtcgatgct | 2280 |
| tctattttcc ctggcatggt tacgaccaac ccctcggcct acattgtaat tgccgctgag | 2340 |
| catgctgcat cgaagattct gagcctacct actgctaagg ctgccgcgaa gtacgaacaa | 2400 |
| tgtggtggcc ttgaatataa tggtaacttt cagtgtgcgt ctggattaac ctgcacttgg | 2460 |
| ttaaacgact actactggca gtgtacttaa | 2490 |

<210> SEQ ID NO 11
<211> LENGTH: 829
<212> TYPE: PRT
<213> ORGANISM: N. crassa

<400> SEQUENCE: 11

Met Arg Thr Thr Ser Ala Phe Leu Ser Gly Leu Ala Ala Val Ala Ser
1               5                   10                  15

Leu Leu Ser Pro Ala Phe Ala Gln Thr Ala Pro Lys Thr Phe Thr His
                20                  25                  30

Pro Asp Thr Gly Ile Val Phe Asn Thr Trp Ser Ala Ser Asp Ser Gln
            35                  40                  45

Thr Lys Gly Gly Phe Thr Val Gly Met Ala Leu Pro Ser Asn Ala Leu
        50                  55                  60

Thr Thr Asp Ala Thr Glu Phe Ile Gly Tyr Leu Glu Cys Ser Ser Ala
65                  70                  75                  80

Lys Asn Gly Ala Asn Ser Gly Trp Cys Gly Val Ser Leu Arg Gly Ala
                85                  90                  95

Met Thr Asn Asn Leu Leu Ile Thr Ala Trp Pro Ser Asp Gly Glu Val
            100                 105                 110

Tyr Thr Asn Leu Met Phe Ala Thr Gly Tyr Ala Met Pro Lys Asn Tyr
        115                 120                 125

Ala Gly Asp Ala Lys Ile Thr Gln Ile Ala Ser Ser Val Asn Ala Thr

```
            130                 135                 140
His Phe Thr Leu Val Phe Arg Cys Gln Asn Cys Leu Ser Trp Asp Gln
145                 150                 155                 160

Asp Gly Val Thr Gly Gly Ile Ser Thr Ser Asn Lys Gly Ala Gln Leu
                165                 170                 175

Gly Trp Val Gln Ala Phe Pro Ser Pro Gly Asn Pro Thr Cys Pro Thr
            180                 185                 190

Gln Ile Thr Leu Ser Gln His Asp Asn Gly Met Gly Gln Trp Gly Ala
        195                 200                 205

Ala Phe Asp Ser Asn Ile Ala Asn Pro Ser Tyr Thr Ala Trp Ala Ala
210                 215                 220

Lys Ala Thr Lys Thr Val Thr Gly Thr Cys Ser Gly Pro Val Thr Thr
225                 230                 235                 240

Ser Ile Ala Ala Thr Pro Val Pro Thr Gly Val Ser Phe Asp Tyr Ile
                245                 250                 255

Val Val Gly Gly Gly Ala Gly Gly Ile Pro Val Ala Asp Lys Leu Ser
            260                 265                 270

Glu Ser Gly Lys Ser Val Leu Leu Ile Glu Lys Gly Phe Ala Ser Thr
        275                 280                 285

Gly Glu His Gly Gly Thr Leu Lys Pro Glu Trp Leu Asn Asn Thr Ser
290                 295                 300

Leu Thr Arg Phe Asp Val Pro Gly Leu Cys Asn Gln Ile Trp Lys Asp
305                 310                 315                 320

Ser Asp Gly Ile Ala Cys Ser Asp Thr Asp Gln Met Ala Gly Cys Val
                325                 330                 335

Leu Gly Gly Gly Thr Ala Ile Asn Ala Gly Leu Trp Tyr Lys Pro Tyr
            340                 345                 350

Thr Lys Asp Trp Asp Tyr Leu Phe Pro Ser Gly Trp Lys Gly Ser Asp
        355                 360                 365

Ile Ala Gly Ala Thr Ser Arg Ala Leu Ser Arg Ile Pro Gly Thr Thr
370                 375                 380

Thr Pro Ser Gln Asp Gly Lys Arg Tyr Leu Gln Gln Gly Phe Glu Val
385                 390                 395                 400

Leu Ala Asn Gly Leu Lys Ala Ser Gly Trp Lys Glu Val Asp Ser Leu
                405                 410                 415

Lys Asp Ser Glu Gln Lys Asn Arg Thr Phe Ser His Thr Ser Tyr Met
            420                 425                 430

Tyr Ile Asn Gly Glu Arg Gly Gly Pro Leu Ala Thr Tyr Leu Val Ser
        435                 440                 445

Ala Lys Lys Arg Ser Asn Phe Lys Leu Trp Leu Asn Thr Ala Val Lys
450                 455                 460

Arg Val Ile Arg Glu Gly His Ile Thr Gly Val Glu Val Glu Ala
465                 470                 475                 480

Phe Arg Asn Gly Gly Tyr Ser Gly Ile Ile Pro Val Thr Asn Thr Thr
                485                 490                 495

Gly Arg Val Val Leu Ser Ala Gly Thr Phe Gly Ser Ala Lys Ile Leu
            500                 505                 510

Leu Arg Ser Gly Ile Gly Pro Lys Asp Gln Leu Glu Val Val Lys Ala
        515                 520                 525

Ser Ala Asp Gly Pro Thr Met Val Ser Asn Ser Ser Trp Ile Asp Leu
530                 535                 540

Pro Val Gly His Asn Leu Val Asp His Thr Asn Thr Asp Thr Val Ile
545                 550                 555                 560
```

```
Gln His Asn Asn Val Thr Phe Tyr Asp Phe Tyr Lys Ala Trp Asp Asn
                565                 570                 575

Pro Asn Thr Thr Asp Met Asn Leu Tyr Leu Asn Gly Arg Ser Gly Ile
            580                 585                 590

Phe Ala Gln Ala Ala Pro Asn Ile Gly Pro Leu Phe Trp Glu Glu Ile
        595                 600                 605

Thr Gly Ala Asp Gly Ile Val Arg Gln Leu His Trp Thr Ala Arg Val
    610                 615                 620

Glu Gly Ser Phe Glu Thr Pro Asp Gly Tyr Ala Met Thr Met Ser Gln
625                 630                 635                 640

Tyr Leu Gly Arg Gly Ala Thr Ser Arg Gly Arg Met Thr Leu Ser Pro
                645                 650                 655

Thr Leu Asn Thr Val Val Ser Asp Leu Pro Tyr Leu Lys Asp Pro Asn
            660                 665                 670

Asp Lys Ala Ala Val Val Gln Gly Ile Val Asn Leu Gln Lys Ala Leu
        675                 680                 685

Ala Asn Val Lys Gly Leu Thr Trp Ala Tyr Pro Ser Ala Asn Gln Thr
    690                 695                 700

Ala Ala Asp Phe Val Asp Lys Gln Pro Val Thr Tyr Gln Ser Arg Arg
705                 710                 715                 720

Ser Asn His Trp Met Gly Thr Asn Lys Met Gly Thr Asp Asp Gly Arg
                725                 730                 735

Ser Gly Gly Thr Ala Val Val Asp Thr Asn Thr Arg Val Tyr Gly Thr
            740                 745                 750

Asp Asn Leu Tyr Val Val Asp Ala Ser Ile Phe Pro Gly Val Pro Thr
        755                 760                 765

Thr Asn Pro Thr Ala Tyr Ile Val Val Ala Ala Glu His Ala Ala Ala
    770                 775                 780

Lys Ile Leu Ala Gln Pro Ala Asn Glu Ala Val Pro Lys Trp Gly Trp
785                 790                 795                 800

Cys Gly Gly Pro Thr Tyr Thr Gly Ser Gln Thr Cys Gln Ala Pro Tyr
                805                 810                 815

Lys Cys Glu Lys Gln Asn Asp Trp Tyr Trp Gln Cys Val
            820                 825

<210> SEQ ID NO 12
<211> LENGTH: 2490
<212> TYPE: DNA
<213> ORGANISM: N. crassa

<400> SEQUENCE: 12
atgaggacca cctcggcctt tctcagcggc ctggcggcgg tggcttcatt gctgtcgccc    60
gccttcgccc aaaccgctcc caagaccttc actcatcctg taccggcat tgtcttcaac    120 acatggagtg cttccgattc ccagaccaaa ggtggcttca ctgttggtat ggctctgccg    180
tcaaatgctc ttactaccga cgcgactgaa ttcatcggtt atctggaatg ctcctccgcc    240
aagaatggtg ccaatagcgg ttggtgcggt gtttctctca gaggcgccat gaccaacaat    300
ctactcatta ccgcctggcc ttctgacgga gaagtctaca ccaatctcat gttcgccacg    360
ggttacgcca tgcccaagaa ctacgctggt gacgccaaga tcacccagat cgcgtccagc    420
gtgaacgcta cccacttcac cctgtctttt aggtgccaga actgtttgtc atgggaccaa    480
gacggtgtca ccggcggcat ttctaccagc aataagggg cccagctcgg ttgggtccag    540
gcgttcccct ctcccggcaa cccgacttgc cctacccaga tcactctcag tcagcatgac    600
```

-continued

```
aacggtatgg gccagtgggg agctgccttt gacagcaaca ttgccaatcc ctcttatact      660
gcatgggctg ccaaggccac caagaccgtt accggtactt gcagtggtcc agtcacgacc      720
agtattgccg ccactcctgt tcccactggc gtttcttttg actacattgt cgttggtggt      780
ggtgccggtg gtattcccgt cgctgacaag ctcagcgagt ccggtaagag cgtgctgctc      840
atcgagaagg gtttcgcttc cactggtgag catggtggta ctctgaagcc cgagtggctg      900
aataatacat cccttactcg cttcgatgtt cccggtcttt gcaaccagat ctggaaagac      960
tcggatggca ttgcctgctc cgataccgat cagatggccg gctgcgtgct cggcggtggt     1020
accgccatca acgccggtct ctggtacaag ccctacacca aggactggga ctacctcttc     1080
ccctctggct ggaagggcag cgatatcgcc ggtgctacca gcagagccct ctcccgcatt     1140
ccgggtacca ccactccttc tcaggatgga aagcgctacc ttcagcaggg tttcgaggtt     1200
cttgccaacg gcctcaaggc gagcggctgg aaggaggtcg attccctcaa ggacagcgag     1260
cagaagaacc gcactttctc ccacacctca tacatgtaca tcaatggcga gcgtggcggt     1320
cctctagcga cttacctcgt cagcgccaag aagcgcagca acttcaagct gtggctcaac     1380
accgctgtca agcgcgtcat ccgtgagggc ggccacatta ccggtgtgga ggttgaggcc     1440
ttccgcaacg gcggctactc cggaatcatc cccgtcacca acaccaccgg ccgcgtcgtt     1500 cttccgccg gcaccttcgg cagcgccaag atccttctcc gttccggcat ggccccaag      1560 gaccagctcg aggtggtcaa ggcctccgcc gacggcccta ccatggtcag caactcgtcc     1620
tggattgacc tccccgtcgg ccacaacctg gttgaccaca ccaacaccga caccgtcatc     1680
cagcacaaca acgtgaccct ctacgacttt tacaaggctt gggacaaccc caacacgacc     1740
gacatgaacc tgtacctcaa tgggcgctcc ggcatcttcg cccaggccgc gcccaacatt     1800
ggccccttgt tctgggagga gatcacgggc gccgacggca tcgtccgtca gctgcactgg     1860
accgcccgcg tcgagggcag cttcgagacc cccgacggct acgccatgac catgagccag     1920
taccttggcc gtggcgccac ctcgcgcggc cgcatgaccc tcagccctac cctcaacacc     1980
gtcgtgtctg acctcccgta cctcaaggac cccaacgaca aggccgctgt cgttcagggt     2040
atcgtcaacc tccagaaggc tctcgccaac gtcaagggtc tcacctgggc ttaccctagc     2100
gccaaccaga cggctgctga ttttgttgac aagcaacccg taacctacca atcccgccgc     2160
tccaaccact ggatgggcac caacaagatg ggcaccgacg acggccgcag cggcggcacc     2220
gcagtcgtcg acaccaacac gcgcgtctat ggcaccgaca acctgtacgt ggtggacgcc     2280
tcgattttcc ccggtgtgcc gaccaccaac cctaccgcct acattgtcgt cgccgctgag     2340
catgccgcgg ccaaaatcct ggcgcaaccc gccaacgagg ccgttcccaa gtggggctgg     2400
tgcggcgggc cgacgtatac tggcagccag acgtgccagg cgccatataa gtgcgagaag     2460
cagaatgatt ggtattggca gtgtgtgtag                                      2490
```

<210> SEQ ID NO 13
<211> LENGTH: 34
<212> TYPE: DNA
<213> ORGANISM: artificial
<220> FEATURE:
<223> OTHER INFORMATION: anchor primer

<400> SEQUENCE: 13

```
ggccacgcgt cgactagtac ttttttttt tttt                                    34
```

<210> SEQ ID NO 14

```
<211> LENGTH: 21
<212> TYPE: DNA
<213> ORGANISM: artificial
<220> FEATURE:
<223> OTHER INFORMATION: primer

<400> SEQUENCE: 14
atgcctctct tgtttggacc g                                              21

<210> SEQ ID NO 15
<211> LENGTH: 22
<212> TYPE: DNA
<213> ORGANISM: artificial
<220> FEATURE:
<223> OTHER INFORMATION: primer

<400> SEQUENCE: 15
tcaactctca tacttggctt gg                                             22

<210> SEQ ID NO 16
<211> LENGTH: 19
<212> TYPE: DNA
<213> ORGANISM: artificial
<220> FEATURE:
<223> OTHER INFORMATION: primer

<400> SEQUENCE: 16
tagagtcgag gcgaaccag                                                 19

<210> SEQ ID NO 17
<211> LENGTH: 20
<212> TYPE: DNA
<213> ORGANISM: artificial
<220> FEATURE:
<223> OTHER INFORMATION: primer

<400> SEQUENCE: 17
ttgctgctgt gctcctatgc                                                20

<210> SEQ ID NO 18
<211> LENGTH: 23
<212> TYPE: DNA
<213> ORGANISM: artificial
<220> FEATURE:
<223> OTHER INFORMATION: primer

<400> SEQUENCE: 18
tcttgctacg cacttcggta ttg                                            23

<210> SEQ ID NO 19
<211> LENGTH: 21
<212> TYPE: DNA
<213> ORGANISM: artificial
<220> FEATURE:
<223> OTHER INFORMATION: primer

<400> SEQUENCE: 19
tgtgtaccct gtttactcac c                                              21

<210> SEQ ID NO 20
<211> LENGTH: 20
<212> TYPE: DNA
<213> ORGANISM: artificial
<220> FEATURE:
<223> OTHER INFORMATION: primer

<400> SEQUENCE: 20
```
tcttataagc ctttggctcc                                                        20

<210> SEQ ID NO 21
<211> LENGTH: 20
<212> TYPE: DNA
<213> ORGANISM: artificial
<220> FEATURE:
<223> OTHER INFORMATION: primer

<400> SEQUENCE: 21
ttggctccgt tggaacaatg                                                        20

<210> SEQ ID NO 22
<211> LENGTH: 20
<212> TYPE: DNA
<213> ORGANISM: artificial
<220> FEATURE:
<223> OTHER INFORMATION: primer

<400> SEQUENCE: 22
cgcaccaacc gtgtgaagtg                                                        20

<210> SEQ ID NO 23
<211> LENGTH: 21
<212> TYPE: DNA
<213> ORGANISM: artificial
<220> FEATURE:
<223> OTHER INFORMATION: primer

<400> SEQUENCE: 23
tacaagatga ggaccacctc g                                                      21

<210> SEQ ID NO 24
<211> LENGTH: 22
<212> TYPE: DNA
<213> ORGANISM: artificial
<220> FEATURE:
<223> OTHER INFORMATION: primer

<400> SEQUENCE: 24
tacatccagc ttaccggcac tg                                                     22

<210> SEQ ID NO 25
<211> LENGTH: 21
<212> TYPE: DNA
<213> ORGANISM: artificial
<220> FEATURE:
<223> OTHER INFORMATION: primer

<400> SEQUENCE: 25
ttccttccct ccatcaactc c                                                      21

<210> SEQ ID NO 26
<211> LENGTH: 23
<212> TYPE: DNA
<213> ORGANISM: artificial
<220> FEATURE:
<223> OTHER INFORMATION: primer

<400> SEQUENCE: 26
gtacccatta agtacactgc cag                                                    23

<210> SEQ ID NO 27
<211> LENGTH: 20
<212> TYPE: DNA

<210> SEQ ID NO 27
<211> LENGTH: 20
<212> TYPE: DNA
<213> ORGANISM: artificial
<220> FEATURE:
<223> OTHER INFORMATION: primer

<400> SEQUENCE: 27
ttcccccttc gaattcggtc                                          20

<210> SEQ ID NO 28
<211> LENGTH: 21
<212> TYPE: DNA
<213> ORGANISM: artificial
<220> FEATURE:
<223> OTHER INFORMATION: primer

<400> SEQUENCE: 28
agctacctat caccctctgt c                                        21

<210> SEQ ID NO 29
<211> LENGTH: 26
<212> TYPE: DNA
<213> ORGANISM: artificial
<220> FEATURE:
<223> OTHER INFORMATION: primer

<400> SEQUENCE: 29
tccaagcttt taaagatcca ggtaac                                   26

<210> SEQ ID NO 30
<211> LENGTH: 21
<212> TYPE: DNA
<213> ORGANISM: artificial
<220> FEATURE:
<223> OTHER INFORMATION: primer

<400> SEQUENCE: 30
aaaagcttgg acccaaccaa g                                        21

<210> SEQ ID NO 31
<211> LENGTH: 31
<212> TYPE: DNA
<213> ORGANISM: artificial
<220> FEATURE:
<223> OTHER INFORMATION: primer

<400> SEQUENCE: 31
gtcttctatt cttttactc tgcttgggat g                              31

<210> SEQ ID NO 32
<211> LENGTH: 19
<212> TYPE: DNA
<213> ORGANISM: artificial
<220> FEATURE:
<223> OTHER INFORMATION: primer

<400> SEQUENCE: 32
atagaagacc acatcaggg                                           19

<210> SEQ ID NO 33
<211> LENGTH: 2487
<212> TYPE: DNA
<213> ORGANISM: Artificial
<220> FEATURE:
<223> OTHER INFORMATION: codon optimized CDH from Myriococcum
      thermophilum

<400> SEQUENCE: 33

-continued

| | | | | |
|---|---|---|---|---|
| atgagaactt | cttctagact | tatcggtgcc | ttggccgcag | ctttgcttcc | ttctgccctt | 60 |
| gctcagaata | acgttccaaa | cacctttact | gaccctgact | ccggtatcac | tttcaacact | 120 |
| tggggacttg | acgaggattc | tccacagact | cagggtggat | tcactttcgg | tgttgctttg | 180 |
| ccatccgacg | ctttgactac | tgacgcatct | gagttcatcg | gttacttgaa | gtgtgctaga | 240 |
| aatgacgagt | ccggatggtg | tggtatttcc | cttggtggtc | ctatgactaa | ctccttgttg | 300 |
| attactgctt | ggcctcacga | ggacactgtt | tacacttcct | tgagatttgc | taccggatac | 360 |
| gccatgcctg | acgtttacga | gggtgatgct | gaaatcaccc | aagtctcttc | ctctgtcaat | 420 |
| tccactcatt | tctctttgat | ctttagatgt | aagaactgtt | tgcaatggtc | ccacggaggt | 480 |
| tcctctggtg | gtgcttctac | ctccggtggt | gttcttgttc | ttggttgggt | ccaagctttt | 540 |
| gacgatccag | gtaacccaac | ctgtccagaa | cagattactt | tgcagcaaca | cgacaatgga | 600 |
| atgggtattt | ggggtgcaca | attgaatacc | gatgctgcat | ctccatccta | taccgactgg | 660 |
| gctgcacaag | ctaccaagac | cgttaccggt | gattgtgagg | gtcctactga | gacttctgtg | 720 |
| gtcggtgttc | cagttccaac | tggagtttct | ttcgattaca | ttgttgtcgg | aggtggtgcc | 780 |
| ggaggtatcc | cagcagctga | caagcttttct | gaggctggta | agtccgtttt | gcttattgag | 840 |
| aagggtttcg | cttctaccgc | taataccgga | ggtactttgg | gtccagagtg | gttggagggt | 900 |
| cacgatctta | ctcgtttcga | cgttccaggt | cttttgcaacc | aaatttgggt | ggactctaag | 960 |
| ggaatcgctt | gcgaggatac | tgaccaaatg | gcaggatgtg | ttcttggtgg | aggtaccgca | 1020 |
| gtcaatgctg | gtctttggtt | caagccatat | tctttggatt | gggattactt | gtttcctgac | 1080 |
| ggttggaagt | acaacgacgt | ccaacctgcc | atcaacagag | ctttgtctcg | tattcctggt | 1140 |
| actgacgctc | cttctactga | cggaaagaga | tactaccagg | aaggttttga | ggttcttttct | 1200 |
| aaaggtttgg | ccgctggtgg | atggacctct | gtgactgcaa | acaatgctcc | agacaagaag | 1260 |
| aaccgtacct | tcgctcacgc | acctttcatg | ttcgcaggtg | gagagagaaa | cggtccattg | 1320 |
| ggtacctact | tcaaaactgc | caaaaagcgt | aacaacttcg | acgtctggct | taacacttct | 1380 |
| gttaagagag | ttatcagaga | aggaggtcac | attactggag | ttgaagtgga | gcctttcaga | 1440 |
| gatgaggtt | acgagggtat | cgtgcctgtg | actaaggtta | ctggacgtgt | tatcttgtct | 1500 |
| gctggtactt | tcggttccgc | caagattctt | ttgcgttccg | gtattggacc | agaggaccaa | 1560 |
| ttggaggtcg | ttgccgcttc | tgagaaggat | ggacctacca | tgatcggtaa | ctcctcttgg | 1620 |
| attaacttgc | ctgtgggata | caacttggac | gatcacttga | acaccgacac | cgtgatctct | 1680 |
| caccctgatg | tggtcttcta | tgacttttac | gaggcttggg | atgacccaat | tgaatctgac | 1740 |
| aagaactctt | acttggaatc | tagaaccgga | atcttggctc | aagcagctcc | aaacattggt | 1800 |
| ccaatgttct | gggaagagat | tgtgggagct | gacggtattg | tcagacaatt | gcagtggacc | 1860 |
| gccagagttg | agggttcttt | gggtgcacct | aacggacata | ccatgaccat | gtctcaatac | 1920 |
| cttggtcgtg | gtgccacttc | tagaggtaga | atgaccatca | ctccatcttt | gaccactatt | 1980 |
| gtttccgacg | tcccttacct | taaagaccca | aacgacaaag | aagccgtgat | tcaaggtatt | 2040 |
| atcaacttgc | agaatgcttt | gcagaacgtt | gccaatttga | cctggttgtt | cccaaactct | 2100 |
| accattaccc | cacgtgagta | tgtcgaatct | atggtcgtgt | ctccttctaa | cagacgttct | 2160 |
| aaccactgga | tgggtactaa | caaattgggt | actgatgacg | gtagaaaagg | tggatccgca | 2220 |
| gtggttgact | tggacactcg | tgtctatggt | accgataact | tgttcgttat | cgatgcttcc | 2280 |
| atcttccctg | gtgttcctac | cactaaccca | acttcttaca | ttgtcgttgc | cgcagagcac | 2340 |
| gcttcctctc | gtattcttgc | attgccagac | cttgagccag | tccctaaata | cggacagtgt | 2400 |

-continued

```
ggtggaagag agtggactgg atctttcgtt tgcgcagatg gttctacctg tgaataccaa    2460
aatgagtggt actctcaatg tttgtaa                                        2487
```